US012655449B2

(12) United States Patent
Lee et al.

(10) Patent No.: US 12,655,449 B2
(45) Date of Patent: Jun. 16, 2026

(54) GENERATION OF CHIMERIC ANTIGEN RECEPTOR (CAR)-PRIMARY NK CELLS FOR CANCER IMMUNOTHERAPY USING A COMBINATION OF CAS9/RNP AND AAV VIRUSES

(71) Applicant: RESEARCH INSTITUTE AT NATIONWIDE CHILDREN'S HOSPITAL, Columbus, OH (US)

(72) Inventors: Dean Anthony Lee, Canal Winchester, OH (US); Kathrin Christine Meyer, Columbus, OH (US); Meisam Kararoudi, Columbus, OH (US); Shibi Likhite, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 1119 days.

(21) Appl. No.: 17/598,619

(22) PCT Filed: Mar. 27, 2020

(86) PCT No.: PCT/US2020/025454
§ 371 (c)(1),
(2) Date: Sep. 27, 2021

(87) PCT Pub. No.: WO2020/198675
PCT Pub. Date: Oct. 1, 2020

(65) Prior Publication Data
US 2022/0177917 A1     Jun. 9, 2022

Related U.S. Application Data

(60) Provisional application No. 62/825,007, filed on Mar. 27, 2019.

(51) Int. Cl.
| | |
|---|---|
| *C12N 15/86* | (2006.01) |
| *A61K 40/15* | (2025.01) |
| *A61K 40/31* | (2025.01) |
| *A61K 40/42* | (2025.01) |
| *C12N 5/0783* | (2010.01) |
| *C12N 9/22* | (2006.01) |
| *C12N 15/11* | (2006.01) |

(52) U.S. Cl.
CPC ............. *C12N 15/86* (2013.01); *A61K 40/15* (2025.01); *A61K 40/31* (2025.01); *A61K 40/428* (2025.01); *C12N 5/0646* (2013.01); *C12N 9/22* (2013.01); *C12N 15/111* (2013.01); *C12N 2310/20* (2017.05); *C12N 2510/00* (2013.01); *C12N 2750/14143* (2013.01)

(58) Field of Classification Search
CPC ........ C12N 15/86; C12N 5/0646; C12N 9/22; C12N 2310/20; C12N 2510/00; C12N 2501/2321; A61K 40/15; A61K 40/31; A61K 40/428; A61K 40/42
See application file for complete search history.

(56) References Cited

U.S. PATENT DOCUMENTS

| | | |
|---|---|---|
| 2016/0051651 A1 | 2/2016 | Brogdon et al. |
| 2016/0340661 A1 | 11/2016 | Cong et al. |
| 2018/0214490 A1 | 8/2018 | Rebar |
| 2018/0250424 A1 | 9/2018 | Cotta-Ramusino |
| 2018/0296603 A1 | 10/2018 | Gori et al. |
| 2019/0010490 A1 | 1/2019 | Cowan et al. |
| 2019/0022192 A1 | 1/2019 | Ruan et al. |

FOREIGN PATENT DOCUMENTS

| | | |
|---|---|---|
| WO | 2018068008 A1 | 4/2018 |
| WO | 2018/081470 | 5/2018 |
| WO | 2018/204469 | 10/2018 |
| WO | 2019/005957 | 1/2019 |
| WO | 2019/152387 | 8/2019 |
| WO | 2019/222503 | 11/2019 |

OTHER PUBLICATIONS

Imai, C., Iwamoto, S. and Campana, D., 2005. Genetic modification of primary natural killer cells overcomes inhibitory signals and induces specific killing of leukemic cells. Blood, 106(1), pp. 376-383. (Year: 2005).*
Baker O et al. The contribution of homology arms to nuclease-assisted genome engineering, Nucleic Acids Res, 2017, vol. 45, N. 13, pp. 8105-8115.
English translation of Russian Office Action issued in RU2021131306, mailed Sep. 2, 2024.
The Extended European Search Report issued for Application No. 20777892.9, dated Mar. 7, 2023.
Partial Supplementary European Search Report issued for European Application No. 20777892.9, dated Dec. 2, 2022.
Kararoudi, Meisam Naeimi, et al. "Generation of knock-out primary and expanded human NK cells using Cas9 ribonucleoproteins." JoVE (Journal of Visualized Experiments) 136 (2018): e58237.
Gundry, M.C. et al. Highly Efficient Genome Editing of Murine and Human Hematopoietic Progenitor Cells by CRISPR/Cas9. Cell Rep 17, 1453-1461 (2016).

(Continued)

*Primary Examiner* — Jeremy C Flinders
*Assistant Examiner* — Masudur Rahman
(74) *Attorney, Agent, or Firm* — Meunier Carlin & Curfman LLC

(57) ABSTRACT

Disclosed are methods for genetically engineering cells using Adeno-associated viral (AAV) delivery of a CRISPR/CAS9 system and ribonucleoproteins for integration. Said methods include a DNA-free technique for the genome editing of primary and expanded human cells including NK cells) utilizing Cas9 ribonucleoprotein complexes (Cas9/RNPs). In some aspects, disclosed herein are AAV plasmids for performing said methods.

11 Claims, 27 Drawing Sheets

Specification includes a Sequence Listing.

(56) References Cited

OTHER PUBLICATIONS

Mali, P. et al. RNA-guided human genome engineering via Cas9. Science 339, 823-826 (2013).

Suzuki, K. et al. In vivo genome editing via CRISPR/Cas9 mediated homology-independent targeted integration. Nature 540, 144-149 (2016).

Liu, J., Zhou, G., Zhang, L. & Zhao, Q. Building Potent Chimeric Antigen Receptor T Cells With CRISPR Genome Editing. Front Immunol 10, 456 (2019).

McCarty, D.M. Self-complementary AAV vectors; advances and applications. Mol Ther 16, 1648-1656 (2008).

Ran, F.A. et al. Genome engineering using the CRISPR-Cas9 system. Nat Protoc 8, 2281-2308 (2013).

MacLeod, D.T et al. Integration of a CD19 Car into the TCR Alpha Chain Locus Streamlines Production of Allogeneic Gene-Edited CAR T Cells. Mol Ther 25, 949-961 (2017).

He, X. et al. Knock-in of large reporter genes in human cells via CRISPR/Cas9-induced homology-dependent and independent DNA repair. Nucleic Acids Res 44, e85 (2016).

Song, F. & Stieger, K. Optimizing the DNA Donor Template for Homology-Directed Repair of Double-Strand Breaks. Mol Ther Nucleic Acids 7, 53-60 (2017).

Schmid-Burgk, J.L., Honing, K., Ebert, T.S. & Hornung, V. CRISPaint allows modular base-specific gene tagging using a ligase-4-dependent mechanism. Nat Commun 7, 12338 (2016).

Somanchi, S.S., Senyukov, V.V., Denman, C.J. & Lee, D.A. Expansion, purification, and functional assessment of human peripheral blood NK cells. J Vis Exp (2011).

Oceguera-Yanez, F. et al. Engineering the AAVS1 locus for consistent and scalable transgene expression in human iPSCs and their differentiated derivatives. Methods 101, 43-55 (2016).

Hsiau, T. et al. Inference of CRISPR Edits from Sanger Trace Data. bioRxiv, 251082 (2018).

Foust, K.D. et al. Therapeutic AAV9-mediated suppression of mutant SOD1 slows disease progression and extends survival in models of inherited ALS. Mol Ther 21, 2148-2159 (2013).

Mendell, J.R. et al. Single-Dose Gene-Replacement Therapy for Spinal Muscular Atrophy. N Engl J Med 377, 1713-1722 (2017).

Roth, T.L. et al. Reprogramming human T cell function and specificity with non- viral genome targeting. Nature 559, 405-409 (2018).

Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.

Wolff, Jon A., et al. "Direct gene transfer into mouse muscle in vivo." Science 247.4949 (1990): 1465-1468.

Acsadi, Gyula, et al. "Human dystrophin expression in mdx mice after intramuscular injection of DNA constructs." Nature 352.6338 (1991): 815-818.

Ram, Zvi, et al. "In situ retroviral-mediated gene transfer for the treatment of brain tumors in rats." Cancer research 53.1 (1993): 83-88.

Fiers, Walter, et al. "Complete nucleotide sequence of SV40 DNA." Nature 273.5658 (1978): 113-120.

Greenaway, P. J., et al. "Human cytomegalovirus DNA: BamHI, EcoRI and PstI restriction endonuclease cleavage maps." Gene 18.3 (1982): 355-360.

Laimins, L. A., D. B. Rhoads, and W. Epstein. "Osmotic control of kdp operon expression in *Escherichia coli*." Proceedings of the National Academy of Sciences 78.1 (1981): 464-468.

Lusky, M. O. N. I. K. A., et al. "Bovine papilloma virus contains an activator of gene expression at the distal end of the early transcription unit." Molecular and Cellular Biology 3.6 (1983): 1108-1122.

Banerji, Julian, Laura Olson, and Walter Schaffner. "A lymphocyte-specific cellular enhancer is located downstream of the joining region in immunoglobulin heavy chain genes." Cell 33.3 (1983): 729-740.

Osborne, Timothy F., et al. "Transcription control region within the protein-coding portion of adenovirus E1A genes." Molecular and cellular biology 4.7 (1984): 1293- 1305.

Southern, P. J., and P. Berg. "Transformation of mammalian cells to antibiotic resistance with a bacterial gene under control of the SV40 early region promoter." Journal of molecular and applied genetics 1.4 (1982): 327-341.

Mulligan, R. C., and P. Berg. "Expression of a bacterial gene in mammalian cells." Science 209.4463 (1980): 1422-1427.

Sugden, Bill, K. A. T. H. Y. Marsh, and J. O. H. N. Yates. "A vector that replicates as a plasmid and can be efficiently selected in B-lymphoblasts transformed by Epstein-Barr virus." Molecular and cellular biology 5.2 (1985): 410-413.

Creighton, Proteins: Structure and Molecular Properties, W. H. Freeman & Co., San Francisco pp. 79-86 (1983).

Smith, Temple F., and Michael S. Waterman. "Comparison of biosequences." Advances in applied mathematics 2.4 (1981): 482-489.

Needleman, Saul B., and Christian D. Wunsch. "A general method applicable to the search for similarities in the amino acid sequence of two proteins." Journal of molecular biology 48.3 (1970): 443-453.

Pearson, William R., and David J. Lipman. "Improved tools for biological sequence comparison." Proceedings of the National Academy of Sciences 85.8 (1988): 2444-2448.

Zuker, Michael. "On finding all suboptimal foldings of an RNA molecule." Science 244.4900 (1989): 48-52.

Jaeger, John A., Douglas H. Turner, and Michael Zuker. "Improved predictions of secondary structures for RNA." Proceedings of the National Academy of Sciences 86.20 (1989): 7706-7710.

Jaeger, John A., Douglas H. Turner, and Michael Zuker. "[17] Predicting optimal and suboptimal secondary structure for RNA." (1990): 281-306.

Spatola, A. F. in Chemistry and Biochemistry of Amino Acids, Peptides, and Proteins, B. Weinstein, eds., Marcel Dekker, New York, p. 267 (1983).

Morley, J. S. "Modulation of the action of regulatory peptides by structural modification." Trends in Pharmacological Sciences 1.2 (1980): 463-468.

Spatola, Arno F., et al. "Structure-activity relationships of enkephalins containing serially replaced thiomethylene amide bond surrogates." Life sciences 38.14 (1986): 1243-1249.

Hann, Michael M., et al. "On the double bond isostere of the peptide bond: preparation of an enkephalin analogue." Journal of the Chemical Society, Perkin Transactions 1 (1982): 307-314.

Almquist, Ronald G., et al. "Synthesis and biological activity of a ketomethylene analog of a tripeptide inhibitor of angiotensin converting enzyme." Journal of medicinal chemistry 23.12 (1980): 1392-1398.

Jennings-White, C. and R.G. Almquist, Synthesis of Ketomethylene Analogs of Dipeptides. Tetra Lett. 1982; 23(25):2533-4.

Holladay, Mark W., and Daniel H. Rich. "Synthesis of hydroxyethylene and ketomethylene dipeptide isosteres." Tetrahedron Letters 24.41 (1983): 4401-4404.

Hruby, Victor J. "Conformational restrictions of biologically active peptides via amino acid side chain groups." Life sciences 31.3 (1982): 189-199.

Senter, Peter D., et al. "Generation of 5-fluorouracil from 5-fluorocytosine by monoclonal antibody-cytosine deaminase conjugates." Bioconjugate chemistry 2.6 (1991): 447-451.

Bagshawe, K. D. "Towards generating cytotoxic agents at cancer sites. The First Bagshawe Lecture." Br. J. Cancer 60 (1989): 275-281.

Bagshawe, K. D., et al. "A cytotoxic agent can be generated selectively at cancer sites." British journal of cancer 58.6 (1988): 700-703.

Senter, Peter D., et al. "Generation of cytotoxic agents by targeted enzymes." Bioconjugate chemistry 4.1 (1993): 3-9.

Battelli, M. G., et al. "T lymphocyte killing by a xanthine-oxidase-containing immunotoxin." Cancer Immunology, Immunotherapy 35.6 (1992): 421-425.

(56)          References Cited

OTHER PUBLICATIONS

Pietersz, Geoffrey A., and Ian FC McKenzie. "Antibody conjugates for the treatment of cancer." Immunological reviews 129.1 (1992): 57-80.

Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.

Hughes, Brenda J., et al. "Monoclonal antibody targeting of liposomes to mouse lung in vivo." Cancer research 49.22 (1989): 6214-6220.

Litzinger, David C., and Leaf Huang. "Biodistribution and immunotargetability of ganglioside-stabilized dioleoylphosphatidylethanolamine liposomes." Biochimica et Biophysica Acta (BBA)-Biomembranes 1104.1 (1992): 179-187.

Brown, Valerie I., and Mark I. Greene. "Molecular and cellular mechanisms of receptor-mediated endocytosis." DNA and cell biology 10.6 (1991): 399-409.

Petrezselyova S. et al., Homology arms of targeting vectors for gene insertions and CRISPR/Cas9 technology: size does not matter; quality control of targeted clones does, Cell Mol Biol Lett, 2015, vol. 20, N. 5, pp. 773-787.

English translation, Karagyaur et al., Practical recommendations for increasing the efficiency and accuracy of the CRISPR/Cas9 genome editing system, Biochemistry, 2018, vol. 83, issue. 6, p. 800-815, 2018.

English translation of Office Action issued in RU 2021131306/10, mailed Feb. 13, 2024.

International Search Report and Written Opinion mailed Jun. 16, 2020 in PCT/US2020/025454 (13 pages).

Baek et al., "Ex Vivo Expansion of Natural Killer Cells Using Cryopreserved Irradiated Feeder Cells," Anticancer Res, May 31, 2013, vol. 33, pp. 2011-2019.

Notice of Preliminary Rejection for Korean Application No. 10-2021-7034800, dated Oct. 13, 2025, 16 Pages.

* cited by examiner

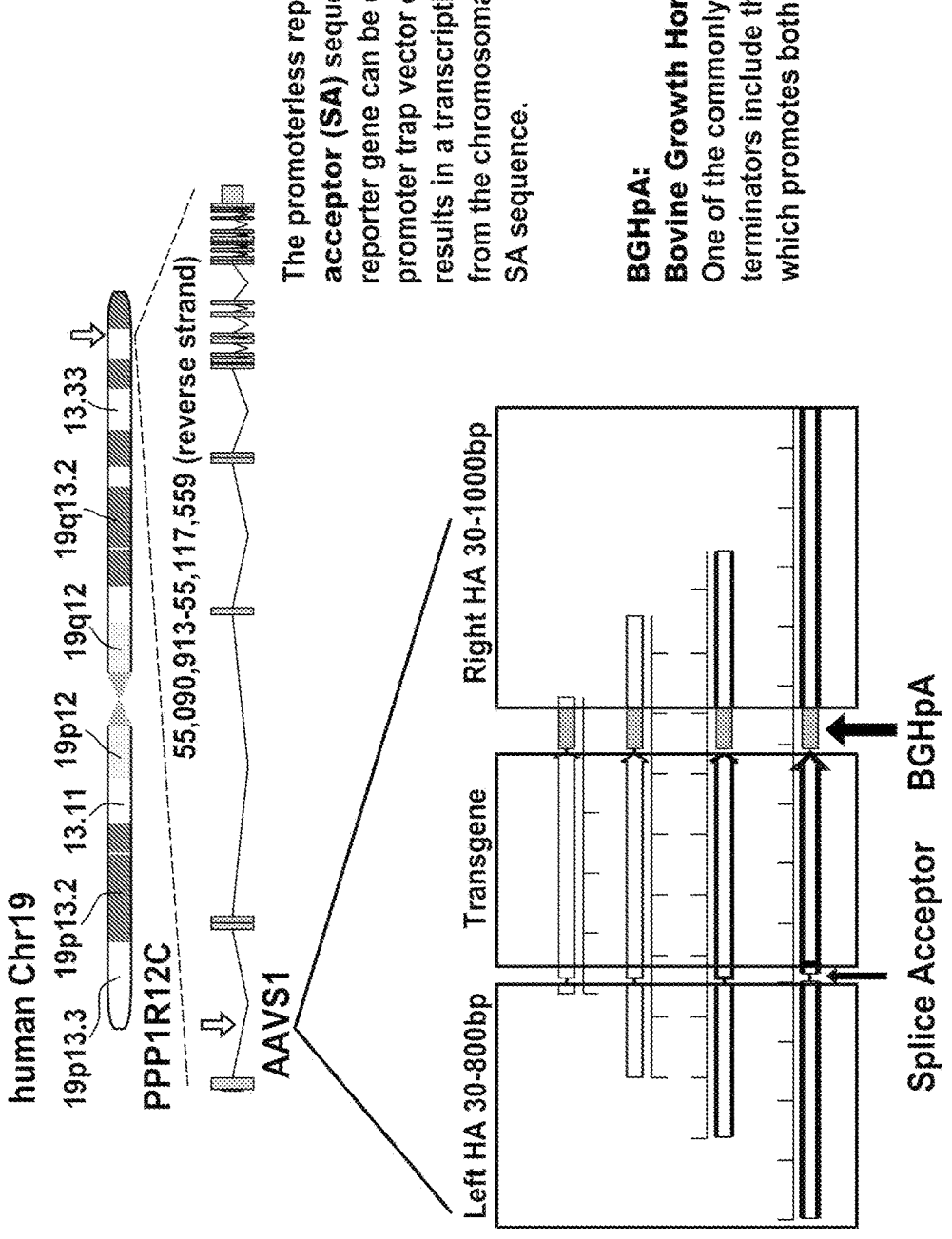

The promoterless reporter gene containes splice acceptor (SA) sequence. The promoterless reporter gene can be expressed when insertion of a promoter trap vector occurs in an intron and results in a transcriptional fusion due to splicing from the chromosomal splice donor (SD) site to the SA sequence.

BGHpA:
Bovine Growth Hormone Polyadenylation Signal
One of the commonly used mammalian expression terminators include the sequence motif AAUAAA which promotes both polyadenylation and termination.

FIG. 1 CONT.

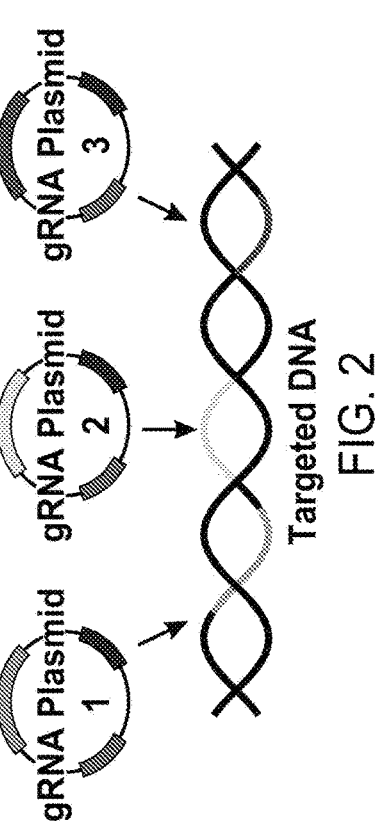

20 nt non-coding RNA sequence: guides CAS9 to a specific target location in the genomic DNA gRNA scaffold: helps Cas9 bind to target DNA Termination signal CBh (chicken ß-Actin hybrid) promoter: drives expression of Cas9

Nuclear localization signal

SpCas9 ribonuclease

U6 promoter: drives expression of gRNA

Green Fluorescent Protein: to visually verify transfection 2A peptide: allows production of both Cas9 and GFP from the same CBh promoter Nuclear localization signal CRISPER/Cas9 Knockout Plasmid gRNA scaffold 20 nt sequence Term CBh

NLS

Cas9

NLS

2A

GFP

U6 gRNA Plasmid 3 gRNA Plasmid 2 gRNA Plasmid 1

Targeted DNA

FIG. 2

The copy number of AAV6 genomic DNA inside NK-cells

Testing new primers to confirm the integration of mCherry reporter gene into AAVS in HEK293 cells
1200bp-mCherry1_forward: AACTCTGCCCTCTAACGCTG: within mCherry gene
1200bp-mCherry1_reverse: CCGTCCTCGAAGTTCATCAC: 1200bp out of the mCherry gene 1200bp-mCherry2_forward: CGCCTACAACGTCAACATC: 1200bp out of the mCherry gene
1200bp-mCherry2_reverse: GAATCCCTCCTCTCTGAACC: within mCherry gene These new primers amplify the mCherry just in case of integration (Not the residual plasmids)
1. NC-AAVS1-No Electroporation Old primers to amplify the AAVS1 gene flanking the Cas9 target site.
2. scPAMPAM+AAVBB DNA electroporation - OLD Primers    (This could amplify also the residual plasmids)
3. ss800+AAVBB DNA electroporation - OLD Primers    (This could amplify also the residual plasmids)

4. NC-No electroporation -1200bp-mCherry1 Primers. This should amplify just the mCherry if is integrated
5. scPAMPAM+AAVBB DNA electroporation - 1200bp-mCherry1 Primers. This should amplify just the mCherry if is integrated
6. Ss800+AAVBB DNA electroporation - 1200bp-mCherry1 Primers. This should amplify just the mCherry if is integrated 7. NC-No electroporation -1200bp-mCherry2 Primers. This should amplify just the mCherry if is integrated
8. scPAMPAM+AAVBB DNA electroporation-1200bp mCherry2 Primers. This should amplify just the mCherry if is integrated
9. Ss800+AAVBB DNA electroporation - 1200bp-mCherry2 Primers. This should amplify just the mCherry if is integrated

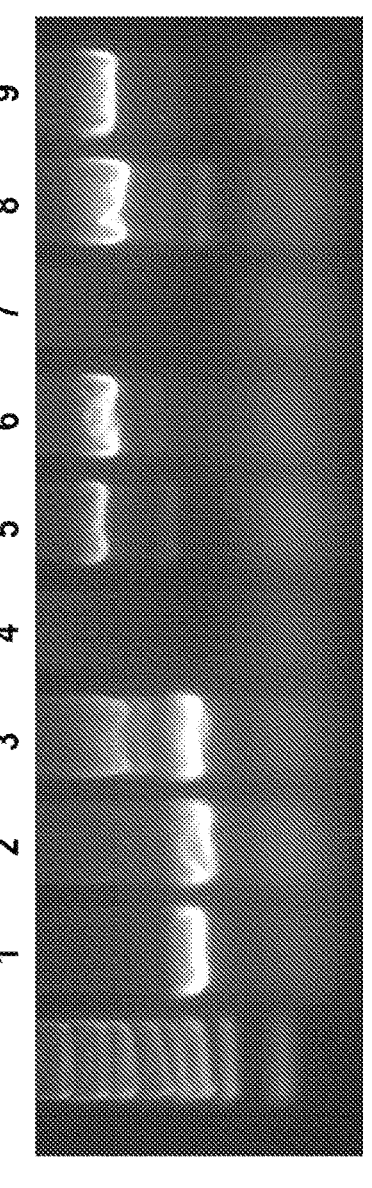

FIG. 5A mCherry positive HEK-293 cells
Electroporated with pDNA of
PAMg condition.
Cas9/RNP+pDNA encoding
mCHerry
5 Days post electroporation mCherry positive HEK-293 cells
Electroporated with pDNA of
PAMg condition.
Cas9/RNP+pDNA encoding
mCHerry
5 Days post electroporation

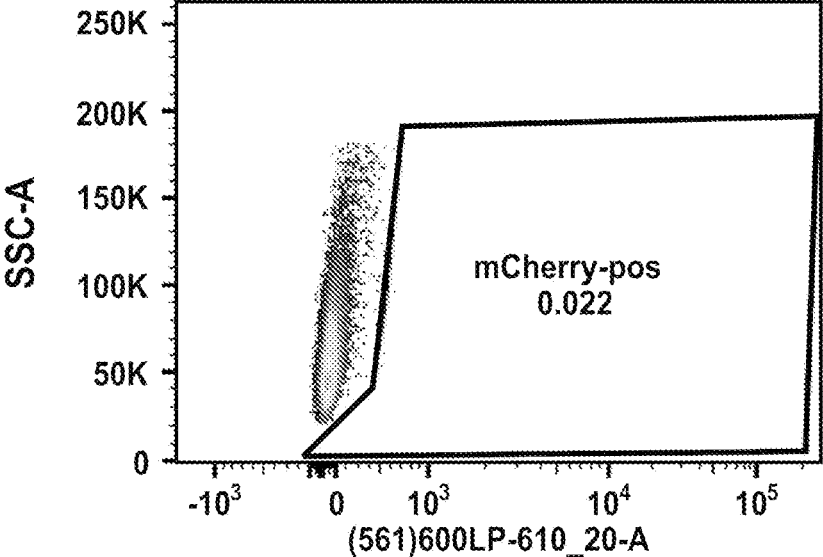
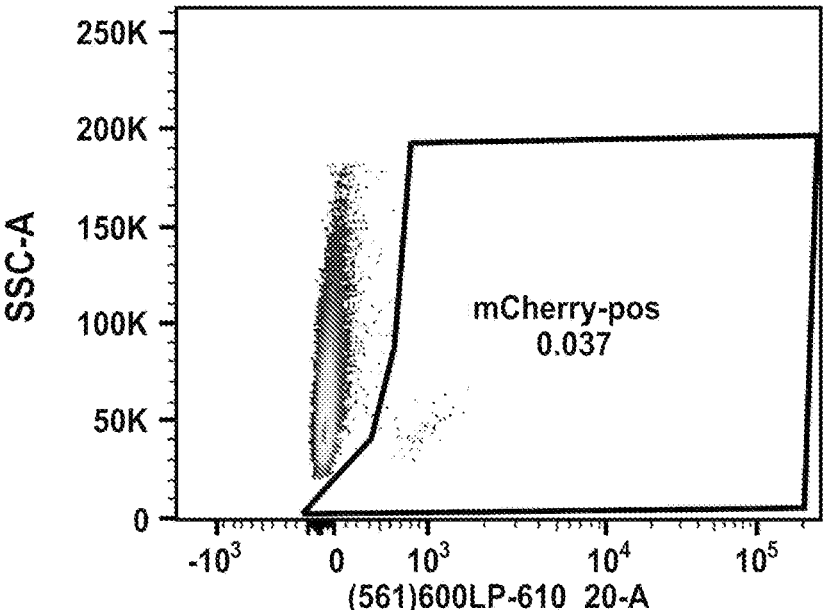
FIG. 6B

30bp mCherry Optimized

LHA  SA          mCherry Codon Optimized          BGHpA  RHA 200        400        600        800

300bp mCherry Optimized

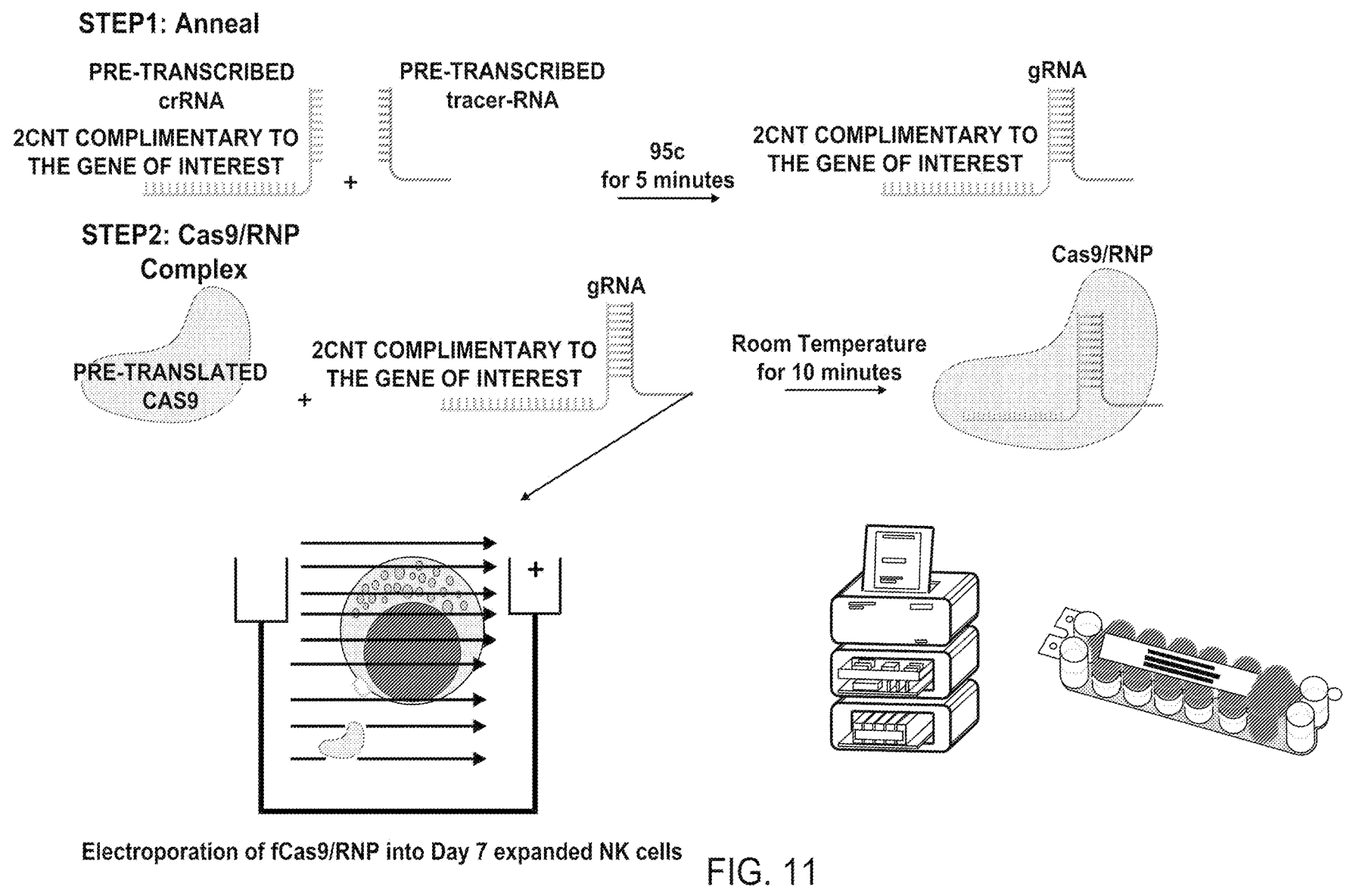

STEP1: Anneal

PRE-TRANSCRIBED
crRNA

2CNT COMPLIMENTARY TO
THE GENE OF INTEREST

+

PRE-TRANSCRIBED
tracer-RNA 95c
for 5 minutes gRNA

2CNT COMPLIMENTARY TO
THE GENE OF INTEREST

**STEP2: Cas9/RNP
Complex**

PRE-TRANSLATED
CAS9

+ gRNA

2CNT COMPLIMENTARY TO
THE GENE OF INTEREST

Room Temperature
for 10 minutes

Cas9/RNP

+

Electroporation of fCas9/RNP into Day 7 expanded NK cells

FIG. 11

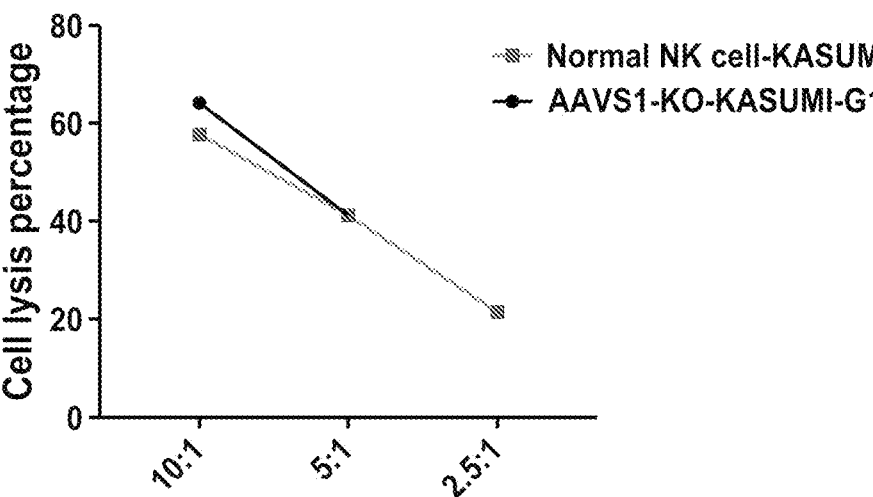
Cytotoxcity of normal NK and AAVS-KO NK cells
againts AML (Kasumi-Cell line)
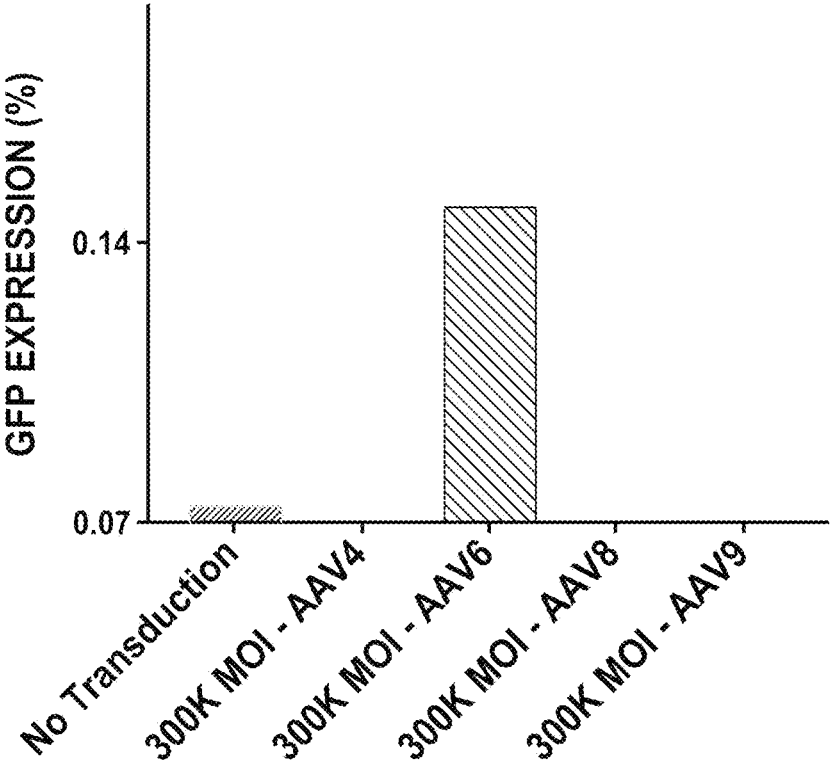
FIG. 13

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Synthetic construct

<400> SEQUENCE: 1
gattggtgac agaaaagccc catccttagg                      30

<210> SEQ ID NO 2
<211> LENGTH: 30
<212> TYPE: DNA
<213> ORGANISM: Artificial Sequence
<220> FEATURE:
<223> OTHER INFORMATION: Synthetic construct

<400> SEQUENCE: 2
ttatctgtcc cctccacccc acagtggggc                      30

<210> SEQ ID NO 3
<211> LENGTH: 300
<212> TYPE: DNA
<213> ORGANISM: Artificial Sequence
<220> FEATURE:
<223> OTHER INFORMATION: Synthetic construct

<400> SEQUENCE: 3
gattggtgac agaaaagccc catccttagg cctcctcctt cctagtctcc tgatattggg     60 tctaacccccc acctcctgtt aggcagattc cttatctggt gacacacccc catttcctgg    120
agccatctct ctccttgcca gaacctctaa ggtttgctta cgatggagcc agagaggatc    180
ctgggaggga gagcttggca gggggtggga gggaaggggg ggatgcgtga cctgcccggt    240
tctcagtggc caccctgcgc taccctctcc cagaacctga gctgctctga cgcggctgtc    300

<210> SEQ ID NO 4
<211> LENGTH: 300
<212> TYPE: DNA
<213> ORGANISM: Artificial Sequence
<220> FEATURE:
<223> OTHER INFORMATION: Synthetic construct

<400> SEQUENCE: 4
gttctcctgt ggattcgggt cacctctcac tcctttcatt tgggcagctc ccctaccccc     60
cttacctctc tagtctgtgc tagctcttcc agcccctgt catggcatct tccagggggtc    120 cgagagctca gctagtcttc ttcctccaac ccgggcccct atgtccactt caggacagca    180
tgtttgctgc ctccagggat cctgtgtccc cgagctggga ccaccttata ttcccagggc    240
cggttaatgt ggctctggtt ctgggtactt ttatctgtcc cctccacccc acagtggggc    300

```
<210> SEQ ID NO 5
<211> LENGTH: 500
<212> TYPE: DNA
<213> ORGANISM: Artificial Sequence
<220> FEATURE:
<223> OTHER INFORMATION: Synthetic construct

<400> SEQUENCE: 5
gattggtgac agaaaagccc catccttagg cctcctcctt cctagtctcc tgatattggg      60 tctaacccc  acctcctgtt aggcagattc cttatctggt gacacacccc catttcctgg     120
agccatctct ctccttgcca gaacctctaa ggtttgctta cgatggagcc agagaggatc     180
ctgggaggga gagcttggca gggggtggga gggaaggggg ggatgcgtga cctgcccggt     240
tctcagtggc caccctgcgc taccctctcc cagaacctga gctgctctga cgcggctgtc     300
tggtgcgttt cactgatcct ggtgctgcag cttccttaca cttcccaaga ggagaagcag     360
tttggaaaaa caaaatcaga ataagttggt cctgagttct aactttggct cttcaccttt     420
ctagtcccca atttatattg ttcctccgtg cgtcagtttt acctgtgaga taaggccagt     480
agccagcccc gtcctggcag                                                 500

<210> SEQ ID NO 6
<211> LENGTH: 500
<212> TYPE: DNA
<213> ORGANISM: Artificial Sequence
<220> FEATURE:
<223> OTHER INFORMATION: Synthetic construct

<400> SEQUENCE: 6 tccctttcc  ttctccttct ggggcctgtg ccatctctcg tttcttagga tggccttctc      60
cgacggatgt ctcccttgcg tcccgcctcc ccttcttgta ggcctgcatc atcaccgttt     120
ttctggacaa ccccaaagta ccccgtctcc ctggctttag ccacctctcc atcctcttgc     180
tttctttgcc tggacacccc gttctcctgt ggattcgggt cacctctcac tcctttcatt     240
tgggcagctc ccctacccc  cttacctctc tagtctgtgc tagctcttcc agccccctgt     300
catggcatct tccaggggtc cgagagctca gctagtcttc ttcctccaac ccgggcccct     360
atgtccactt caggacagca tgtttgctgc ctccagggat cctgtgtccc cgagctggga     420
ccaccttata ttcccagggc cggttaatgt ggctctggtt ctgggtactt ttatctgtcc     480
cctccacccc acagtggggc                                                 500

<210> SEQ ID NO 7
<211> LENGTH: 1000
<212> TYPE: DNA
<213> ORGANISM: Artificial Sequence
<220> FEATURE:
<223> OTHER INFORMATION: Synthetic construct

<400> SEQUENCE: 7
gattggtgac agaaaagccc catccttagg cctcctcctt cctagtctcc tgatattggg      60 tctaacccc  acctcctgtt aggcagattc cttatctggt gacacacccc catttcctgg     120
agccatctct ctccttgcca gaacctctaa ggtttgctta cgatggagcc agagaggatc     180
ctgggaggga gagcttggca gggggtggga gggaaggggg ggatgcgtga cctgcccggt     240
tctcagtggc caccctgcgc taccctctcc cagaacctga gctgctctga cgcggctgtc     300
tggtgcgttt cactgatcct ggtgctgcag cttccttaca cttcccaaga ggagaagcag     360
```

-continued

```
tttggaaaaa caaaatcaga ataagttggt cctgagttct aactttggct cttcaccttt      420
ctagtcccca atttatattg ttcctccgtg cgtcagtttt acctgtgaga taaggccagt      480
agccagcccc gtcctggcag ggctgtggtg aggaggggg tgtccgtgtg gaaaactccc       540
tttgtgagaa tggtgcgtcc taggtgttca ccaggtcgtg gccgcctcta ctcccttcct     600
ctttctccat ccttctttcc ttaaagagtc cccagtgcta tctgggacat attcctccgc      660
ccagagcagg gtcccgcttc cctaaggccc tgctctgggc ttctgggttt gagtccttgg      720
caagcccagg agaggcgctc aggcttccct gtcccccttc ctcgtccacc atctcatgcc      780
cctggctctc ctgcccttc cctacagggg ttcctggctc tgctcttcag actgagcccc       840 gttccctgc atcccgttc ccctgcatcc cccttcccct gcatccccca gaggccccag        900
gccacctact tggcctggac cccacgagag gccaccccag ccctgtctac caggctgcct      960
tttgggtgga ttctcctcca actgtggggt gactgcttgg                            1000
```

<210> SEQ ID NO 8
<211> LENGTH: 804
<212> TYPE: DNA
<213> ORGANISM: Artificial Sequence
<220> FEATURE:
<223> OTHER INFORMATION: Synthetic construct

<400> SEQUENCE: 8

```
tgctttctct gacctgcatt ctctcccctg ggcctgtgcc gctttctgtc tgcagcttgt       60
ggcctgggtc acctctacgg ctggcccaga tccttccctg ccgcctcctt caggttccgt      120
cttcctccac tccctcttcc ccttgctctc tgctgtgttg ctgcccaagg atgctctttc     180
cggagcactt ccttctcggc gctgcaccac gtgatgtcct ctgagcggat cctccccgtg      240
tctgggtcct ctccgggcat ctctcctccc tcacccaacc ccatgccgtc ttcactcgct      300
gggttccctt ttccttctcc ttctggggcc tgtgccatct ctcgtttctt aggatggcct      360
tctccgacgg atgtctccct tgcgtcccgc ctccccttct tgtaggcctg catcatcacc      420
gtttttctgg acaaccccaa agtaccccgt ctccctggct ttagccacct ctccatcctc      480
ttgctttctt tgcctggaca ccccgttctc ctgtggattc gggtcacctc tcactccttt      540
catttgggca gctcccctac cccccttacc tctctagtct gtgctagctc ttccagcccc      600
ctgtcatggc atcttccagg ggtccgagag ctcagctagt cttcttcctc caacccgggc      660
ccctatgtcc acttcaggac agcatgtttg ctgcctccag ggatcctgtg tccccgagct       720
gggaccacct tatattccca gggccggtta atgtggctct ggttctgggt acttttatct       780
gtcccctcca ccccacagtg gggc                                             804
```

<210> SEQ ID NO 9
<211> LENGTH: 23
<212> TYPE: DNA
<213> ORGANISM: Artificial Sequence
<220> FEATURE:
<223> OTHER INFORMATION: Synthetic construct

<400> SEQUENCE: 9

```
ccaatcctgt ccctagtggc ccc                                               23
```

<210> SEQ ID NO 10
<211> LENGTH: 39
<212> TYPE: DNA
<213> ORGANISM: Artificial Sequence
<220> FEATURE:
<223> OTHER INFORMATION: Synthetic construct

```
<400> SEQUENCE: 10
atcgatcgca ggcgcaatct tcgcatttct tttttccag                              39

<210> SEQ ID NO 11
<211> LENGTH: 147
<212> TYPE: DNA
<213> ORGANISM: Artificial Sequence
<220> FEATURE:
<223> OTHER INFORMATION: Synthetic construct

<400> SEQUENCE: 11
cctcgactgt gccttctagt tgccagccat ctgttgtttg cccctccccc gtgccttcct       60
tgaccctgga aggtgccact cccactgtcc tttcctaata aaatgaggaa attgcatcgc      120
attgtctgag taggtgtcat tctattc                                          147

<210> SEQ ID NO 12
<211> LENGTH: 708
<212> TYPE: DNA
<213> ORGANISM: Artificial Sequence
<220> FEATURE:
<223> OTHER INFORMATION: Synthetic construct

<400> SEQUENCE: 12
gtgagcaagg gcgaggagga taacatggcc atcatcaagg agttcatgcg cttcaaggtg       60
cacatggagg gctccgtgaa cggccacgag ttcgagatcg agggcgaggg cgagggccgc      120
ccctacgagg gcacccagac cgccaagctg aaggtgacca aggtggccc  cctgcccttc      180 gcctgggaca tcctgtcccc tcagttcatg tacggctcca aggcctacgt gaagcacccc      240
gccgacatcc ccgactactt gaagctgtcc ttccccgagg gcttcaagtg ggagcgcgtg      300
atgaacttcg aggacggcgg cgtggtgacc gtgacccagg actcctccct gcaggacggc      360
gagttcatct acaaggtgaa gctgcgcggc accaacttcc cctccgacgg ccccgtaatg      420
cagaagaaga ccatgggctg ggaggcctcc tccgagcgga tgtaccccga ggacggcgcc      480
ctgaagggcg agatcaagca gaggctgaag ctgaaggacg gcggccacta cgacgctgag      540
gtcaagacca cctacaaggc caagaagccc gtgcagctgc ccggcgccta caacgtcaac      600
atcaagttgg acatcacctc ccacaacgag gactacacca tcgtggaaca gtacgaacgc      660
gccgagggcc gccactccac cggcggcatg gacgagctgt acaagtaa               708

<210> SEQ ID NO 13
<211> LENGTH: 986
<212> TYPE: DNA
<213> ORGANISM: Artificial Sequence
<220> FEATURE:
<223> OTHER INFORMATION: Synthetic construct

<400> SEQUENCE: 13
ttatctgtcc cctccacccc acagtggggc cactagggac agcgatcggg tacatcgatc       60
gcaggcgcaa tcttcgcatt tctttttttcc aggtgagcaa gggcgaggag ataacatgg      120 ccatcatcaa ggagttcatg cgcttcaagg tgcacatgga gggctccgtg aacggccacg      180
agttcgagat cgagggcgag ggcgagggcc gcccctacga gggcacccag accgccaagc      240
tgaaggtgac caagggtggc cccctgccct cgcctggga catcctgtcc cctcagttca      300
tgtacggctc caaggcctac gtgaagcacc ccgccgacat ccccgactac ttgaagctgt      360
ccttccccga gggcttcaag tgggagcgcg tgatgaactt cgaggacggc ggcgtggtga      420
```

-continued

```
ccgtgaccca ggactcctcc ctgcaggacg gcgagttcat ctacaaggtg aagctgcgcg    480
gcaccaactt cccctccgac ggccccgtaa tgcagaagaa gaccatgggc tgggaggcct    540
cctccgagcg gatgtacccc gaggacggcg ccctgaaggg cgagatcaag cagaggctga    600
agctgaagga cggcggccac tacgacgctg aggtcaagac cacctacaag gccaagaagc    660
ccgtgcagct gcccggcgcc tacaacgtca acatcaagtt ggacatcacc tcccacaacg    720
aggactacac catcgtggaa cagtacgaac gcgccgaggg ccgccactcc accgcggca    780 tggacgagct gtacaagtaa cgcggccgcc ctcgactgtg ccttctagtt gccagccatc    840
tgttgtttgc ccctcccccg tgccttcctt gaccctggaa ggtgccactc ccactgtcct    900
ttcctaataa aatgaggaaa ttgcatcgca ttgtctgagt aggtgtcatt ctattcgatt    960
ggtgacagaa aagccccatc cttagg    986

<210> SEQ ID NO 14
<211> LENGTH: 1526
<212> TYPE: DNA
<213> ORGANISM: Artificial Sequence
<220> FEATURE:
<223> OTHER INFORMATION: Synthetic construct

<400> SEQUENCE: 14
gttctcctgt ggattcgggt cacctctcac tcctttcatt tgggcagctc ccctacccccc     60 cttacctctc tagtctgtgc tagctcttcc agcccctgt catggcatct tccaggggtc    120
cgagagctca gctagtcttc ttcctccaac ccgggcccct atgtccactt caggacagca    180
tgtttgctgc ctccagggat cctgtgtccc cgagctggga ccaccttata ttcccagggc    240
cggttaatgt ggctctggtt ctgggtactt ttatctgtcc cctccacccc acagtggggc    300 cactaggac agcgatcggg tacatcgatc gcaggcgcaa tcttcgcatt tcttttttcc    360
aggtgagcaa gggcgaggag gataacatgg ccatcatcaa ggagttcatg cgcttcaagg    420
tgcacatgga gggctccgtg aacggccacg agttcgagat cgaggcgag ggcgagggcc    480 gcccctacga gggcacccag accgccaagc tgaaggtgac caagggtggc cccctgccct    540
tcgcctggga catcctgtcc cctcagttca tgtacggctc caaggcctac gtgaagcacc    600
ccgccgacat ccccgactac ttgaagctgt ccttccccga gggcttcaag tgggagcgcg    660
tgatgaactt cgaggacggc ggcgtggtga ccgtgaccca ggactcctcc ctgcaggacg    720
gcgagttcat ctacaaggtg aagctgcgcg gcaccaactt cccctccgac ggccccgtaa    780
tgcagaagaa gaccatgggc tgggaggcct cctccgagcg gatgtacccc gaggacggcg    840
ccctgaaggg cgagatcaag cagaggctga agctgaagga cggcggccac tacgacgctg    900
aggtcaagac cacctacaag gccaagaagc ccgtgcagct gcccggcgcc tacaacgtca    960
acatcaagtt ggacatcacc tcccacaacg aggactacac catcgtggaa cagtacgaac   1020
gcgccgaggg ccgccactcc accgcggca tggacgagct gtacaagtaa cgcggccgcc   1080
ctcgactgtg ccttctagtt gccagccatc tgttgtttgc ccctcccccg tgccttcctt   1140
gaccctggaa ggtgccactc ccactgtcct ttcctaataa aatgaggaaa ttgcatcgca   1200
ttgtctgagt aggtgtcatt ctattcgatt ggtgacagaa aagccccatc cttaggcctc   1260
ctccttccta gtctcctgat attgggtcta acccccacct cctgttaggc agattcctta   1320
tctggtgaca cacccccatt tcctggagcc atctctctcc ttgccagaac ctctaaggtt   1380
tgcttacgat ggagccagag aggatcctgg gaggagagc ttggcagggg gtgggaggga   1440
agggggggat gcgtgacctg cccggttctc agtggccacc ctgcgctacc ctctcccaga   1500
```

-continued

```
acctgagctg ctctgacgcg gctgtc                                          1526

<210> SEQ ID NO 15
<211> LENGTH: 1926
<212> TYPE: DNA
<213> ORGANISM: Artificial Sequence
<220> FEATURE:
<223> OTHER INFORMATION: Synthetic construct

<400> SEQUENCE: 15
tcccttttcc ttctccttct ggggcctgtg ccatctctcg tttcttagga tggccttctc      60
cgacggatgt ctcccttgcg tcccgcctcc ccttcttgta ggcctgcatc atcaccgttt     120
ttctggacaa ccccaaagta ccccgtctcc ctggctttag ccacctctcc atcctcttgc     180
tttctttgcc tggacacccc gttctcctgt ggattcgggt cacctctcac tcctttcatt     240
tgggcagctc ccctaccccc cttacctctc tagtctgtgc tagctcttcc agccccctgt     300
catggcatct tccaggggtc cgagagctca gctagtcttc ttcctccaac ccgggcccct     360
atgtccactt caggacagca tgtttgctgc ctccagggat cctgtgtccc cgagctggga     420
ccaccttata ttcccagggc cggttaatgt ggctctggtt ctgggtactt ttatctgtcc     480
cctccacccc acagtggggc cactagggac agcgatcggg tacatcgatc gcaggcgcaa     540
tcttcgcatt tctttttttcc aggtgagcaa gggcgaggag gataacatgg ccatcatcaa     600
ggagttcatg cgcttcaagg tgcacatgga gggctccgtg aacggccacg agttcgagat     660
cgagggcgag ggcgagggcc gcccctacga gggcacccag accgccaagc tgaaggtgac     720
caagggtggc cccctgccct tcgcctggga catcctgtcc cctcagttca tgtacggctc     780
caaggcctac gtgaagcacc ccgccgacat ccccgactac ttgaagctgt ccttccccga     840
gggcttcaag tgggagcgcg tgatgaactt cgaggacggc ggcgtggtga ccgtgaccca     900
ggactcctcc ctgcaggacg gcgagttcat ctacaaggtg aagctgcgcg gcaccaactt     960
cccctccgac ggccccgtaa tgcagaagaa gaccatgggc tgggaggcct cctccgagcg    1020
gatgtacccc gaggacggcg ccctgaaggg cgagatcaag cagaggctga agctgaagga    1080
cggcggccac tacgacgctg aggtcaagac cacctacaag gccaagaagc ccgtgcagct    1140
gcccggcgcc tacaacgtca acatcaagtt ggacatcacc tcccacaacg aggactacac    1200
catcgtggaa cagtacgaac gcgccgaggg ccgccactcc accggcggca tggacgagct    1260
gtacaagtaa cgcggccgcc ctcgactgtg ccttctagtt gccagccatc tgttgtttgc    1320
ccctcccccg tgccttcctt gaccctggaa ggtgccactc ccactgtcct ttcctaataa    1380
aatgaggaaa ttgcatcgca ttgtctgagt aggtgtcatt ctattcgatt ggtgacagaa    1440
aagccccatc cttaggcctc ctccttccta gtcctgat attgggtcta accccccacct    1500 cctgttaggc agattcctta tctggtgaca cacccccatt tcctggagcc atctctctcc    1560
ttgccagaac ctctaaggtt tgcttacgat ggagccagag aggatcctgg gagggagagc    1620
ttggcagggg gtgggaggga aggggggggat gcgtgacctg cccggttctc agtggccacc    1680
ctgcgctacc ctctcccaga acctgagctg ctctgacgcg gctgtctggt gcgtttcact    1740
gatcctggtg ctgcagcttc cttacacttc caagaggag aagcagtttg gaaaaacaaa    1800
atcagaataa gttggtcctg agttctaact ttggctcttc acctttctag tccccaattt    1860
atattgttcc tccgtgcgtc agttttacct gtgagataag gccagtagcc agccccgtcc    1920
tggcag                                                              1926
```

-continued

```
<210> SEQ ID NO 16
<211> LENGTH: 2730
<212> TYPE: DNA
<213> ORGANISM: Artificial Sequence
<220> FEATURE:
<223> OTHER INFORMATION: Synthetic construct

<400> SEQUENCE: 16
tgctttctct gacctgcatt ctctcccctg ggcctgtgcc gctttctgtc tgcagcttgt      60
ggcctgggtc acctctacgg ctggcccaga tccttccctg ccgcctcctt caggttccgt     120
cttcctccac tccctcttcc ccttgctctc tgctgtgttg ctgcccaagg atgctctttc     180
cggagcactt ccttctcggc gctgcaccac gtgatgtcct ctgagcggat cctccccgtg     240
tctgggtcct ctccgggcat ctctcctccc tcacccaacc ccatgccgtc ttcactcgct     300
gggttccctt ttccttctcc ttctggggcc tgtgccatct ctcgtttctt aggatggcct     360
tctccgacgg atgtctccct tgcgtcccgc ctcccccttct tgtaggcctg catcatcacc     420
gtttttctgg acaaccccaa agtaccccgt ctccctggct ttagccacct ctccatcctc     480
ttgctttctt tgcctggaca ccccgttctc ctgtggattc gggtcacctc tcactccttt     540
catttgggca gctcccctac ccccccttacc tctctagtct gtgctagctc ttccagcccc     600
ctgtcatggc atcttccagg ggtccgagag ctcagctagt cttcttcctc caacccgggc     660
ccctatgtcc acttcaggac agcatgtttg ctgcctccag ggatcctgtg tccccgagct     720
gggaccacct tatattccca gggccggtta atgtggctct ggttctgggt acttttatct     780
gtcccctcca ccccacagtg gggccactag ggacagcgat cgggtacatc gatcgcaggc     840
gcaatcttcg catttctttt ttccaggtga gcaagggcga ggaggataac atggccatca     900
tcaaggagtt catgcgcttc aaggtgcaca tggagggctc cgtgaacggc cacgagttcg     960
agatcgaggg cgagggcgag ggccgcccct acgagggcac ccagaccgcc aagctgaagg    1020
tgaccaaggg tggccccctg cccttcgcct gggacatcct gtcccctcag ttcatgtacg    1080
gctccaaggc ctacgtgaag caccccgccg acatccccga ctacttgaag ctgtccttcc    1140
ccgagggctt caagtgggag cgcgtgatga acttcgagga cggcggcgtg gtgaccgtga    1200
cccaggactc ctccctgcag gacggcgagt tcatctacaa ggtgaagctg cgcggcacca    1260
acttcccctc cgacggcccc gtaatgcaga agaagaccat gggctgggag gcctcctccg    1320
agcggatgta ccccgaggac ggcgccctga agggcgagat caagcagagg ctgaagctga    1380
aggacggcgg ccactacgac gctgaggtca agaccaccta caaggccaag aagcccgtgc    1440
agctgcccgg cgcctacaac gtcaacatca gttggacat cacctcccac aacgaggact    1500
acaccatcgt ggaacagtac gaacgcgccg agggccgcca ctccaccggc ggcatggacg    1560
agctgtacaa gtaacgcggc cgccctcgac tgtgccttct agttgccagc catctgttgt    1620
ttgcccctcc cccgtgcctt ccttgaccct ggaaggtgcc actcccactg tcctttccta    1680
ataaaatgag gaaattgcat cgcattgtct gagtaggtgt cattctattc gattggtgac    1740
agaaaagccc catccttagg cctcctcctt cctagtctcc tgatattggg tctaacccccc    1800 acctcctgtt aggcagattc cttatctggt gacacacccc catttcctgg agccatctct    1860
ctccttgcca gaacctctaa ggtttgctta cgatggagcc agagaggatc ctgggaggga    1920
gagcttggca gggggtggga gggaggggg ggatgcgtga cctgcccggt tctcagtggc    1980
caccctcgcg tacctctcc cagaacctga gctgctctga cgcggctgtc tggtgcgttt    2040
cactgatcct ggtgctgcag cttccttaca cttcccaaga ggagaagcag tttggaaaaa    2100
```

-continued

```
caaaatcaga ataagttggt cctgagttct aactttggct cttcaccttt ctagtcccca    2160
atttatattg ttcctccgtg cgtcagtttt acctgtgaga taaggccagt agccagcccc    2220
gtcctggcag ggctgtggtg aggaggggg tgtccgtgtg gaaaactccc tttgtgagaa     2280
tggtgcgtcc taggtgttca ccaggtcgtg gccgcctcta ctcccttct ctttctccat     2340 ccttctttcc ttaaagagtc cccagtgcta tctgggacat attcctccgc ccagagcagg    2400
gtcccgcttc cctaaggccc tgctctgggc ttctgggttt gagtccttgg caagcccagg    2460
agaggcgctc aggcttccct gtcccccttc ctcgtccacc atctcatgcc cctggctctc    2520
ctgccccttc cctacagggg ttcctggctc tgctcttcag actgagcccc gttcccctgc    2580
atccccgttc ccctgcatcc cccttcccct gcatccccca gaggccccag gccacctact    2640
tggcctggac cccacgagag gccacccag ccctgtctac caggctgcct tttgggtgga     2700
ttctcctcca actgtggggt gactgcttgg                                     2730
```

```
<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
ggggccacta gggacaggat                                                20
```

GENERATION OF CHIMERIC ANTIGEN RECEPTOR (CAR)-PRIMARY NK CELLS FOR CANCER IMMUNOTHERAPY USING A COMBINATION OF CAS9/RNP AND AAV VIRUSES

CROSS REFERENCE TO RELATED APPLICATIONS

This application is a United States National Phase Patent Application of International Patent Application Number PCT/US2020/025454, filed on Mar. 27, 2020, which claims the benefit of priority to U.S. Provisional Application No. 62/825,007, filed Mar. 27, 2019, applications which are incorporated by reference herein in their entirety.

I. BACKGROUND

CRISPR/Cas9 technology has been used recently in engineering cells. The technology has proven a robust method for silencing genes by creating DNA breaks or making small substitutions or small insertions. However, the technology is beset by technological hurdles. Techniques for delivering CRISPR/Cas9 into a cell (along with any donor DNA or RNA) such as microinjection, electroporation, and nucleofection are not suitable for in vivo use. Moreover, knock-in mutations typically have very low efficiency in in vitro, in vivo, and clinical applications. Using viral vectors to deliver CRISPR/Cas9 into a cell (along with any donor DNA or RNA) addresses the in vivo suitability, but has limitations with transgene size and can induce host immune responses lead to substantial procedure-associated cell apoptosis and the limited production of genetically engineered cells. What are needed are new methods of genetically and vectors for engineering cells.

II. SUMMARY

Disclosed are methods and compositions related to AAV plasmids for delivery of a CRISPR/CAS9 gene editing system to a cell. In some aspect, the AAV plasmids further comprise a transgene.

In one aspect, disclosed herein are plasmids for use in clustered regularly interspaced short palindromic repeat (CRISPR)/CRISPR-associated 9 (Cas9) integration systems wherein the plasmid comprises in order a left homology arm, a splice acceptor, a transgene, and a right homology arm; wherein the left and right homology arms are each 800 bp in length or less (such as for example 30 bp in plasmids 1 and 2, 300 bp in plasmids 3 and 4, 500 bp in plasmids 5 and 6, or 800 bp). In some aspect, the plasmid can further comprise a polyadenylation signal between the transgene and the right homology arm.

Also disclosed herein are plasmids of any preceding aspect, wherein the left homology arm and right homology arm are the same length or different lengths.

In one aspect, disclosed herein are plasmids for use in CRISPaint (or non-homologous end joining) methods consisting of 1 or 2 protospacer adjacent motifs (PAMs) and CRISPR RNAs (crRNAs) and a transgene; wherein the order of the encoded nucleic acid comprises a PAM, a gRNA and a transgene; and wherein when 2 PAMs and gRNAs are used, of the encoded nucleic acid comprises a first PAM, a first gRNA, a transgene, a second PAM, and second gRNA.

In one aspect, disclosed herein are plasmids of any preceding aspect, wherein the homology arms or the PAMs of the plasmid specifically hybridize to the Adeno-Associated Virus Integration Site 1 (AAVS1) of chromosome 19 of humans.

Also disclosed are plasmids of any preceding aspect, wherein the transgene comprises a polynucleotide encoding a chimeric antigen receptor for a tumor antigen.

In one aspect, disclosed herein are Adeno-associated viral (AAV) vectors (such as an AAV vector of serotype AAV6) comprising the plasmid of any preceding aspect. In one aspect, the AAV can be a single stranded AAV or a self-complementary AAV.

Also disclosed herein are vectors of any preceding wherein the vector further comprises a plasmid encoding a gRNA (a crispr RNA (crRNA), tracer RNA (tracrRNA)), and a CAS endonuclease.

In one aspect, disclosed herein are modified cells comprising the plasmid or vector of any preceding aspect.

Also disclosed herein are methods of treating a cancer in a subject comprising administering to a subject with a cancer the modified cell of any of any preceding aspect.

In one aspect, disclosed herein are methods of genetically modifying a cell (T cells, B cells, macrophages, NK cells, fibroblasts, osteoblasts, hepatocytes, neuronal cells, epithelial cells, and/or muscle cells, including, but not limited to primary or expanded cells) by homologously directed repair comprising a) obtaining a ribonucleoprotein (RNP) complex comprising a class 2 CRISPR/Cas endonuclease (Cas9) complexed with a corresponding CRISPR/Cas guide RNA and an AAV vector comprising a plasmid comprising a transgene (such as, for example, a chimeric antigen receptor for a tumor antigen); wherein the transgene is flanked by homology arms; and wherein the homology arms are 800 bp in length or less; and b) introducing the transgene and the RNP complex into the cell; wherein the transgene is introduced into the cell via infection with the Adeno-associated virus (AAV) into the cell; wherein the RNP complex hybridizes to a target sequence within the genomic DNA of the cell and the cell's DNA repair enzymes insert the transgene into the host genome (for example, by homologous repair) at the target sequence, thereby creating a modified cell. In some aspects, the RNP complex can be introduced into the cell via electroporation. In some aspect, the RNP complex can be introduced into the cell via viral delivery in the same or a different AAV (i.e., superinfection).

In one aspect, disclosed herein are methods of genetically modifying a cell (T cells, B cells, macrophages, NK cells, fibroblasts, osteoblasts, hepatocytes, neuronal cells, epithelial cells, and/or muscle cells, including, but not limited to primary or expanded cells) by non-homologous end joining comprising a) obtaining a ribonucleoprotein (RNP) complex comprising a class 2 CRISPR/Cas endonuclease (Cas9) complexed with a corresponding CRISPR/Cas guide RNA and an AAV vector comprising a plasmid comprising a transgene (such as, for example, a chimeric antigen receptor for a tumor antigen); wherein the transgene is adjacent to one PAM and crRNA or flanked by two PAMs and crRNAs; and b) introducing the transgene and the RNP complex into the cell; wherein the transgene is introduced into the cell via infection with the Adeno-associated virus (AAV) into a target cell; wherein in the ribonucleoprotein (RNP) complex hybridizes to an cuts a target sequence within the genomic DNA of the cell, and the cell's DNA repair enzymes insert the transgene into the host genome at the target sequence (for example by non-homologous end joining), thereby creating a modified cell.

Also disclosed herein are methods of genetically modifying a cell of any preceding aspect, wherein the primary cells are incubated for 4 days in the presence of IL-2 and/or irradiated feeder cells prior to infection and/or electroporation.

Also disclosed herein are methods of genetically modifying a cell of any preceding aspect, further comprising expanding the modified cells with irradiated mbIL-21 expressing feeder cells following infection and/or electroporation.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 2 shows a schematic of the CRISPR/Cas9 containing plasmid.

Figures 3A, 3B:
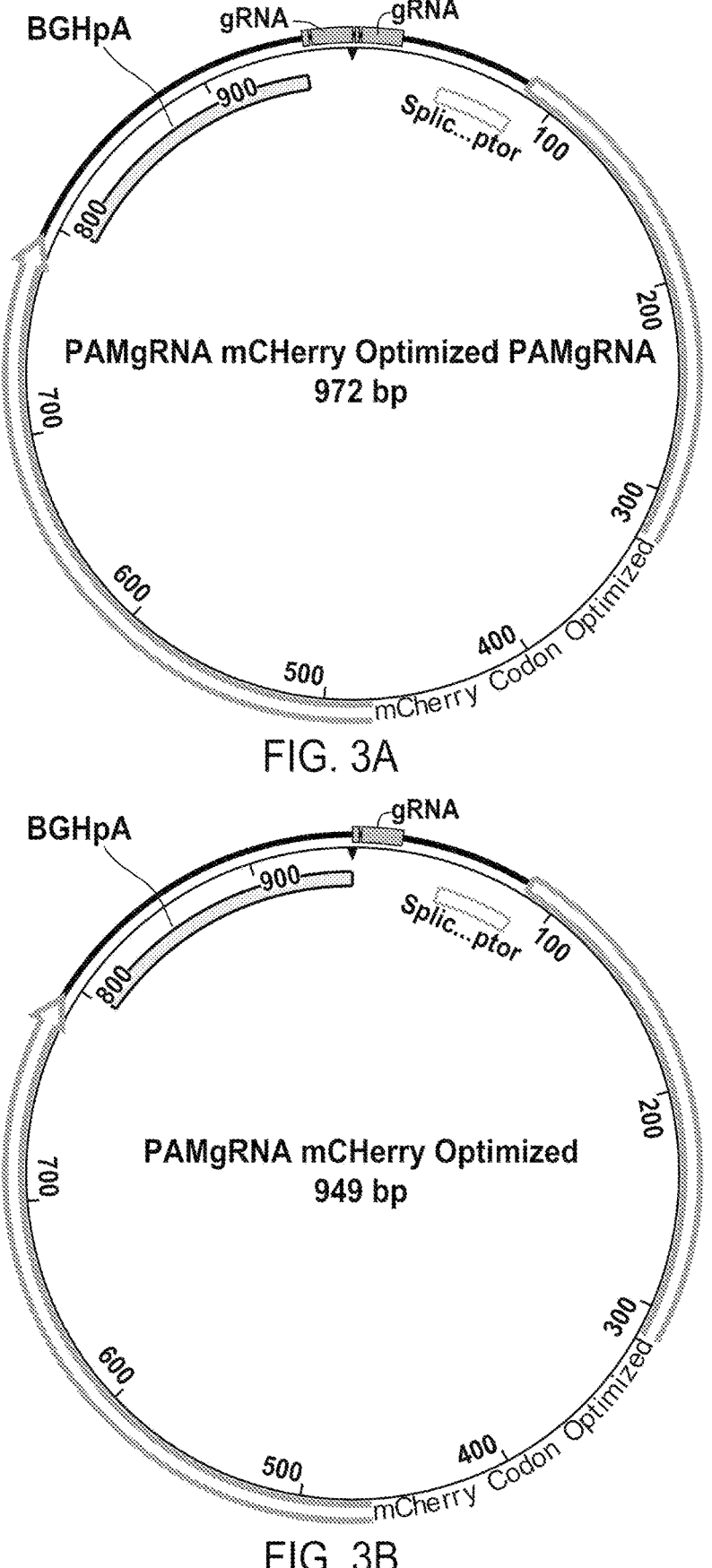

FIGS. 3A and 3B show a schematic of the plasmids for the transgene used in non-homologous end joining methods such as HITI or CRISPaint referred to herein as plasmids 9 and 10 (3B) which have a single PAM+crRNA and plasmids 11 and 12 (3A) which add a second PAM+crRNA. It should be noted that the figure shows gRNA which is understood to comprise a PAM and a crRNA.

Figure 4A:
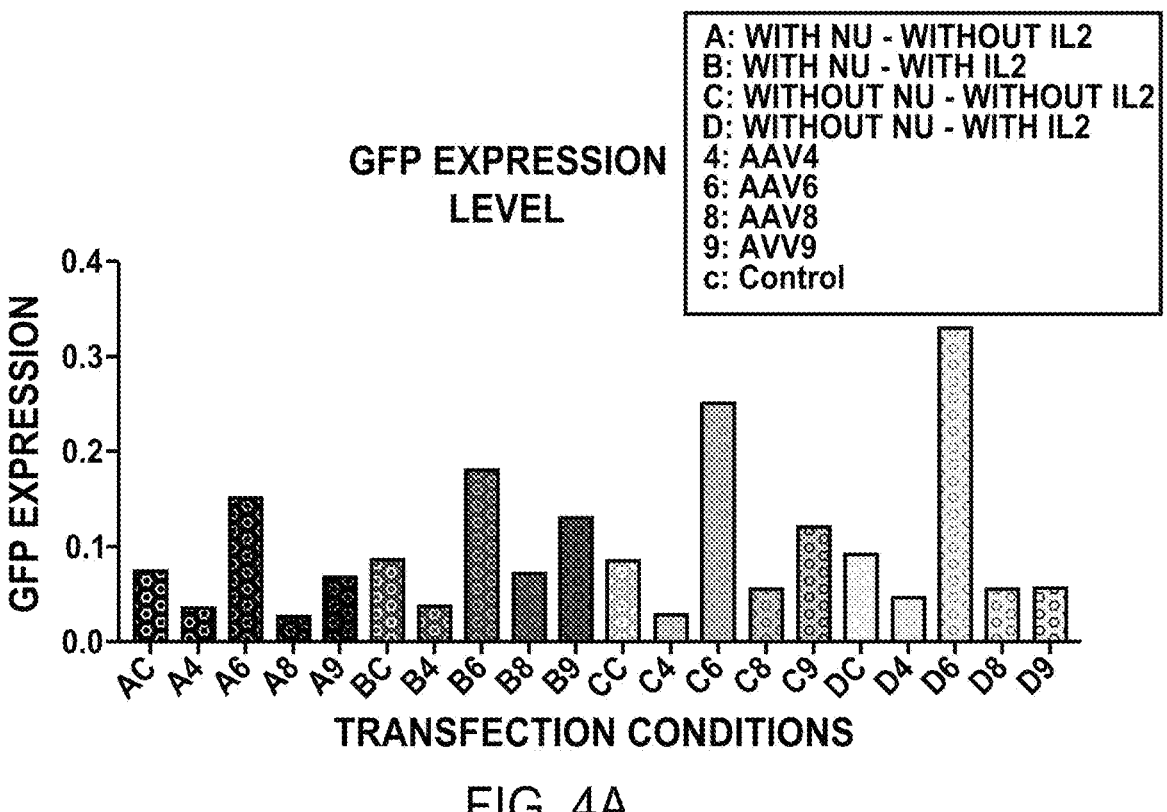
Figure 4B:
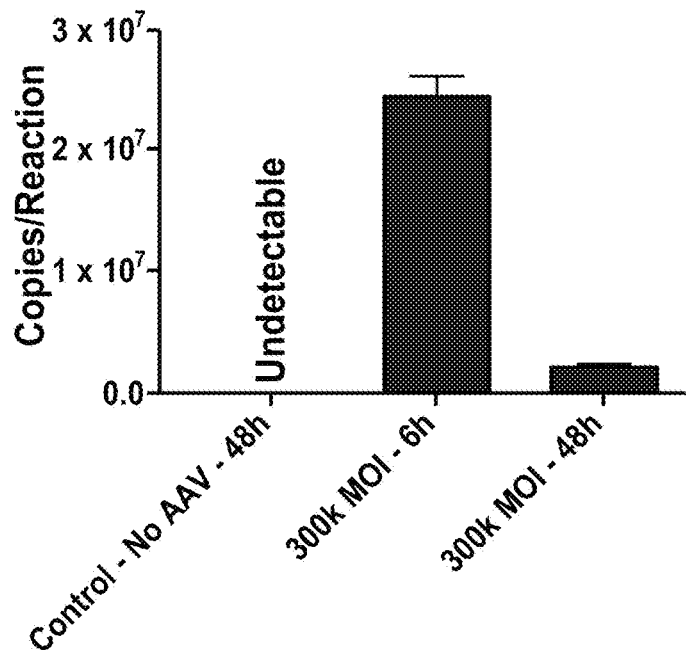

FIGS. 4A and 4B show the determination of the AAV serotype for transfecting NK cells. FIG. 4A shows the expression of GFP for various AAV serotypes under differing transfection conditions. FIG. 4B shows the copy number of AAV 6 genomic DNA in NK cells.

Figure 5B:
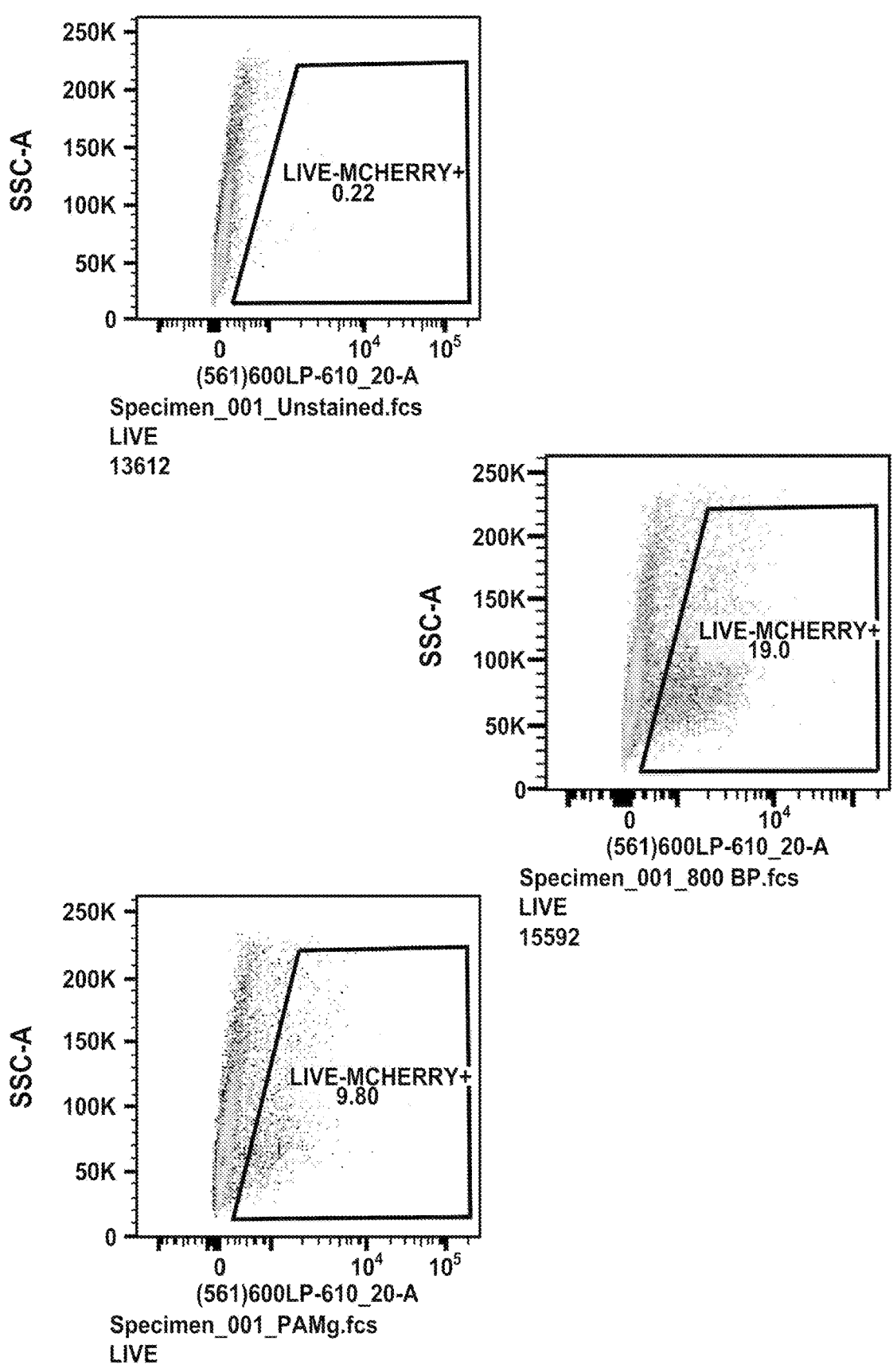
Figure 5C:
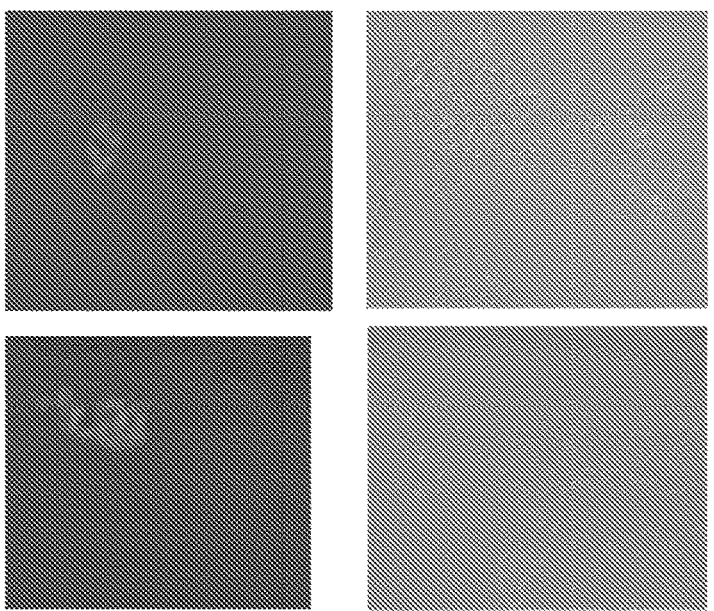

FIGS. 5A, 5B, and 5C show mCherry reporter gene integration in to AAVS1 locus of HEK293 cells was evaluated using PCR (5A). Forward and reverse primers for the amplification of mCherry1 (forward primer is SEQ ID NO: 2 and reverse primer is SEQ ID NO: 3) and mCherry2 (forward primer is SEQ ID NO: 4 and reverse primer is SEQ ID NO: 5) are shown. Also shown is that the stable gene expression of mCherry was studied using flow cytometry (5B) and florescent microscopy (5C). *The results represent 2 out of 12 designed AAV constructs. gRNA used: GGGGC-CACTAGGGACAGGAT (SEQ ID NO: 1).

Figure 6A:
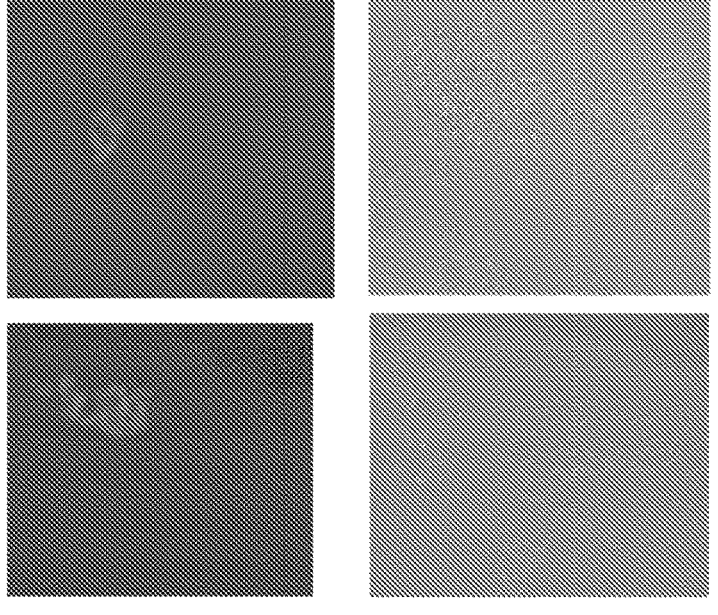

FIGS. 6A and 6B show mCherry reporter gene integration in to AAVS1 locus of human primary NK cells was evaluated using PCR (6A). The stable gene expression of mCherry post expansion was studied using flow cytometry (6B). *The results represent 2 out of 12 designed AAV constructs.

Figures 7A, 7B:
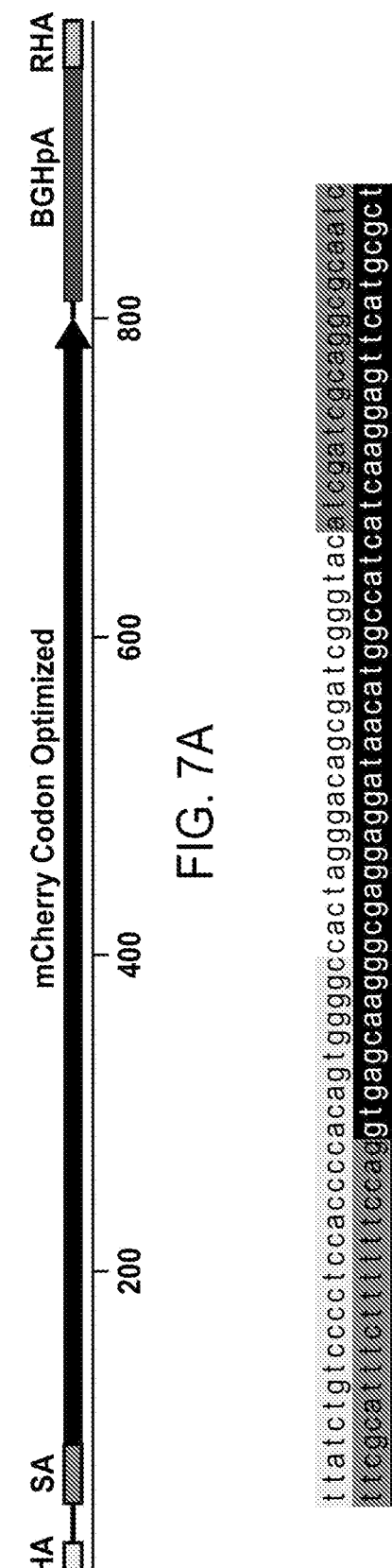
Figures 7C, 7D:
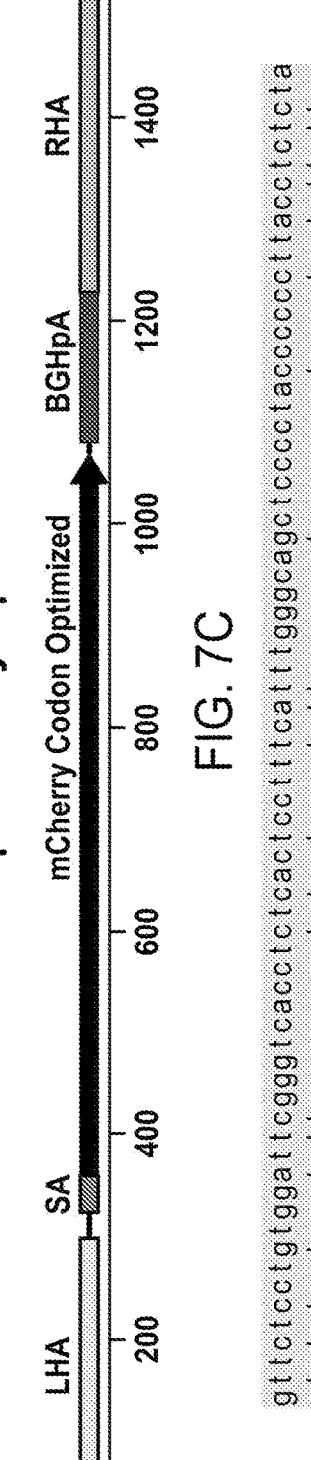
Figures 7E, 7F:
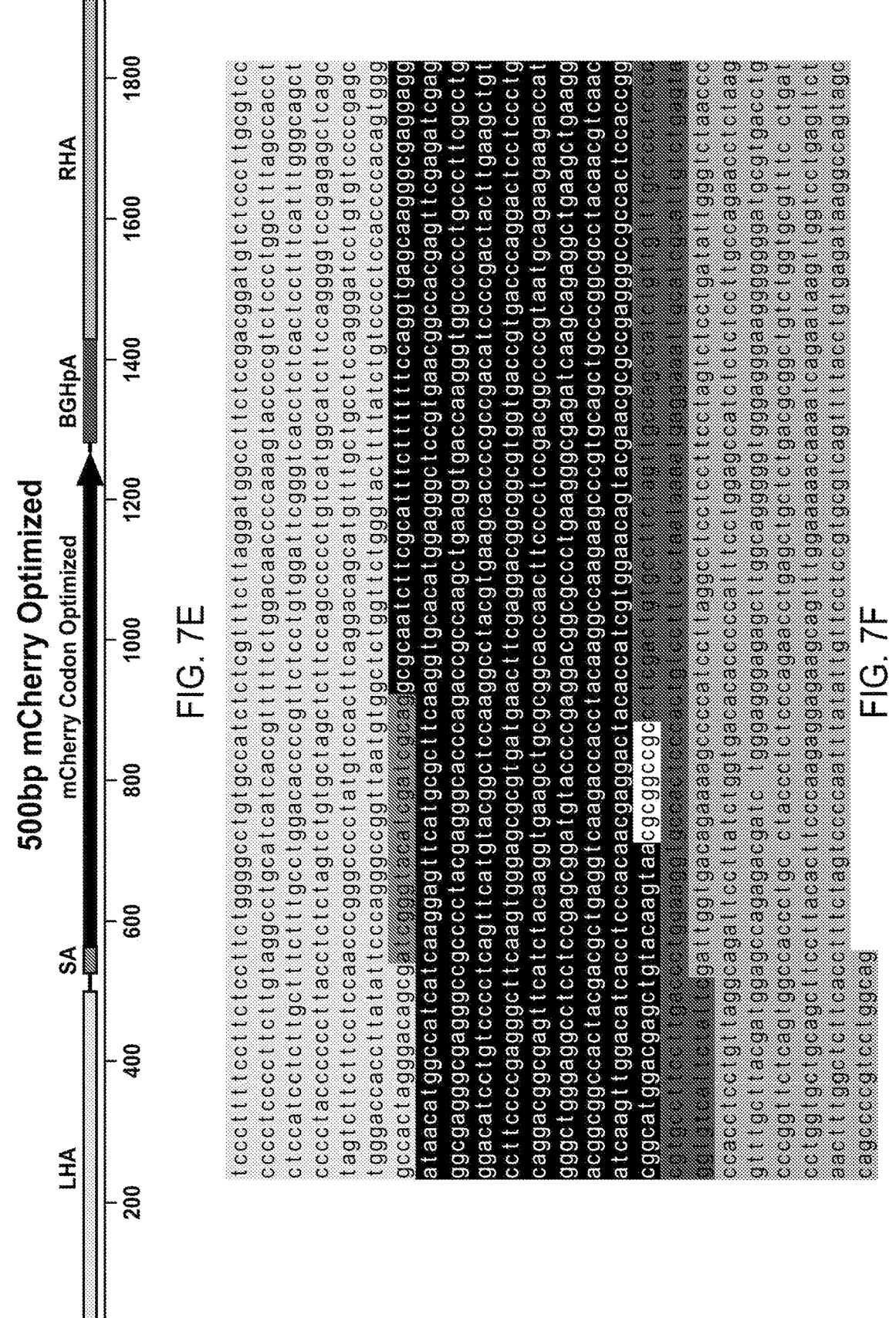
Figures 7G, 7H:
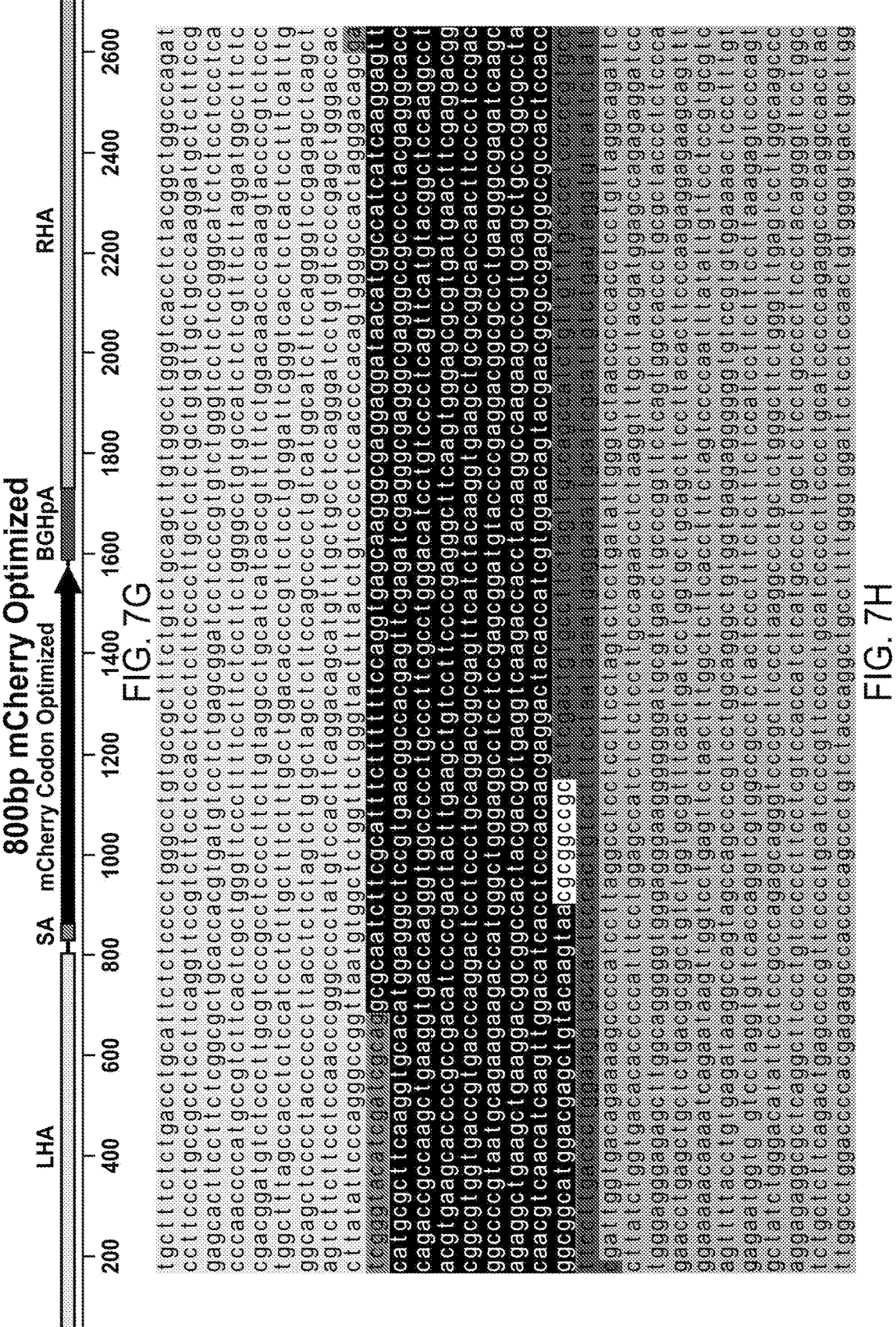

FIGS. 7A, 7B, 7C, 7D, 7E, 7F, 7G, and 7H show a schematic of the mCherry transgene containing plasmids 1, 2, 3, 4, 5, 6, 7, and 8 show the relative location of the left homology arm (LHA), splice acceptor, transgene, polyadenylation terminator, and right homology arm (RHA); and the corresponding sequence for the entire construct. FIGS. 7A and 7B show the schematic and sequence (SEQ ID NO: 13) for the 30 bp homology arm plasmid 1 and 2. FIGS. 7C and 7D show the schematic and sequence (SEQ ID NO: 14) for the 300 bp homology arm plasmid 3 and 4. FIGS. 7E and 7F show the schematic and sequence (SEQ ID NO: 15) for the 500 bp homology arm plasmid 5 and 6. FIGS. 7G and 7H show the schematic and sequence (SEQ ID NO: 16) for the

4

800 bp homology arm plasmid 7 and 8 which comprises a 800 bp LHA and a 1000 bp RHA.

Figure 8:
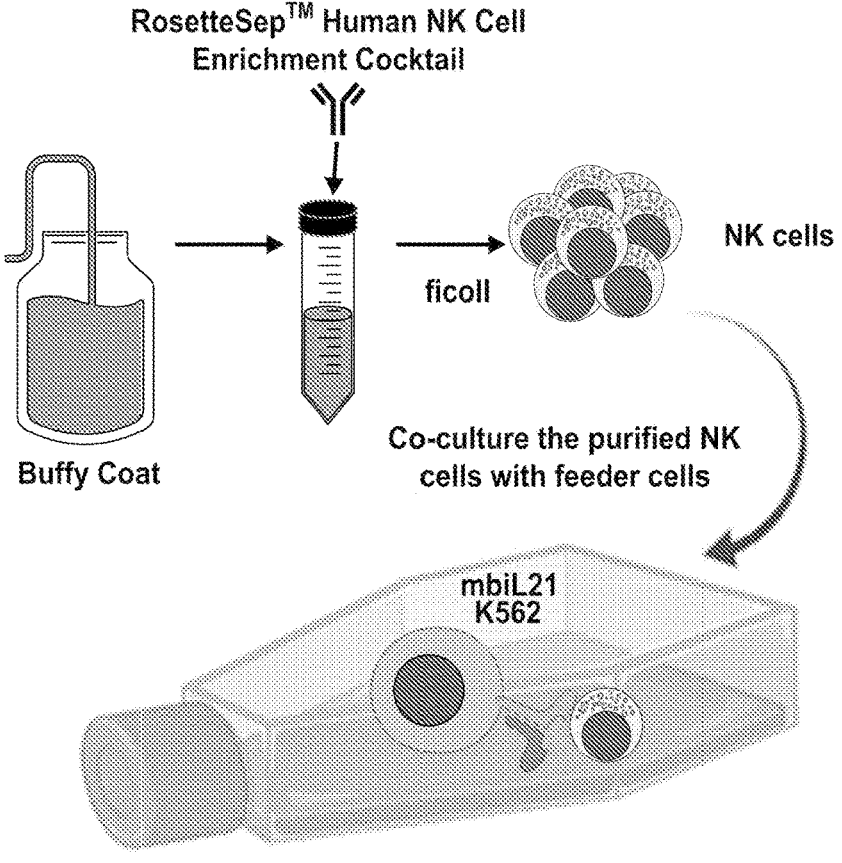

FIG. 8 shows scheme of NK isolation and expansion. Primary human NK cells were isolated from buffy coats from healthy donor and expanded using mbIL21 K562 for 7 days.

Figure 9:
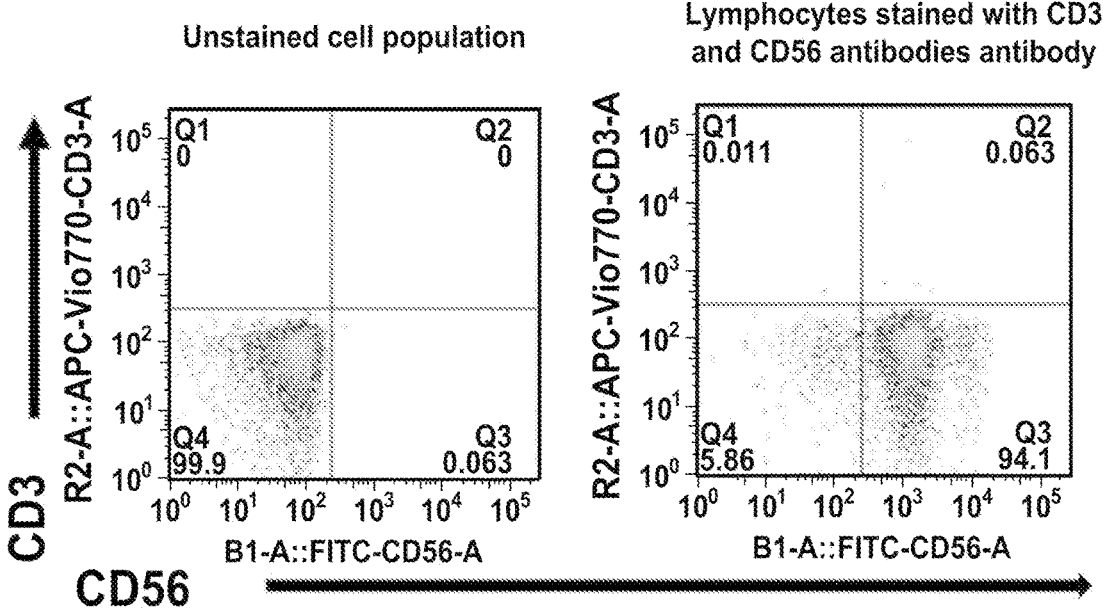

FIG. 9 shows flow cytometry result of isolated NK cells shows the purity of NK cells. The cells isolated from buffy coat were evaluated for T-cell contamination by staining for CD3 and CD56. Based on the flow cytometry results, the isolated lymphocytes were >90% CD3-negative, CD56-positive.

Figure 10:
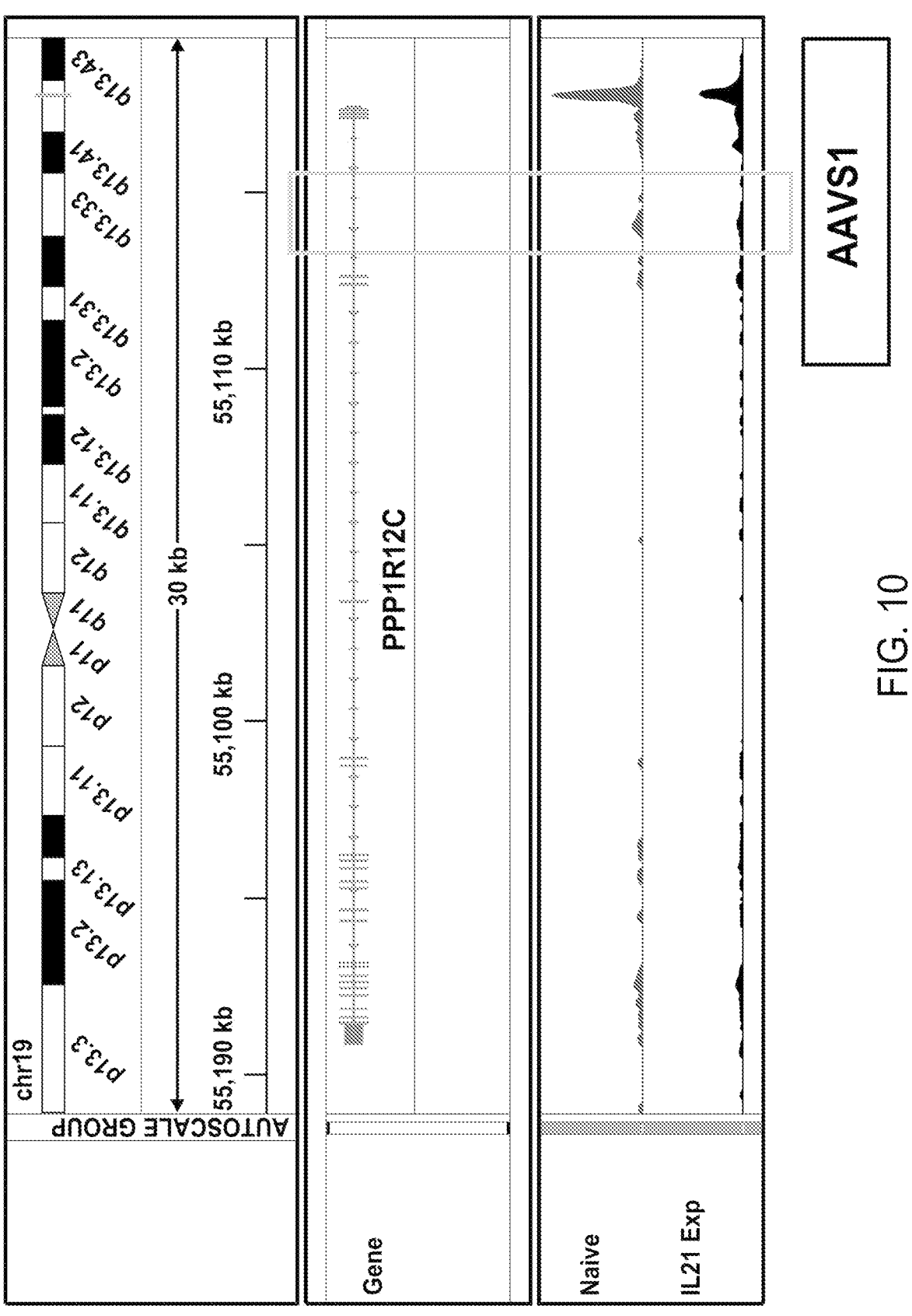

FIG. 10 shows ATAC-seq analysis shows that AAVS1 in NK cells has suitable chromatin accessibility for gene insertion. ATAC-seq peaks representing open chromatin regions. The data shows AAVS1 has similar chromatin accessibility in naïve and expanded day 7 NK cells.

FIG. 11 shows production and electroporation of Cas9/RNP to target the gene of interest in human primary NK cells. To make the gRNA, pre-transcribed crRNA and Tracer-RNA were annealed at 95 C for 5 minutes. Then pre-translated Cas9 endonuclease protein was mixed with gRNA at room temperature for 10 minutes. The Cas9/RNP and electroporation enhancer were added to NK cells. The mix then was transferred into Lonza4D nucleofection cuvette. The cells were electroporated with EN-138 program using Lonza 4D.

Figure 12:
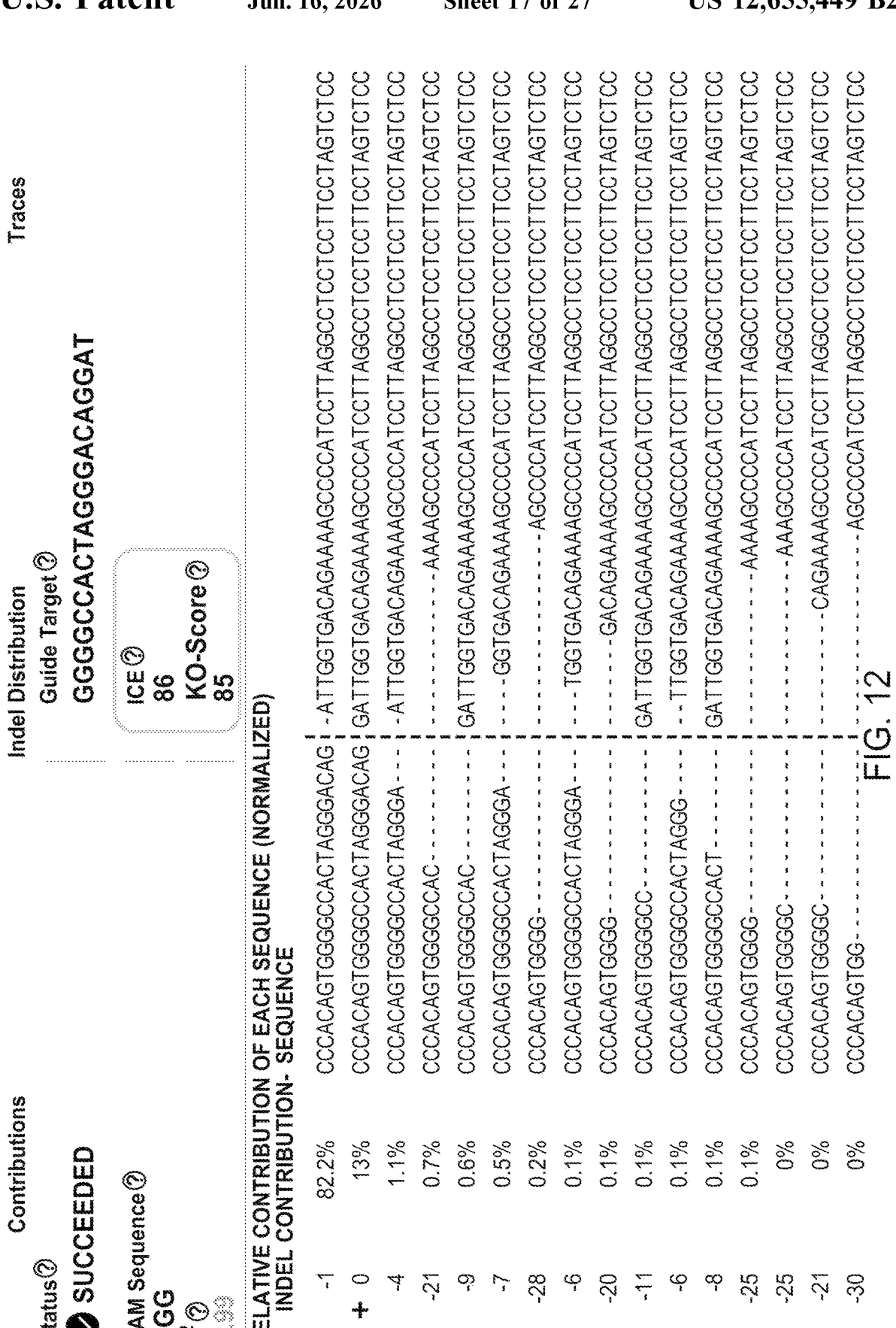

FIG. 12 shows the ICE analysis shows successful gene (AAVS1) targeting in NK cells using Cas9/RNP. The ICE uses sanger sequencing data to produce quantitative analysis of CRISPR editing. Using this method, we showed that more than 85% of NK cells were successfully targeted at AAVS1 locus.

FIG. 13 shows knocking-out AAVS1 does not alter NK cells cytotoxicity. Calcein-AM cytotoxicity assay showed no difference in NK cell-mediated killing against AML cell line by AAVS1-KO and wildtype NK cells. This demonstrates the safety of targeting AAVS1 locus in NK cells.

Figure 14:
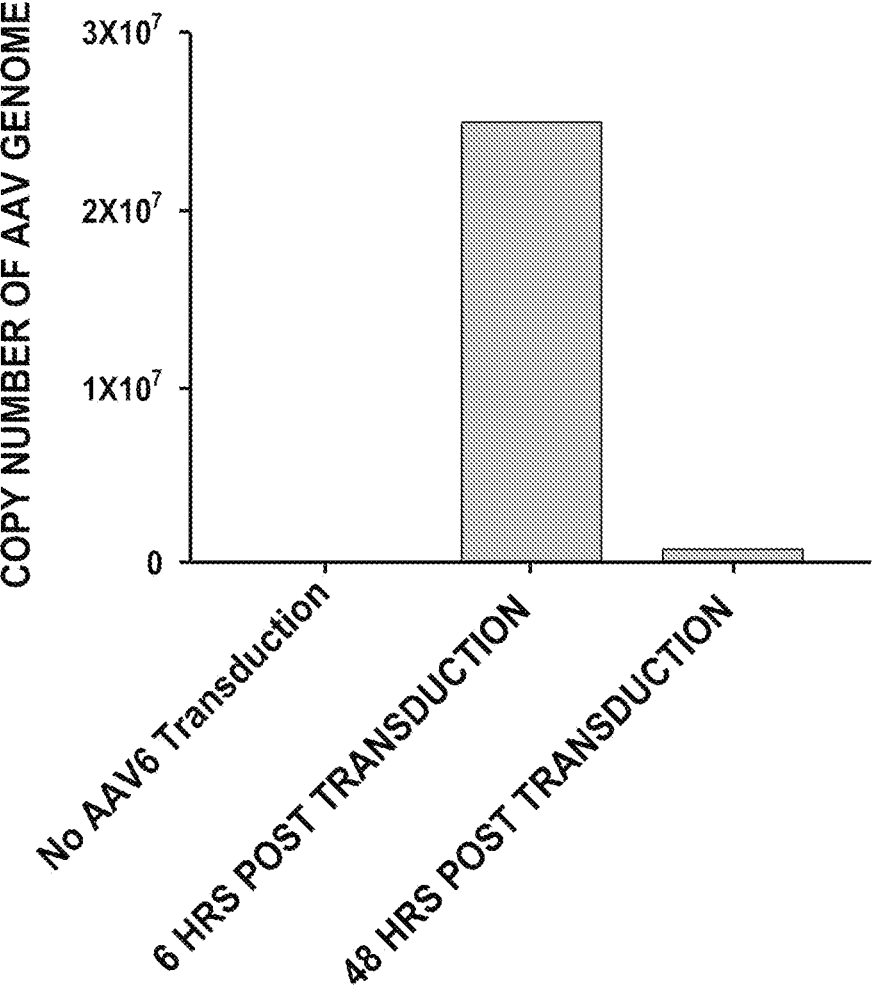

FIG. 14 shows identifying the best serotype of AAV to transduce human primary NK cells. Among 4 different serotypes of AAVs, only NK cells that were transduced with AAV6 showed expression of GFP (upper panel). AAV6 viral genome could be detected after 48 hours post transduction of NK cells at MOI of 300K (lower panel).

Figure 15:
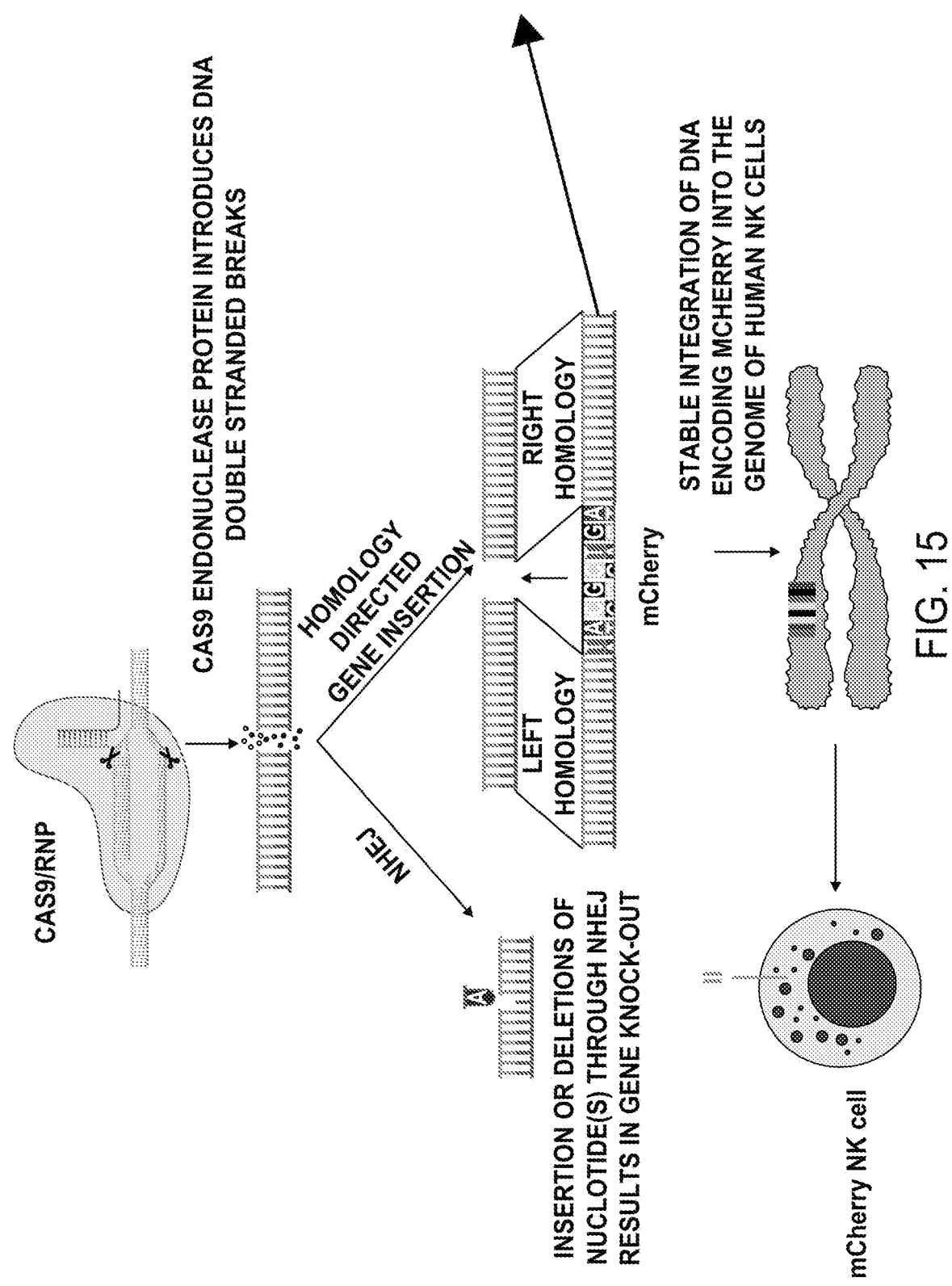
Figure 15:
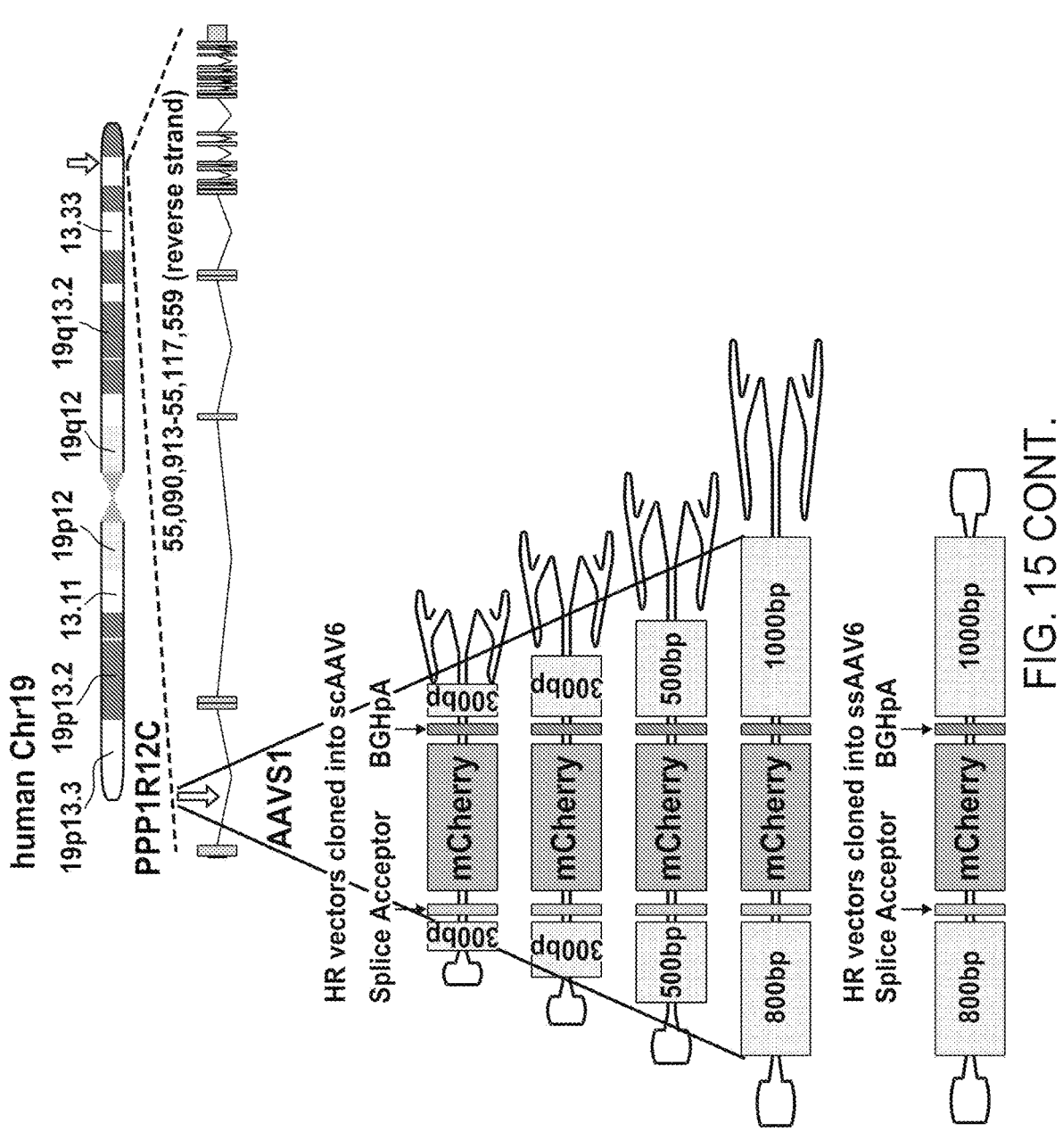

FIG. 15 shows HR-directed gene insertion requires optimal length of HAs. Non-Homologues End Joining (NHEJ) DNA repair machinery is activated following Cas9 DSB which results in gene knock-out. The Homology Repair (HR) DNA repair machinery is the pathway which its activation results in gene insertion in presence of a DNA template with optimum homology arms for Cas9-targeting site (AAVS1). We designed 30 bp, 300 bp, 500 bp and 800 bp of HA for the left HA and 30 bp, 300 bp, 500 bp and 1000 bp for the right HA. The HR templates were cloned within ITRs of ssAAV6 or scAAV6 vectors.

Figure 16A:
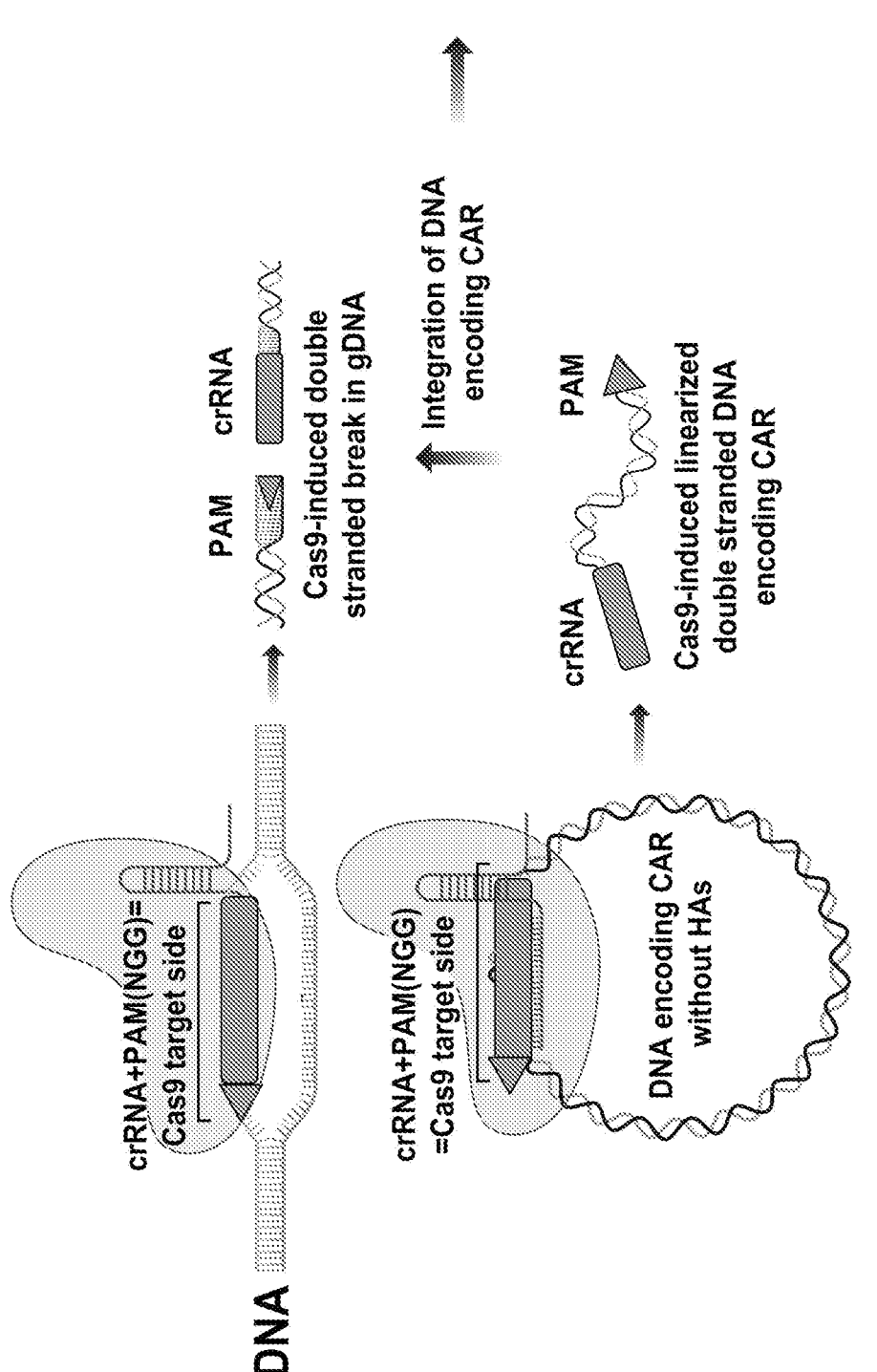
Figure 16A:
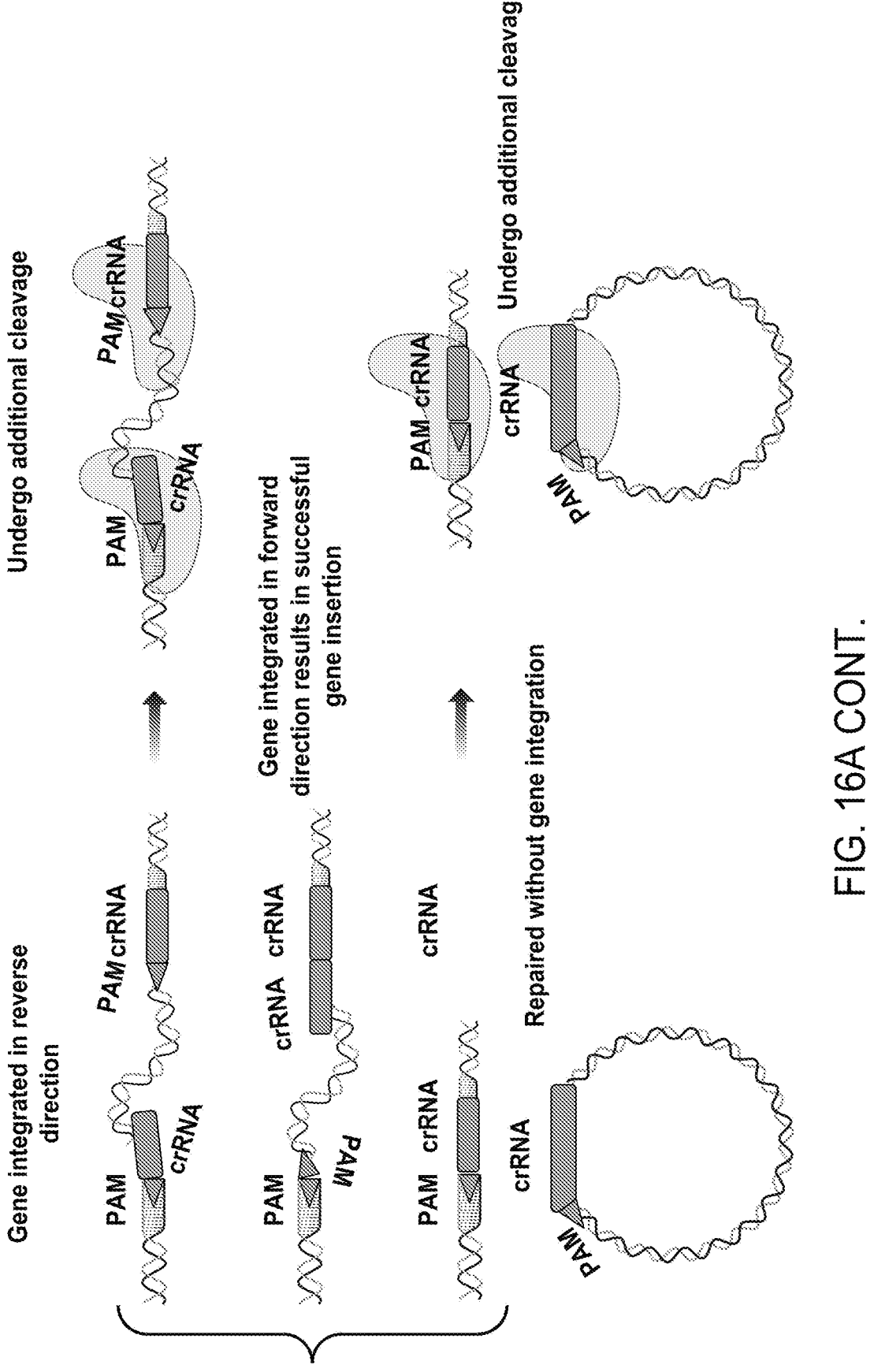
Figures 16B, 17:
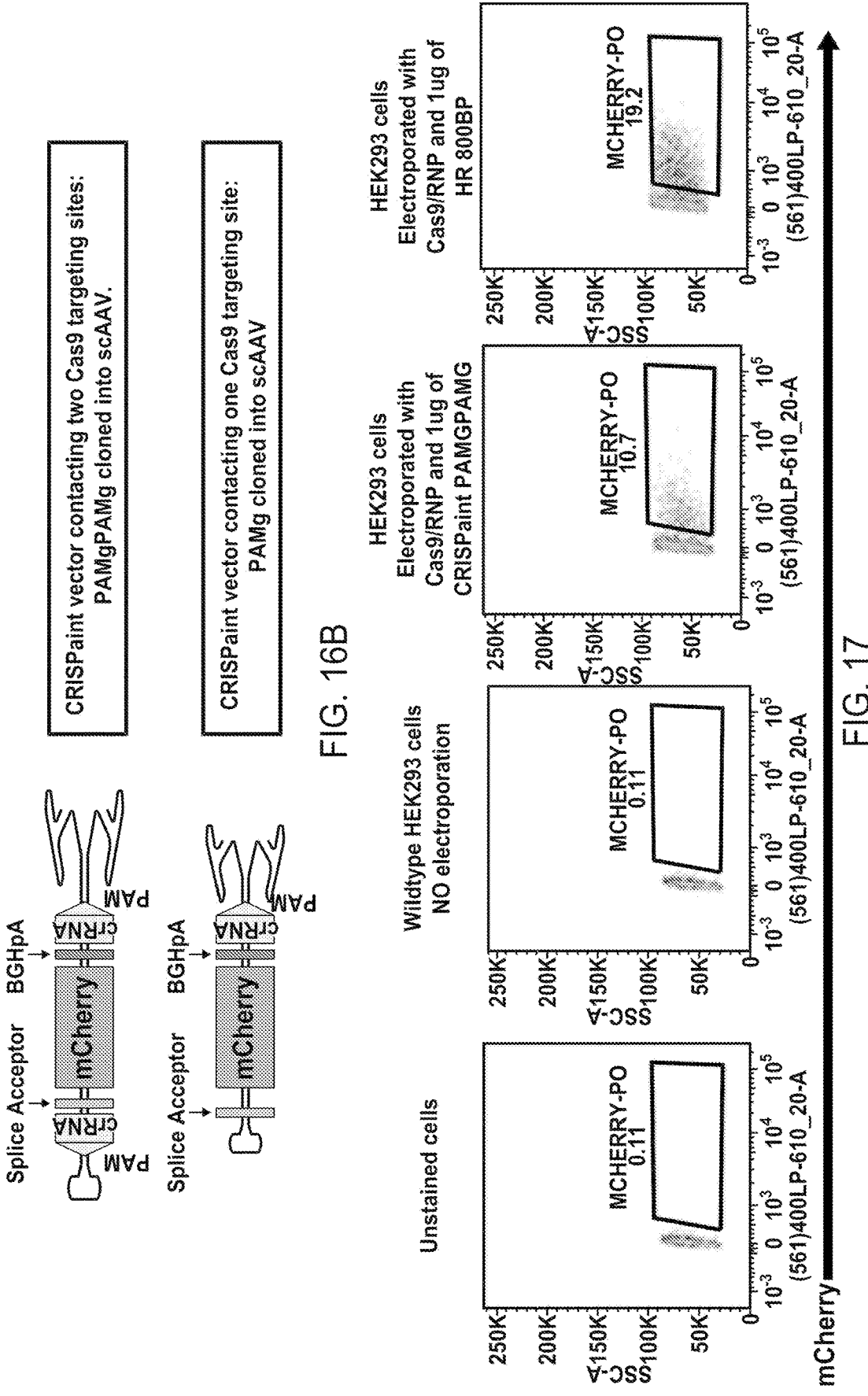

FIGS. 16A and 16B show gene integration through CRISPaint approach does not require HA for flanking region of Cas9-targeting site. For non-homologues gene insertion through CRISPaint approach (FIG. 15A), a single (PAMg) or double (PAMgPAMg) AAVS1 targeting sites (crRNA+PAM sequences) were included within ITRs. The CRISPaint helps to overcome the time-consuming process of designing HAs for HR-gene insertion (FIG. 15B).

FIG. 17 shows flow cytometry results showed successful transgene expression in HEK293 cells. Electroporation of 1 µg of DNA-encoding mCherry into HEK293 cells to assay the accuracy of the vectors showed successful gene expression. Flow cytometry showed the stable expression of mCherry.

Figures 18, 19:
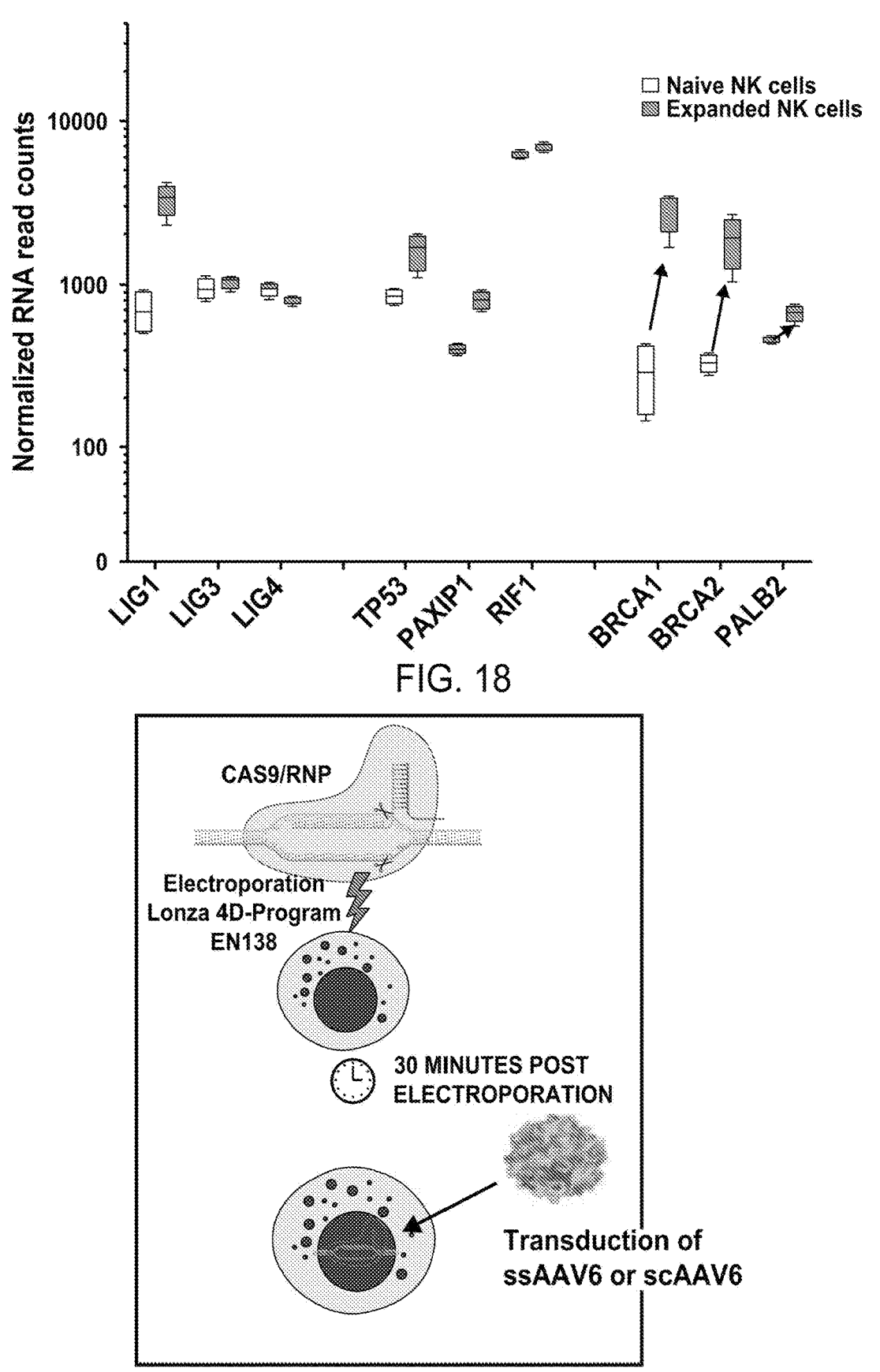

FIG. 18 show studying the expression level of HR and CRISPaint regulating enzymes in naïve and expanded NK cells. HR related enzymes were upregulated in day-7 expanded NK cells in comparison to naïve NK cells. There is no difference of non-homologues related enzyme LIG4 between naïve and expanded NK cells. This data shows that day 7 expanded NK-cells have potential optimal condition for electroporation and transduction with AAV6 for directed gene insertion through both HR and CRISPaint.

FIG. 19 shows combination of the electroporation of Cas9/RNP and transduction of AAV6 for gene insertion. 500K, 300K or 150K MOI of ssAAV6 or scAAV6 of HR and CRISPaint viruses delivering DNA-encoding mCherry were used to transduce the day 7 expanded NK cells which were electroporated with Cas9/RNP.

Figure 20:
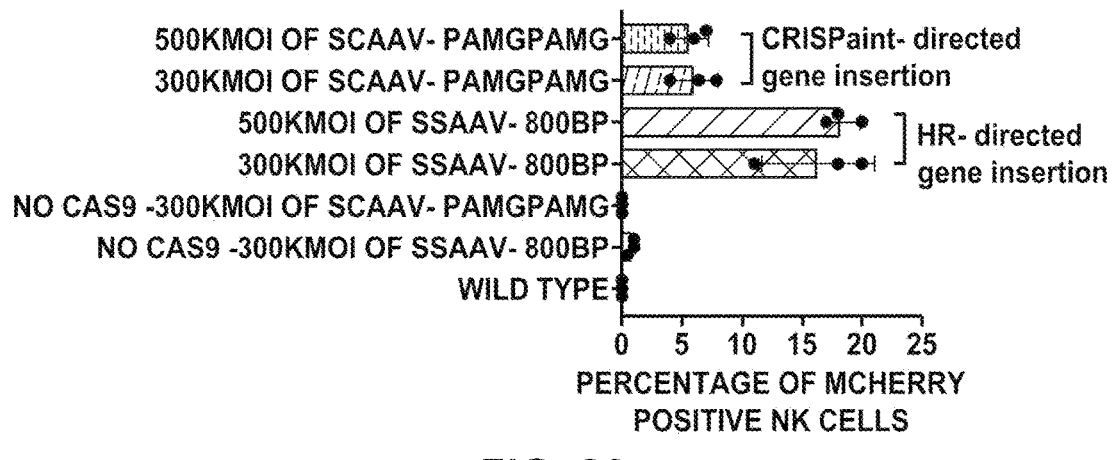

FIG. 20 shows flow cytometry results showed stable mCherry expression in CRISPR modified NK cells transduced with higher MOI of AAV6. We did not see any significant difference in the percentage of mCherry positive NK cells between the cells transduced with 500K MOI or 300K MOI of ssAAV delivering HR-800 bp or scAAV delivering CRISPaint PAMgPAMg. Therefore, for the rest of the experiments we used 300K MOI and 150K MOI of AAV6.

Figure 21:
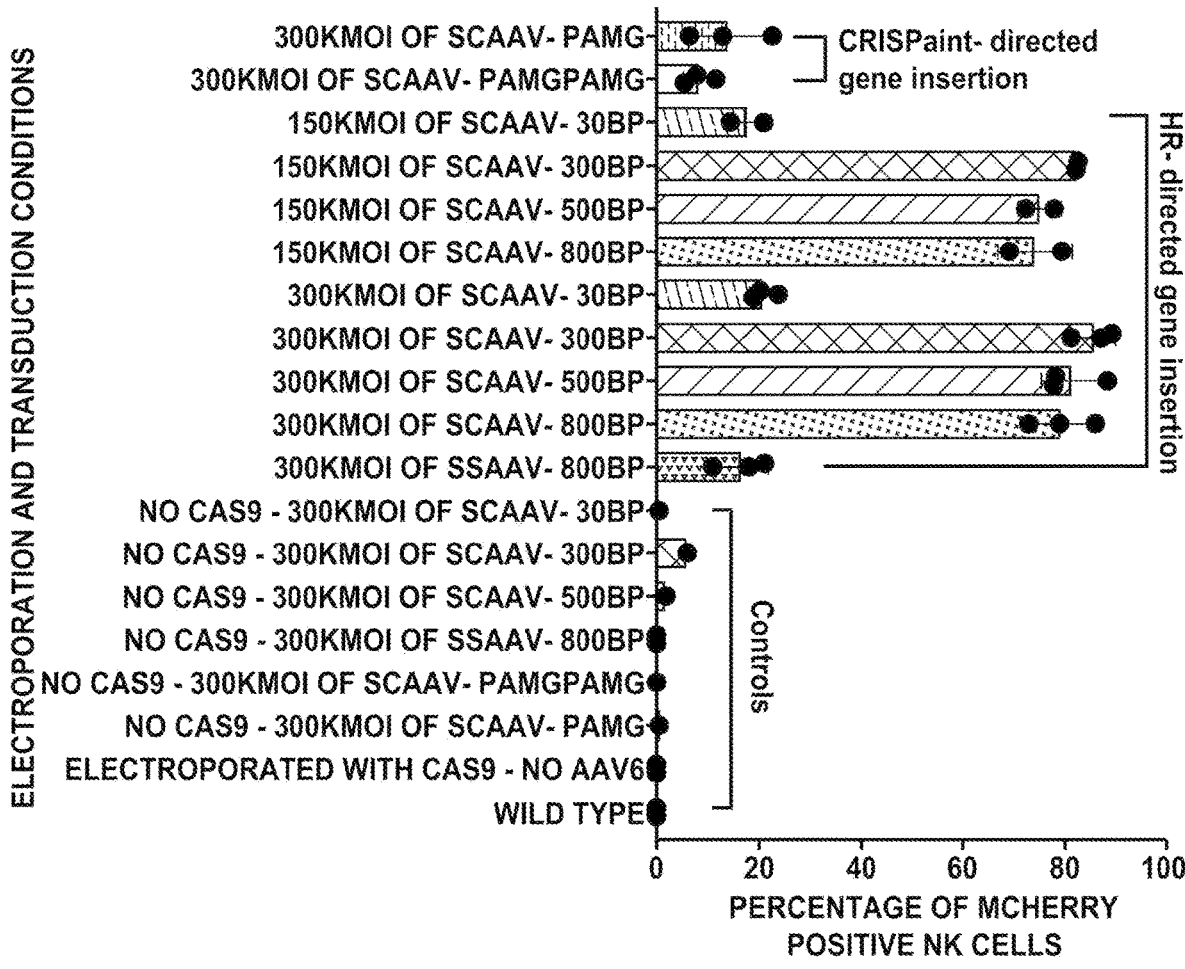

FIG. 21 shows flow cytometry results of CRISPR modified primary NK cells demonstrated highly efficient transgene expression. We electroporated NK cells with Cas9/RNP and transduced with 300K MOI or 150K MOI of ssAAV or scAAV6 delivering HR or CRISPaint DNA template. Six days post CRISPR modification, flow cytometry results show that, delivering DNA encoding mCherry with minimum optimal homology arm lengths of 300 bp for the flanking region of the Cas9-targeting site using scAAV6 results in highly efficient gene insertion in primary NK cells. larger HA including 500 bp and 800-1000 bp for smaller transgenes also can be utilized for gene insertion into NK cells. We also show that for the large transgenes 30 bp of HA also can be used for gene insertion. Additionally, we demonstrate that CRISPaint is applicable approach for gene insertion into human primary NK cells.

Figure 22:
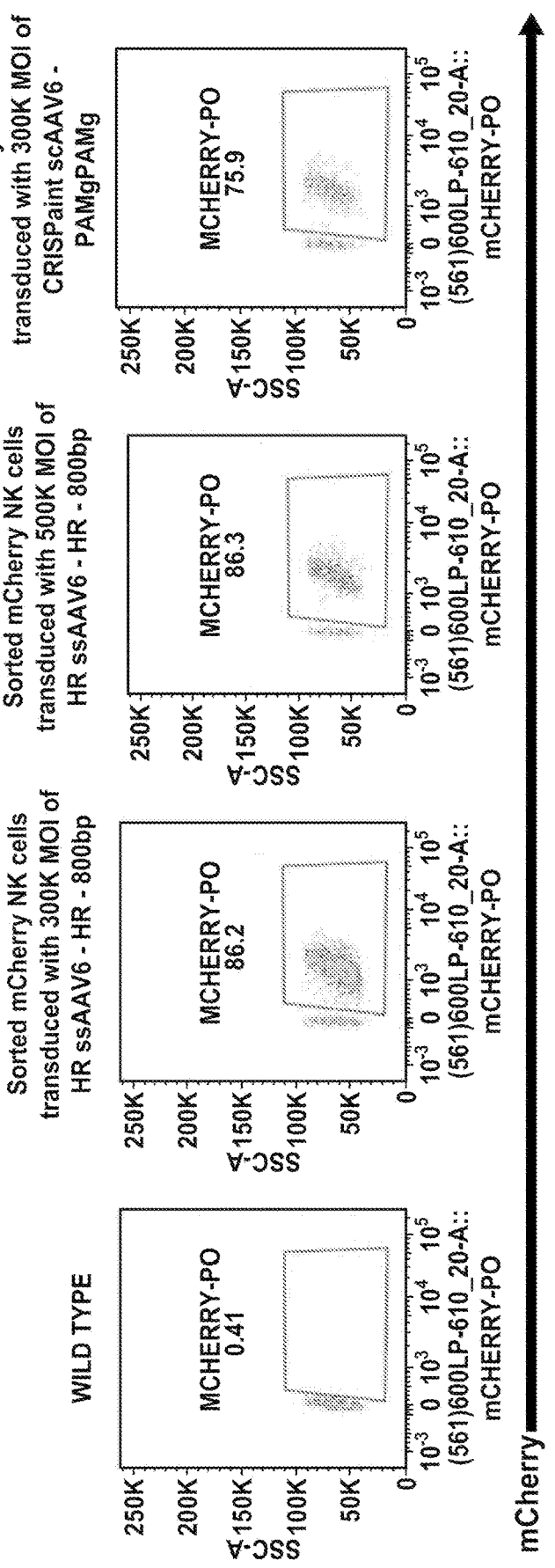

FIG. 22 shows mCherry positive NK cells can be expanded on mb-IL21 expressing feeder cells. The mCherry NK cells which were generated with ssAAV6-HR-800 bp and scAAV6-CRISPaint-PAMgPAMg and had lower efficiency were FACS sorted and grown for 20 days using feeder cells. The flow cytometry results 20 days post sorting showed the stable and enriched mCherry expression in CRISPR modified NK cells generated via both HR and CRISPaint.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

A DNA sequence that "encodes" a particular RNA is a DNA nucleic acid sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Plasmids and Methods of Genetically Modifying Cells

In one aspect, disclosed herein are plasmids for delivering donor transgene to a cell and integrating said transgene into the cell in combination with CRISPR/Cas9.

Endonuclease/RNPs (for example, a Cas9/RNP) are comprised of three components, recombinant endonuclease protein (for example, a Cas9 endonuclease) complexed with a CRISPR loci. The endonuclease complexed to the CRISPR loci can be referred to as a CRISPR/Cas guide RNA. The CRISPR loci comprises a synthetic single-guide RNA (gRNA) comprised of a RNA that can hybridize to a target sequence complexed complementary repeat RNA (crRNA) and trans complementary repeat RNA (tracrRNA). Accordingly, the CRISPR/Cas guide RNA hybridizes to a target sequence within the genomic DNA of the cell. In some cases, the class 2 CRISPR/Cas endonuclease is a type II CRISPR/Cas endonuclease. In some cases, the class 2 CRISPR/Cas endonuclease is a Cas9 polypeptide and the corresponding CRISPR/Cas guide RNA is a Cas9 guide RNA. These Cas9/RNPs are capable of cleaving genomic targets with higher efficiency as compared to foreign DNA-dependent approaches due to their delivery as functional complexes. Additionally, rapid clearance of Cas9/RNPs from the cells can reduce the off-target effects such as induction of apoptosis.

To make the RNP complex, crRNA and tracrRNA can be mixed at a 1:1, 2:1, or 1:2 ratio of concentrations between about 50 µM and about 500 µM (for example, 50, 60, 70, 80, 90, 100, 125, 150, 175, 200, 225, 250, 275, 300, 325, 35, 375, 400, 425, 450, 475, or 50004), preferably between 100 µM and about 300 µM, most preferably about 200 µM at 95 C for about 5 min to form a crRNA:tracrRNA complex (i.e., the guide RNA). The crRNA:tracrRNA complex can then be mixed with between about 20 µM and about 50 µM (for example 21, 22, 23, 24, 25, 26, 27, 28, 29, 30, 31, 32, 33, 34, 35, 36, 37, 38, 39, 40, 41, 42, 43, 44, 45, 46, 47 48, 49, or 5004) final dilution of a Cas endonuclease (such as, for example, Cas9).

Once bound to the target sequence in the target cell, the CRISPR loci can modify the genome by introducing into the target DNA insertion or deletion of one or more base pairs, by insertion of a heterologous DNA fragment (e.g., the donor polynucleotide), by deletion of an endogenous DNA fragment, by inversion or translocation of an endogenous DNA fragment, or a combination thereof. Thus, the disclosed methods can be used to generate knock-outs, or knock-ins when combined with DNA for homologous recombination. It is shown herein that transduction via Adeno-associated viral (AAV) of Cas9/RNPs is an easy and relatively efficient method that overcomes the previous constraints of genetic modification in cells (such as, for example, T cells, B cells, macrophages, NK cells, fibroblasts, osteoblasts, hepatocytes, neuronal cells, epithelial cells, and/or muscle cells).

The CRISPR/Cas9 system has recently been shown to facilitate high levels of precise genome editing using Adeno-associated viral (AAV) vectors to serve as donor template DNA during homologous recombination (HR). However, the prior use of AAV has been limited to as due to their immune function, NK cells are resistant to viral and bacterial vectors and the induction of NK cell apoptosis by said vectors. Thus, prior to the present methods CRISPR/Cas modification of NK cells has been unsuccessful. Moreover, the maximum AAV packaging capacity of ~4.5 kilobases limits the donor size which includes Homology arms. Recommendations any transcript above 100 bp and any transgene is to have homology arms that are at least 800 bp for each arm with many systems employing asymmetric arms of 800 bp and 1000 bp for a total of 1800 bp. Thus, the AAV vector cannot deliver a transgene larger than ~2.5 kb. In one aspect, as shown in Table 1, disclosed herein are AAV CRISPR/CAS9 nucleotide delivery systems comprising a donor construct plasmid with homology arms between 30 bp and 1000 bp, including, but not limited to 30, 50, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 bp. For example, the homology arms can be symmetrical 30 bp homology arms as in plasmids 1 and 2 (FIGS. 7A and 7B), symmetrical 300 bp homology arms as in plasmids 3 and 4 (FIGS. 7C and 7D), symmetrical 500 bp homology arms as in plasmids 5 and 6 (FIGS. 7E and 7F), or asymmetrical 800 bp homology arms as in plasmids 7 and 8 comprising a 800 bp left homology arm (LHA) and a 1000 bp right homology arm (RHA) (FIGS. 7G and 7H) for homologous recombination (HR) or no homology arms (plasmids 9, 10, 11, and 12) at all for non-homologous end joining using homology-independent targeted integration (HITI) plasmids. The advantage of plasmids 1, 2, 3, 4, 5, and 6 over any previous existing plasmids is the ability to not only be used for insertions, but large transcripts. Plasmids 1, 2, 3, 4, 5, and 6 can also be used in any cell type, and have clinically approved splice acceptor (SA) (SEQ ID NO: 10) and clinically approved polyadenylation terminator (PA) (such as, for example BGH polyA terminator SEQ ID NOL 11). Plasmids 7 and 8 possess clinically approved splice acceptor (SA) and clinically approved polyadenylation terminator (PA). It is understood and herein contemplated that homology arms can be symmetrical (same length on each side) or asymmetrical (different lengths on each side) to accommodate differing transgene lengths. That is, homology arm lengths can have any combination of left homology arm (LHA) length and right homology arm (RHA) length including but not limited to LHA 30 bp (SEQ ID NO: 2) and RHA 30 bp (SEQ ID NO:

1), LHA 30 bp and RHA 100 bp, LHA 30 bp and RHA 300 bp (SEQ ID NO: 3), LHA 30 bp and RHA 500 bp (SEQ ID NO: 5), LHA 30 bp and RHA 800 bp (actually 1000 bps in plasmids 7 and 8; SEQ ID NO: 7), LHA 30 bp and RHA 1000 bp, LHA 100 bp and RHA 30 bp, LHA 100 bp and RHA 100 bp, LHA 100 bp and RHA 300 bp, LHA 100 bp and RHA 500 bp, LHA 100 bp and RHA 800 bp, LHA 100 bp and RHA 1000 bp, LHA 300 bp (SEQ ID NO: 4) and RHA 30 bp, LHA 300 bp and RHA 100 bp, LHA 300 bp and RHA 300 bp, LHA 300 bp and RHA 500 bp, LHA 300 bp and RHA 800 bp, LHA 300 bp and RHA 1000 bp, LHA 500 bp (SEQ ID NO: 6) and RHA 30 bp, LHA 500 bp and RHA 100 bp, LHA 500 bp and RHA 300 bp, LHA 500 bp and RHA 500 bp, LHA 500 bp and RHA 800 bp, LHA 500 bp and RHA 1000 bp, LHA 800 bp (SEQ ID NO: 8) and RHA 30 bp, LHA 800 bp and RHA 100 bp, LHA 800 bp and RHA 300 bp, LHA 800 bp and RHA 500 bp, LHA 800 bp and RHA 800 bp, LHA 800 bp and RHA 1000 bp, LHA 1000 bp and RHA 30 bp, LHA 1000 bp and RHA 100 bp, LHA 1000 bp and RHA 300 bp, LHA 1000 bp and RHA 500 bp, LHA 1000 bp and RHA 800 bp, and LHA 1000 bp and RHA 1000 bp.

Plasmids 9, 10, 11, and 12 differ significantly from plasmids 1-8 or any described in the art. These plasmids possess the same clinically approved SA and PA and can be used in any cell type, but are not integrated through homologously directed repair (HDR), but rather integrated via HITI, CRISPaint, or other nonhomologous end joining (NHEJ). As such, they have an advantage of integrating with higher efficiency. To aid in the identification of cleavage site to remove the transgene for integration, the plasmids comprise the protospacer adjacent motif (PAM) and crRNA (i.e., the gRNA) (SEQ ID NO: 9) to target the donor transgene integration. Plasmids 11 and 12 comprise two PAM sequences to increase the likelihood of Cas9-targeting at least one site on the donor transgene plasmid.

As shown in Table 1, the change of the homology arms and can drastically effect the ability to integrate a donor transgene as can whether the plasmid is single stranded or self-complementary.

cytes, neuronal cells, epithelial cells, and/or muscle cells). This problem is overcome herein by plasmids 2, 4, 6, 8, 10, and 12 due to the use of self-complementary (SC) (double stranded) constructs in order to decrease the time of exposure to the exogenous DNA in cells. the presently disclosed plasmids.

It is understood and herein contemplated that to target the Cas9 nuclease activity to the target site and also cleave the donor plasmid to allow for recombination of the donor transgene into the host DNA, a crispr RNA (crRNA) is used. In some cases the crRNA is combined with a tracrRNA to form guide RNA (gRNA). The disclosed plasmids use AAV integration, intron 1 of the protein phosphatase 1, regulatory subunit 12C (PPP1R12C) gene on human chromosome 19, which is referred to the AAVS1, as the target site for the integration of the transgene. This locus is a "safe harbor gene" and allows stable, long-term transgene expression in many cell types. As disruption of PPP1R12C is not associated with any known disease, the AAVS1 locus is often considered a safe-harbor for transgene targeting. Because the AAV site is being used as the target location, the CRISPR RNA (crRNA) must target said DNA. Herein, the guide RNA used in the disclosed plasmids comprises GGGGC-CACTAGGGACAGGAT (SEQ ID NO: 1) or any 10 nucleotide sense or antisense contiguous fragment thereof. While AAVS1 is used for exemplary purposes here, it is understood and herein contemplated that other "safe harbor genes" can be used with equivalent results and can be substituted for AAVS1 if more appropriate given the particular cell type being transfected or the transgene. Examples of other safe harbor genes, include but are not limited to C-C chemokine receptor type 5 (CCR5), the ROSA26 locus, and TRAC.

As noted above, the use of the AAV as a vector to deliver the disclosed CRISPR/Cas9 plasmid and any donor transgene is limited to a maximum of ~4.5 kb. It is understood and herein contemplated that one method of increasing the allowable size of the transgene is to create additional room by exchanging the Cas9 of *Streptococcus pyogenes* (SpCas9) typically used for a synthetic Cas9, or Cas9 from a

TABLE 1

Differences of the 12 novel plasmids disclosed herein as defined by homology arm length, insertion scheme and transgene construction

| | | Novel plasmid # | | | | | | | | | | | |
| | | 1 | 2 | 3 | 4 | 5 | 6 | 7 | 8 | 9 | 10 | 11 | 12 |
|---|---|---|---|---|---|---|---|---|---|---|---|---|---|
| TRANS-GENE | SIZE-BP | 30 BP-SS | 30 BP-SC | 300 SBP-S | 300 BP-SC | 500 BP-SS | 500 BP-SC | 800 BP-SS | 800 BP-SC | PAMG-HITI-SS | PAMG-HITI-SC | PAMGPAMG-HITI-SS | PAMGPAM-HITI-SC |
| MCHERRY (SEQ ID NO: 12) | 708 | Y | Y | Y | Y | Y | Y | Y | Y | Y | Y | Y | Y |
| CAR-JAK/STAT | 4300 | V | N | N | N | N | N | N | N | Y | N | Y | N |
| CAR-IL2R | 3176 | Y | Y | N | N | N | N | N | N | Y | Y | Y | Y |
| | | | | Homology directed scheme | | | | | | Homology independent targeted integration (HITI) scheme | | | |

SS = single stranded (4.5 kb total construct length)
SC = self-complementary (2.5 kb total construct length)

Additionally, despite the benefit of using the single stranded (SS) plasmids to insert the larger transgenes, SS plasmids need longer time to be folded and served as a double stranded DNA inside the cells prior to the integration which increases the DNA-sensing mechanism and cytotoxicity in some cells (such as, for example, T cells, B cells, macrophages, NK cells, fibroblasts, osteoblasts, hepatodifferent bacterial source. Substitution of the Cas9 can also be used to increase the targeting specificity so less gRNA needs to be used. Thus, for example, the Cas9 can be derived from *Staphylococcus aureus* (SaCas9), *Acidaminococcus* sp. (AsCpf1), *Lachnospiracase bacterium* (LbCpf1), *Neisseria meningitidis* (NmCas9), *Streptococcus thermophilus* (StCas9), *Campylobacter jejuni* (CjCas9), enhanced SpCas9

(eSpCas9), SpCas9-HF1, Fokl-Fused dCas9, expanded Cas9 (xCas9), and/or catalytically dead Cas9 (dCas9).

It is understood and herein contemplated that the use of a particular Cas9 can change the PAM sequence which the Cas9 endonuclease (or alternative) uses to screen for targets. As used herein, suitable PAM sequences comprises NGG (SpCas9 PAM) NNGRRT (SaCas9 PAM) NNNNGATT (NmCAs9 PAM), NNNNRYAC (CjCas9 PAM), NNA-GAAW (St), TTTV (LbCpf1 PAM and AsCpf1 PAM); TYCV (LbCpf1 PAM variant and AsCpf1 PAM variant); where N can be any nucleotide; V=A, C, or G; Y=C or T; W=A or T; and R=A or G.

In one aspect, disclosed here are methods of genetically modifying a cell comprising obtaining a ribonucleoprotein (RNP) complex comprising a class 2 CRISPR/Cas endonuclease (Cas9) complexed with a corresponding CRISPR/Cas guide RNA (gRNA) specific for a target DNA sequence in the cell and a plasmid comprising a transgene (such as, for example, a chimeric antigen receptor for a tumor antigen); wherein the transgene is flanked by homology arms; and b) introducing the transgene and the RNP complex into the cell; wherein the transgene is introduced into the cell via infection with the Adeno-associated virus (AAV) into a target cell; wherein the RNP complex hybridizes to a target sequence within the genomic DNA of the cell. In one aspect, the method can further comprise introducing the RNP complex into the cell via electroporation (such as when modifying an NK cell). In one aspect, the method can further comprise superinfecting the target cell with a second AAV virus comprising the RNP complex. In one aspect, where the transgene is sufficiently small, the same AAV can comprise both the transgene and the RNP complex. In still further aspect, the transgene and RNP complex can be encoded on the same plasmid.

It is understood and herein contemplated that the disclosed methods can be utilized with any cell type including T cells, B cells, macrophages, NK cells, fibroblasts, osteoblasts, hepatocytes, neuronal cells, epithelial cells, and/or muscle cells as well as any other cell type. Human NK cells are a particularly excellent target for the disclosed plasmids and methods of their use. NK cells are a subset of peripheral blood lymphocytes defined by the expression of CD56 or CD16 and the absence of T cell receptor (CD3). NK cells sense and kill target cells that lack major histocompatibility complex (MHC)-class I molecules. NK cell activating receptors include, among others, the natural cytotoxicity receptors (NKp30, NKp44 and NKp46), and lectin-like receptors NKG2D and DNAM-1. Their ligands are expressed on stressed, transformed, or infected cells but not on normal cells, making normal cells resistant to NK cell killing. NK cell activation is negatively regulated via inhibitory receptors, such as killer immunoglobin (Ig)-like receptors (KIRs), NKG2A/CD94, TGFβ, and leukocyte Ig-like receptor-1 (LIR-1). In one aspect, the target cells can be primary NK cells from a donor source (such as, for example, an allogeneic donor source for an adoptive transfer therapy or an autologous donor source (i.e., the ultimate recipient of the modified cells), NK cell line (including, but not limited to NK RPMI8866; HFWT, K562, and EBV-LCL), or from a source of expanded NK cells derived a primary NK cell source or NK cell line.

Prior to the transduction of the cells (such as, for example, T cells, B cells, macrophages, NK cells, fibroblasts, osteoblasts, hepatocytes, neuronal cells, epithelial cells, and/or muscle cells), the cell can be incubated in a media suitable for the propagation of the to cells. It is understood and herein contemplated that the culturing conditions can comprise the addition of cytokines, antibodies, and/or feeder cells. Thus, in one aspect, disclosed herein are methods of genetically modifying a cell (such as, for example, a T cell, B cell, macrophage, NK cell, fibroblast, osteoblast, hepatocyte, neuronal cell, epithelial cell, and/or muscle cell), further comprising incubating the cells for 1, 2, 3, 4, 5, 6, 7, 8 9, 10, 11, 12, 13, or 14 days prior to transducing the cells in media that supports the propagation of cells; wherein the media further comprises cytokines, antibodies, and/or feeder cells. For example, the media can comprise IL-2, IL-12, IL-15, IL-18, and/or IL-21. In one aspect, the media can also comprise anti-CD3 antibody. In one aspect, the feeder cells can be purified from feeder cells that stimulate cells. For example, NK cell stimulating feeder cells for use in the claimed invention, disclosed herein can be either irradiated autologous or allogeneic peripheral blood mononuclear cells (PBMCs) or nonirradiated autologous or PBMCs; RPMI8866; HFWT, K562; K562 cells transfected with membrane bound IL-15, and 41BBL, or IL-21 or any combination thereof; or EBV-LCL. In some aspects, the feeder cells provided in combination with a solution of IL-21, IL-15, and/or 41BBL. Feeder cells can be seeded in the culture of cells at a 1:2, 1:1, or 2:1 ratio. It is understood and herein contemplated that the period of culturing can be between 1 and 14 days post AAV infection (i.e., 1, 2, 3, 4, 5, 6, 7, 8, 9, 10, 11, 12, 13, or 14 days), preferably between 3 and 7 days, most preferably between 4 and 6 days.

It is understood and herein contemplated that the incubation conditions for primary cells and expanded cells (including, but not limited to primary and expanded T cells, NK cells, or B cells) can be different. In one aspect, the culturing of primary NK cells prior to AAV infection comprises media and cytokines (such as, for example, IL-2, IL-12, IL-15, IL-18, and/or IL-21) and/or anti-CD3 antibody for less than 5 days (for example 1, 2, 3, or 4 days). For expanded NK cells the culturing can occur in the presence of NK feeder cells (at for example, a 1:1 ratio) in addition to or in lieu of cytokines (such as, for example, IL-2, IL-12, IL-15, IL-18, and/or IL-21) and/or anti-CD3 antibody. Culturing of expanded NK cells can occur for 1, 2, 3, 4, 5, 6, 7, 8, 9, or 10 days prior to transduction. Thus, in one aspect, disclosed herein are methods of genetically modifying a cell (such as for example, a T cell, B cell, macrophage, NK cell, fibroblast, neuronal cell osteoblast, hepatocyte, epithelial cell, and/or muscle cell) comprising incubating primary cells for 4 days in the presence of IL-2 prior to infection with an AAV vector and/or electroporation (when the RNP complex is introduced via electroporation) or incubating expanded cells in the presence of irradiated feeder cells for 4, 5, 6, or 7 days prior to infection with AAV and/or electroporation when the RNP complex is introduced via electroporation.

Following transduction (e.g., via AAV infection or electroporation) of the cell (such as, for example, a T cell, B cell, macrophage, NK cell, fibroblast, osteoblast, hepatocyte, neuronal cell, epithelial cell, and/or muscle cell), the now modified cell can be propagated in a media comprising feeder cells that stimulate the modified cells (such as, for example, a T cell, B cell, macrophage, NK cell, fibroblast, osteoblast, hepatocyte, neuronal cell, epithelial cell, and/or muscle cell). Thus, the modified cells retain viability and proliferative potential, as they are able to be expanded post-AAV infection and/or electroporation (when the RNP complex is introduced via electroporation) using irradiated feeder cells. For example, NK cell stimulating feeder cells for use in the claimed invention, disclosed herein can be either irradiated autologous or allogeneic peripheral blood mononuclear cells (PBMCs) or nonirradiated autologous or PBMCs; RPMI8866; HFWT, K562; K562 cells transfected with membrane bound IL-15, and 41BBL, or IL-21 or any combination thereof; or EBV-LCL. In some aspects, the NK cell feeder cells provided in combination with a solution of IL-21, IL-15, and/or 41BBL. Feeder cells can be seeded in the culture of NK cells at a 1:2, 1:1, or 2:1 ratio. The It is understood and herein contemplated that the period of culturing can be between 1 and 14 days post infection and/or electroporation (i.e., 1, 2, 3, 4, 5, 6, 7, 8, 9, 10, 11, 12, 13, or 14 days), preferably between 3 and 7 days, most preferably between 4 and 6 days. In some aspect, the media for culturing the modified NK cells can further comprise cytokines such as, for example, IL-2, IL-12, IL-15, IL-18, and/or IL-21.

In one aspect, it is understood and herein contemplated that the disclosed plasmids can be used to modify cells useful in the treatment of a cancer. Cancer immunotherapy has been advanced in recent years; genetically-modified chimeric antigen receptor (CAR) T cells are an excellent example of engineered immune cells successfully deployed in cancer immunotherapy. These cells were recently approved by the FDA for treatment against CD19+ B cell malignancies, but success has so far been limited to diseases bearing a few targetable antigens, and targeting such limited antigenic repertoires is prone to failure by immune escape. Furthermore, CAR T cells have been focused on the use of autologous T cells because of the risk of graft-versus-host disease caused by allogeneic T cells. In contrast, NK cells are able to kill tumor targets in an antigen-independent manner and do not cause GvHD, which makes them a good candidate for cancer immunotherapy. It is understood and herein contemplated that the disclosed plasmids and methods can be used to generate CAR T cells and CAR NK cells to target T cells and/or NK cells to a cancer.

As used herein "chimeric antigen receptor" refers to a chimeric receptor that targets a cancer antigen and brings to bring the cell expressing the receptor to a cancer cell expressing the target antigen. Typically, the CAR comprises a natural ligand of the tumor antigen a molecule that recognizes peptides derived from the tumor antigen presented by MHC molecules, or an antibody or fragment thereof (such as for example, a Fab', scFv, Fv) expressed on the surface of the CAR cell that targets a cancer antigen. The receptor is fused to a signaling domain (such as, for example the CD3ζ domain for T and NKG2C, NKp44, or CD3ζ domain for NK cells) via a linker. Tumor antigen targets are proteins that are produced by tumor cells that elicit an immune response, particularly B-cell, NK cell, and T-cell mediated immune responses. The selection of the antigen binding domain will depend on the particular type of cancer to be treated. Tumor antigens are well known in the art and include, for example, a glioma-associated antigen, carcinoembryonic antigen (CEA), EGFRvIII, IL-llRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin Bl, lectin-reactive AFP, Fos-related antigen 1, ADRB3, thyroglobulin, EphA2, RAGE-1, RU1, RU2, SSX2, AKAP-4, LCK, OY-TESl, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6, E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRCSD, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, p180erbB-3, c-met, nm-23H1, PSA, IL13Ra2, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

In one aspect, it is understood and herein contemplated that one goal of the disclosed methods of genetically modifying a cell is to produce a modified cell. Accordingly, disclosed herein are modified T cells, B cells, macrophages, NK cells, fibroblasts, osteoblasts, hepatocytes, neuronal cells, epithelial cells, and/or muscle cells made by the disclosed methods.

As noted throughout the present disclosure, the disclosed modified NK cells are ideally suited for use in immunotherapy such as the adoptive transfer of modified (i.e, engineered NK cells to a subject in need thereof. Thus, in one aspect, disclosed herein are methods of adoptively transferring an engineered cells to a subject in need thereof said method comprising a) obtaining a target cell (such as, for example, a T cell, B cell, macrophage, NK cell, fibroblast, osteoblast, hepatocyte, neuronal cell, epithelial cell, and/or muscle cell) to be modified; b) obtaining a ribonucleoprotein (RNP) complex comprising a class 2 CRISPR/Cas endonuclease (Cas9) complexed with a corresponding CRISPR/Cas guide RNA and an AAV vector comprising a plasmid comprising a transgene (such as, for example, a chimeric antigen receptor for a tumor antigen); wherein the transgene is flanked by homology arms; and wherein the homology arms are less than 800 bp; and c) introducing the transgene and the RNP complex into the cell; wherein the transgene is introduced into the cell via infection with the Adeno-associated virus (AAV) into a target cell; wherein the RNP complex hybridizes to a target sequence within the genomic DNA of the cell and the cell's DNA repair enzymes insert the transgene into the host genome (for example, by homologous repair) at the target sequence within the genomic DNA of the target cell thereby creating an engineered cell (such as, for example, a T cell, B cell, macrophage, NK cell, fibroblast, osteoblast, hepatocyte, neuronal cell, epithelial cell, and/or muscle cell); and d) transferring the engineered cell (such as, for example, a T cell, B cell, macrophage, NK cell, fibroblast, osteoblast, hepatocyte, neuronal cell, epithelial cell, and/or muscle cell) into the subject. In one aspect the transgene can be comprised on the same plasmid as the Cas9 endonuclease or encoded on a second plasmid in the same or different AAV vector. In one aspect, the target cell can be transduced with the RNP complex via electroporation before or concurrently with the infection of the cell with the transgene comprising AAV.

In one aspect, disclosed herein are methods of genetically modifying a cell (T cells, B cells, macrophages, NK cells, fibroblasts, osteoblasts, hepatocytes, neuronal cells, epithelial cells, and/or muscle cells, including, but not limited to primary or expanded cells) by non-homologous end joining comprising a) obtaining a ribonucleoprotein (RNP) complex comprising a class 2 CRISPR/Cas endonuclease (Cas9) complexed with a corresponding CRISPR/Cas guide RNA and an AAV vector comprising a plasmid comprising a transgene (such as, for example, a chimeric antigen receptor for a tumor antigen); wherein the transgene is adjacent to one PAM and crRNA or flanked by two PAMs and crRNAs; and b) introducing the transgene and the RNP complex into the cell; wherein the transgene is introduced into the cell via infection with the Adeno-associated virus (AAV) into a target cell; wherein in the ribonucleoprotein (RNP) complex hybridizes to an cuts a target sequence within the genomic DNA of the cell, and the cell's DNA repair enzymes insert the transgene into the host genome at the target sequence (for example by non-homologous end joining), thereby creating a modified cell.

In one aspect, the modified cells cell (such as, for example, modified T cells, B cells, macrophages, NK cells, fibroblasts, osteoblasts, hepatocytes, neuronal cells, epithelial cells, and/or muscle cells) used in the disclosed immunotherapy methods can be primary cells from a donor source (such as, for example, an allogeneic donor source for an adoptive transfer therapy or an autologous donor source (i.e., the ultimate recipient of the modified cells), a cell line (including, but not limited to NK cell lines NK RPMI8866; HFWT, K562, and EBV-LCL), or from a source of expanded cells derived a primary cell source or cell line. Because primary cells can be used, it is understood and herein contemplated that the disclosed modifications of the cell can occur ex vivo or in vitro.

Following transduction of the cells cell (such as, for example, T cells, B cells, macrophages, NK cells, fibroblasts, osteoblasts, hepatocytes, neuronal cells, epithelial cells, and/or muscle cells), the modified cells can be expanded and stimulated prior to administration of the modified (i.e., engineered) cells to the subject. For example, disclosed herein are methods of adoptively transferring immune cells to a subject in need thereof wherein the immune cell (such as, for example, a T cell, B cell, macrophage, natural killer (NK) cell, NK T cell, tumor infiltrating lymphocyte (TIM), marrow infiltrating lymphocyte (MIL), tumor infiltrating NK cell (TINK), fibroblast, osteoblast, hepatocyte, neuronal cell, epithelial cell, and/or muscle cell) is expanded with irradiated feeder cells, plasma membrane (PM) particles, or exosomes (EX) expressing membrane bound IL-21 (mbIL-21) (PM particles and EX exosomes expressing mbIL-21 are referred to herein as PM21 particles and EX21 exosomes, respectively) prior to administration to the subject. In some aspects, expansion can further comprise irradiated feeder cells, plasma membrane (PM) particles, or exosomes expressing membrane bound IL-15 (mbIL-15) and/or membrane bound 4-1BBL (mb4-1BBL) In some aspect, it is understood and herein contemplated that the stimulation and expansion of the modified (i.e, engineered) cells can occur in vivo following or concurrent with the administration of the modified cells to the subject. Accordingly disclosed herein are immunotherapy methods wherein the cells (such as, for example, T cells, B cells, macrophages, NK cells, NK T cells, TILs, MILs, TINKs, fibroblasts, osteoblasts, hepatocytes, neuronal cells, epithelial cells, and/or muscle cells) are expanded in the subject following transfer of the cells to the subject via the administration of IL-21 or PM particles with mbIL-21, exosomes with mbIL-21, and/or irradiated mbIL-21 expressing feeder cells. In some aspect, the expansion further comprises the administration of IL-15 and/or 4-1BBL or PM particles, exosomes, and/or irradiated feeder cells that express membrane bound IL-15 and/or 4-1BBL.

It is understood and herein contemplated that the disclosed modified cell (such as, for example, T cells, B cells, macrophages, NK cells, fibroblasts, osteoblasts, hepatocytes, neuronal cells, epithelial cells, and/or muscle cells and including, but not limited to the CAR NK cells and CAR T cells disclosed herein) and adoptive transfer methods of the modified cells can be effective immunotherapy against a cancer. The disclosed methods and compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

1. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000-fold excess. This type of assay can be performed at under conditions where both the limiting and non-limiting primer are for example, 10-fold or 100-fold or 1000-fold below their $k_d$, or where only one of the nucleic acid molecules is 10-fold or 100-fold or 1000-fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

2. Nucleic Acids

There are a variety of molecules disclosed herein that are nucleic acid based, including for example the nucleic acids that encode, for example TGFβR2, or any of the nucleic acids disclosed herein for making TGFRβ2 knockouts, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA*, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules involved in the signaling pathways disclosed herein, for example TGFβR2, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those of skill in the art understand how to resolve sequence discrepancies and differences and to adjust the compositions and methods relating to a particular sequence to other related sequences. Primers and/or probes can be designed for any given sequence given the information disclosed herein and known in the art.

c) Primers and Probes

Disclosed are compositions including primers and probes, which are capable of interacting with the disclosed nucleic acids, such as the TGFβR2 and/or HPRT1 as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the TGFβR2 and HPRT1 gene typically will be used to produce an amplified DNA product that contains a region of the TGFβR2 and HPRT1 gene or the complete gene. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

3. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19 (such as, for example at AAV integration site 1 (AAVS1)). Vectors which contain this site-specific integration property are preferred. AAVs used can be derived from any AAV serotype, including but not limited to AAC1, AAV2, AAV3, AAV4, AAV5, AAV6, AAV7, AAV8, AAV9, and recombinant (rAAV) such as, for example AAV-Rh74, and/or synthetic AAV (such as, for example AAV-DJ, Anc80). AAV serotypes can be selected based on cell or tissue tropism. AAV vectors for use in the disclosed compositions and methods can be single stranded (SS) or self-complementary (SC).

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically, the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

It is understood and herein contemplated that the packaging capacity of an AAV is limited. One method to overcome the loading capacity of an AAV vector is through the use of 2 vectors, wherein the transgene is split between the two plasmids and a 3' splice donor and 5' splice acceptor are used to join the two sections of transgene into a single full-length transgene. Alternatively, the two transgenes can be made with substantial overlap and homologous recombination will join the two segments into a full-length transcript.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Peptides a) Protein Variants

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

TABLE 2

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions
Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 2 and Table 3. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—, —$CH(OH)CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) —$CH$ $H_2$—S); Hann *J. Chem. Soc Perkin Trans. I* 307-314 (1982) (—$CH$—$CH$—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—$CH(OH)$ $CH_2$—); Holladay et al. *Tetrahedron. Lett* 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

6. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Also provided herein are plasmids comprising in order a left homology arm, a splice acceptor, a transgene, and a right homology arm; wherein the left and right homology arms are each 800 bp in length or less.

In one aspect, provided herein are plasmids comprising or consisting of 1 or 2 protospacer adjacent motifs (PAMs) and CRISPR RNAs (crRNAs) and a transgene; wherein the order of the encoded nucleic acid comprises a PAM, a crRNA and a transgene; and wherein when 2 PAMs and crRNAs are used, the encoded nucleic acid comprises a first PAM, a first crRNA, a transgene, a second PAM, and second gRNA.

Also provided herein a plasmid of the invention, an AAV vector of the invention or a modified cell of the invention for use as a medicament. The invention further provides a use of a plasmid of the invention, an AAV vector of the invention or a modified cell of the invention for the manufacture of a medicament. The invention also provides a plasmid of the invention, an AAV vector of the invention or a modified cell of the invention for use in the treatment of cancer. The invention further provides a use of a plasmid of the invention, an AAV vector of the invention, or a modified cell of the invention for the manufacture of a medicament for the treatment of cancer.

C. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Genetically-modified chimeric antigen receptor (CAR) T cells are an excellent example of engineered immune cells successfully deployed in cancer immunotherapy. These cells were recently approved by the FDA for treatment against CD19+ B cell malignancies, but success has so far been limited to diseases bearing a few targetable antigens. It also has several side effects which make NK cells a better alternative.

Figure 1:
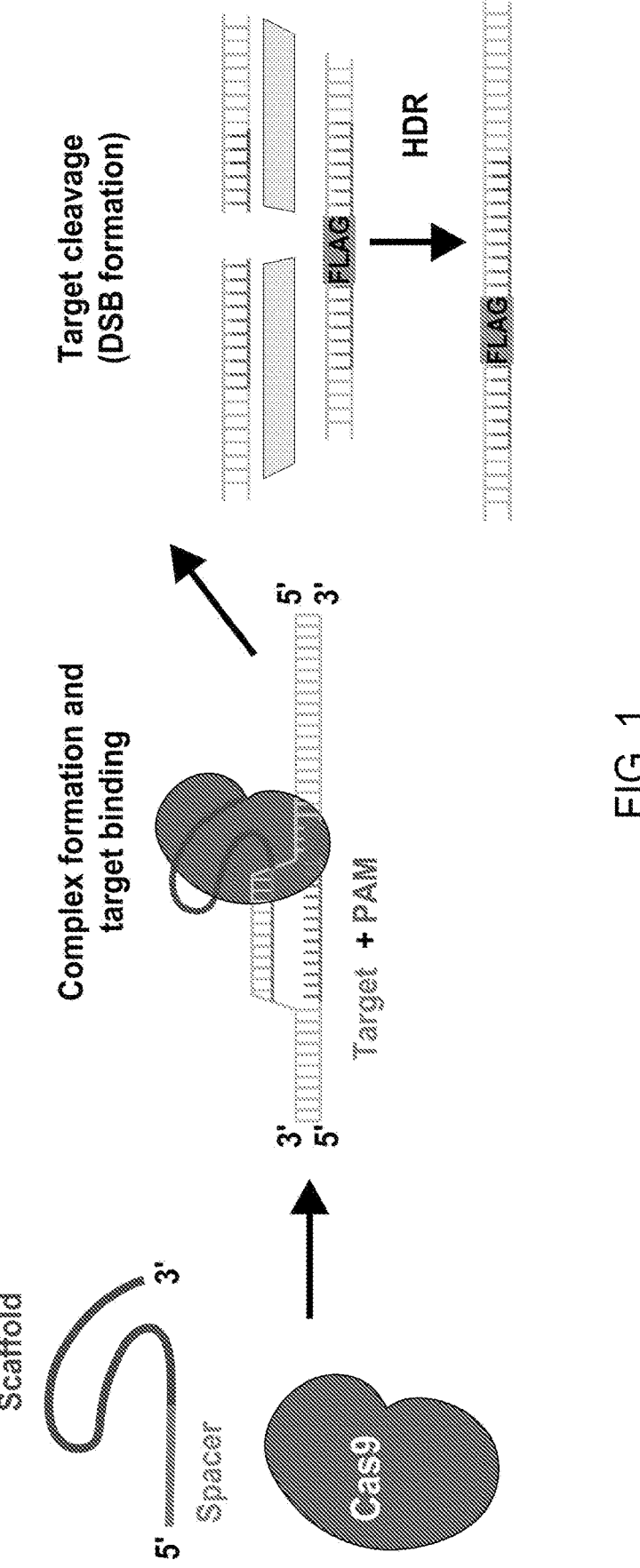
FIG. 1 shows a schematic of CRISPR/Cas 9 complex using an AAV vector for delivery of the CRISPR/Cas9 and transgene. The schematic details the action of the CRISPR/Cas9 system in integrating the transgene via homology directed repair, shows the AAVS1 target site on chromosome 19 and provides detail of the donor plasmids having homology arms of 30, 300, 500, or 800 bp.

Disclosed herein is a DNA-free technique for the genome editing of primary and expanded human cells (including NK cells) utilizing Cas9 ribonucleoprotein complexes (Cas9/RNPs) (See FIG. 1).

It has been shown that transgene delivery with naturally recombinant adeno-associated virus (rAAV) donor vectors which are non-pathogenic viruses enables site-specific gene insertion by homology directed or homology independent targeted integration (HITI, CRISPaint) (FIG. 3).

Essential sequences from the different serotypes of AAV plasmids were used to develop 12 novel plasmids to be used in a combination with Cas9/RNP (FIG. 2) for directed integration of genes of interest in to human primary cells including NK cells and HEK293 cells.

In the new methodology, the Cas9 RNP complex cleaves DNA (at AAVS1 locus), In the presence of a DNA fragment of choice (CAR-expressing DNA or reporter gene) provided by one of our 12 AAV plasmids (single-stranded or self-complementary) with 30-1000 bp homology arms between the target and the donor DNA on each side flanking the Cas9 cleavage site for HDR-guided gene insertion or the homology independent-guided insertion (by providing crRNA+

PAM sequence in the DNA template), an exogenous gene was inserted into the genome of human NK cells and HEK293 cells as a proof.

To test the system, NK cells were transfected with AAV delivered CRISPR/Cas9 plasmids and plasmids comprising transgenes. To determine the appropriate AAV serotype for infection in NK cells, various AAV serotypes comprising plasmids encoding green fluorescence protein (GFP) encoding were used to infect NK cells under various transfection conditions (FIG. 4A). It was determined that AAV6 consistently provided the greatest expression under any culture conditions. Moreover, it was shown that the infection of AAV6 was transient having approximately $2.5 \times 10^7$ copies of virus 6 h after a MOI of $3 \times 10^6$, but falling to near undetectable levels by 48 hrs post infection (4B). This is particularly important as it indicates a decreased risk of off target infection.

HEK293 Cells were next electroporated with a ribonucleoprotein (RNP) complex comprising a class 2 CRISPR/Cas endonuclease (Cas9) complexed with a corresponding CRISPR/Cas guide RNA and infected with AAV encoding and the mCherry transgene targeted to the AAVS1 locus (FIG. 5). Using PCR with primers for mCherry1 or mCherry2, integration of the mCherry in HEK293 cells was tested (5A). These results were confirmed by flow cytometry (5B) and microscopy (5C).

The experiments were next repeated using human primary NK cells (FIG. 6) showing identical results with stable expression at the AAVS1 locus using either a plasmid with 30 bp homology arms, 500 bp homology arms, or 800 bp homology arms (6A) and confirmed by flow cytometry (6B). The success of all the plasmids in integrating various size constructs is summarized in Table 1.

2. Example 2

Gene modification of NK cells using viral or non-viral vectors has been challenging due to robust foreign DNA- and RNA-sensing mechanisms, and hence limits the efficiency of gene delivery methods into NK cells. To overcome this limitation, a new method was developed for electroporating Cas9/ribonucleoprotein complexes (Cas9/RNP) directly into human primary NK cells. This method introduces a double-strand break (DSB) in the genome of NK cells, which results in successful gene knock-out and enhanced antitumor activity. Cas9 protein is preferable to mRNA delivery due to its fast action and clearance. After this initial success in gene silencing, the method was further developed for gene insertion. Following the action of Cas9 of introducing a DSB, two independent pathways can be utilized to repair the damage, known as homologous recombination (HR) and homology-independent repair. In the presence of a DNA template encoding a gene of interest, the exogenous gene can be integrated into the Cas9-targeting site using either repair mechanisms. There are several ways to provide such a DNA template, including viral and non-viral methods. In non-viral approaches, the single-stranded or double-stranded DNA template is typically electroporated along with Cas9/RNP. For viral gene delivery, adeno-associated viruses (AAV) were used safely in clinical trials and are effective as vectors for sensitive primary immune cells, including T-cells. Transcripts that are delivered via AAV vectors can be packaged as a linear single-stranded (ss) DNA with a length of approximately 4.7 kb (ssAAV) or linear self-complementary (sc) DNA (scAAV). scAAV contains a mutated ITR which helps to bypass rate-limiting steps of second strand generation for converting ssDNA into double-stranded (ds)DNA. However, as a consequence, the scAAV has only half the packaging capacity compared to ssAAV and hence is not suitable for larger transgenes. Both ssAAV and scAAV are designed and tested for DNA template delivery into NK cells.

Stable gene integration through HR machinery depends on providing the transgenes with optimal homology arms for the flanking region of the DSB. To find the most optimal length of homology arms and optimize packaging capacity of a transgene into ssAAV and scAAV, 30 bp, 300 bp, 500 bp and 800-1000 bps of HAs were designed for the right and left side of Cas9-targeting site. Since designing homology arms is a time-consuming procedure and requires multiple optimizations, the CRISPaint approach was also investigated, a homology-independent method for gene insertion or tagging. In this method, the same Cas9 targeting site, including crRNA and PAM sequences, is provided in the DNA template encoding the gene of interest. Upon introduction of the Cas9 complex, both template and genomic DNA are cut simultaneously. As a result, the CRISPaint template is presented as a linearized double-stranded DNA which can be integrated through non-homology repair machinery. With both methods highly efficient and stable transgene-modified NK cells were generated using mCherry as a proof of concept.

Example 3 a) Human NK Cell Purification and Expansion.

NK cells were purified. Briefly, NK cells were isolated from PBMC using RosetteSep™ Human NK Cell Enrichment Cocktail (FIG. 8). Purified NK cells were phenotyped using flow cytometry as >90% CD3-negative/CD56-positive population (FIG. 9). These cells were stimulated with irradiated mbIL21-expressing K562 feeder cells at a ratio of 2:1 (feeder:NK) at the day of purification (FIG. 9). The stimulated cells were cultured for 7 days in the serum-free AIM-V/ICSR expansion medium containing 100 IU/mL of IL-2.

b) Targeting Genomic Safe Harbors for Gene Insert.

Genomic safe harbors (GSHs) are sites in the genome which can be modified with no change in the normal function of the host cell and allow adequate expression of the transgene. The adeno-associated virus site 1 (AAVS1) was chosen, which is one of the GSHs and an exemplary locus within the phosphatase 1 regulatory subunit 12C (PPP1R12C) gene. This locus has been successfully used for directed gene insertion into several cell types. First, the chromatin accessibility of AAVS1 was evaluated in naïve and expanded NK cells by ATAC-seq assay and showed no difference between the naïve and IL-21 expanded cells (FIG. 10). AAVS1 was targeted using one gRNA (crRNA: 5'GGGGCCACTAGGGACAGGAT (SEQ ID NO: 17)) via electroporation of Cas9/RNP into expanded NK cells as described before.

Briefly, $3 \times 10^6$ expanded NK cells were harvested and washed twice with 13 ml of PBS followed by centrifugation for 7 minutes at 300 g and aspiration of PBS. The cell pellet was resuspended in 20 ul of P3 Primary Cell 4D-Nucleofector Solution. 5 ul of pre-complexed Cas9/RNP (Alt-R® CRISPR-Cas9 crRNA, Alt-R® CRISPR-Cas9 tracrRNA and Alt-R® S.p. HiFi Cas9 Nuclease V3) (Integrated DNA Technologies, Inc., Coralville, Iowa), targeting AAVS1 and 1 ul of 100 uM electroporation enhancer (Alt-R® Cas9 Electroporation Enhancer) were added to the cell suspension. The total volume of 26 ul of CRISPR reaction was transferred into 4D-Nucleofector™ 16-well Strip and electroporated using program EN-138. After electroporation, the cells were transferred into 2 ml of serum-free media containing 100 IU of IL-2 in a 12 well plate (FIG. 11) and incubated at 37 degrees 5% $CO_2$ pressure.

After 48 hours, NK cell DNA was isolated for detection of Insertions deletions (Indels) in CRISPR edited NK cells. The region flanking the Cas9 targeting site was PCR amplified and the amplicons were Sanger sequenced. Inference of CRISPR Edits (ICE) was used to analyze the frequency of Indels (FIG. 12). The ICE results showed that more than 85% of CRISPR modified NK cells had at least one indel at the AAVS1 Cas9-targeting site. To ensure that genome modifications at this locus did not interfere with the ability to target cancer cells, cytotoxicity of AAVS1-KO NK cells was assessed using Kasumi, an AML cancer cell line. Using a Calcein AM assay, no difference between wild type and CRISPR modified NK cells in their killing ability was observed (FIG. 13).

c) Testing of Various Adeno-Associated Viral Vector Serotypes for DNA Template Deliver.

To determine the best serotype of AAV for transduction of primary NK cells and to provide the highest number of DNA template encoding gene of interest into NK cells, we transduced the cells with several serotypes of AAVs including AAV4, AAV6, AAV8 and AAV9 encoding GFP at a multiplicity of infection (MOI) of 300K. NK cells transduced with AAV6 had the highest expression level of GFP detected by flow cytometry. Importantly, the AAV6 viral genome can be detected up to 48 hours post-transduction by qPCR analysis, which is a critical time for the endonuclease function of Cas9 protein (FIG. 14).

d) Designing HR and CRISPaint Gene Delivery Construct.

After successful showing that the AAVS1 locus can be modified in NK cells without altering their ability to target cancer cells, AAV mediated delivery of the mCherry transgene for gene insertion at AAVS1 was evaluated. For HR-directed gene insertion, DNA-encoding mCherry with homology arms (HA) to the flanking region of Cas9-targeting site were cloned into the backbone of single-stranded or self-complementary AAV vector. 30 bp, 300 bp, 500 bp and 1000 bp of HA was designed for the right and 30 bp, 300 bp, 500 bp and 800 bp was designed for the left HA (FIG. 15). For the CRISPaint DNA templates, single (PAMg) or double (PAMgPAMg) Cas9-targeting sequences were incorporated around the mCherry transgene but within the ITRs. Therefore, Cas9 can simultaneously cut gDNA and the CRISPaint DNA template, enabling integration at the genomic DSB (FIGS. 16A-16B). To ensure the accuracy of the designed HR and CRISPaint DNA templates before packaging the transgenes into AAV6, the circular DNA encoding mCherry was co-electroporated with Cas9/RNP targeting AAVS1 into HEK293 cells. The results showed that both HR and CRISPaint DNAs were successfully integrated at the genomic DSB and mCherry was efficiently expressed (FIG. 17).

e) Studying the NHEJ and HR Pathways in the Primary NK Cells to Determine Optimal Pathway for Genome Editing.

CRISPaint and HR are regulated by enzymatic reactions. CRISPaint is a LIG4-dependent process, while other proteins such as BRCA1 and BRCA2 regulate HR. Therefore, expression levels of these genes in NK cells were analyzed to evaluate which repair pathway can be more efficient in this cell type. RNA-seq analysis showed that the expanded NK cells have higher expression of BRCA1 and BRCA2 in comparison with naïve NK cells and there is no decrease in LIG4 level in these cells (FIG. 18), providing optimal conditions for either HR or NHEJ-directed gene insertion through CRISPaint.

f) Combining Cas9/RNP and AAV6 to Generate mCherry NK Cells.

A media change and resuspension at $5 \times 10^5$ cells per ml was performed on day 6 of NK cell expansion one day prior to experimental manipulation. The NK cells were then electroporated with Cas9/RNP targeting AAVS1 on day 7 as described above. Thirty minutes after electroporation, live cells were collected and resuspended at $1 \times 10^6$ cells per ml in media containing 100 IU IL2 in a 24 well plate. For each transduction condition with ssAAV6 or scAAV6 to deliver HR or CRISPaint DNA encoding mCherry, 300K electroporated cells were transduced with 300K MOI or 150K MOI. Alternatively, to test the transduction efficiency of higher MOI of AAV6, 150,000 cells were transduced with 500K MOI of ssAAV6 delivering HR 800 bp and scAAV6 delivering CRISPaint PAMgPAMg (FIG. 19). Negative controls included NK cells that were not electroporated, were electroporated with Cas9/RNP but not AAV transduced, or were transduced with 300K MOI of AAV6 without electroporation of Cas9/RNP. The day after electroporation and transduction, 150 ul of fresh media containing 100 IU of IL2 was added to each well without changing the old media. The cells were kept in culture for 48 hours after electroporation and were then restimulated with K562 feeder cells at a ratio of 2:1 and kept in total volume of 1 ml in 24 well plate.

g) Flow Cytometry of CRISPR Modified Human NK Cells Shows Successful Integration of the mCherry Gene.

Two days after electroporation and transduction and before expansion, flow cytometry was performed to assess mCherry expression and viability (GhostRed 780 dye). As an overall, NK cells transduced with AAV6 delivering HR vectors had higher knock-in efficiency than CRISPaint. Furthermore, scAAV6 showed significantly better gene insertion. mCherry expression was not observed in control NK cells. Almost 20% of NK cells in the experimental conditions in which HR vectors were used to transduce cells with the ssAAV6 delivering DNA-encoding mCherry with 800 bp of HA, were mCherry positive. For NK cells which were transduced with 300K MOI of scAAV6 delivering CRISPaint PAMg or 300K MOI and 500K MOI of PAMg-PAMg, up to 8% of mCherry positive cells were found. Importantly, the percentage of mCherry positive cells was significantly higher in the cells that were transduced with the scAAV6 HR vectors containing the shorter homology arms. These conditions included transduction at 300K MOI or 150K MOI of HR scAAV6 vectors with 30 bp (19-20%), 300 bp (80-85%), 500 bp (75-85%), and 800 bp (80-89%). For the cells with lower transduction efficiency (ssAAV6-HR-800 bp, scAAV6-CRISPaint PAMgPAMg), the mCherry positive population was enriched to 85% by FACS sorting and was expanded for up to 20 days using irradiated mbIL21-expressing K562 feeder cells with no changes in the percentages of mCherry positive NK cells (FIGS. 20-22). The flow analysis was repeated for the expanded mCherry positive NK cells up to 20 days post transduction and no significant changes in percentages of mCherry were observed in the cells generated by a combination of Cas9/RNP and ssAAV6 or scAAV6. Although, lower efficiency of gene integration was observed using CRISPaint compared to HR-directed gene insertion, this method is still very attractive because it allows researchers to integrate genes of interest into a user-defined locus with no need for designing homology arms. Moreover, better expansion in NK cells transduced with CRISPaint vectors were observed.

h) Combining Cas9/RNP with Non-Viral Gene Delivery Causes Cell Death in Primary Human NK Cells.

In order to minimize the time and cost of virus production, non-viral gene integration has been used in T cells. This approach was also tested in NK cells by electroporating Cas9/RNP targeting AAVS1 with naked chemically-synthe- sized DNA encoding mCherry. The transgenes were gener- ated in 2 forms, one as Megamer® Single-Stranded DNA Fragments from IDT with 80 bp homology arms for the region flanking the Cas9-targeting site, and another with the same HR and CRISPaint DNAs that was cloned into the AAV backbone but were not packaged in any AAV capsids.

Expanded NK cells were electroporated with Cas9/RNP targeting AAVS1 and 1 or 2 ug of DNAs encoding mCherry in a total volume of 26 ul. After 2 days, the cells with Megamer® were 100% dead, and only 10% of the cells which were electroporated with the HR and CRISPaint DNA had survived. These cells can be expanded, but less than 1% of the resulting cells were mCherry positive although the DNA was integrated at the site of DSB. This indicates that AAV mediated NK cell modification is better tolerated and more efficient compared to naked DNA delivery.

---

SEQUENCES 30 bp right homology arm

SEQ ID NO: 1 gattggtgacagaaaagccccatccttagg 30 bp left homology arm

SEQ ID NO: 2 ttatctgtcccctccaccccacagtggggc 300 bp right homology arm

SEQ ID NO: 3 gattggtgacagaaaagccccatccttaggcctcctccttcctagtctcctgatattgggtctaacccccacctcctgttaggcagattccttat ctggtgacacacccccatttcctggagccatctctctccttgccagaacctctaaggtttgcttacgatggagccagagaggatcctgggag ggagagcttggcagggggtgggagggaaggggggggatgcgtgacctgcccggttctcagtggccaccctgcgctaccctctcccagaa cctgagctgctctgacgcggctgtc 300 bp left homology arm

SEQ ID NO: 4 gttctcctgtggattcgggtcacctctcactcctttcatttgggcagctccctacccccttacctctctagtctgtgctagctcttccagccccc tgtcatggcatcttccaggggtccgagagctcagctagtcttcttcctccaacccgggcccctatgtccacttcaggacagcatgtttgctgcc tccagggatcctgtgtccccgagctgggaccaccttatattcccagggccggttaatgtggctctggttctgggtacttttatctgtcccctcca ccccacagtggggc 500 bp right homology arm

SEQ ID NO: 5 gattggtgacagaaaagccccatccttaggcctcctccttcctagtctcctgatattgggtctaaccccccacctcctgttaggcagattccttat ctggtgacacacccccatttcctggagccatctctctccttgccagaacctctaaggtttgcttacgatggagccagagaggatcctgggag ggagagcttggcaggggagtgggagggaaggggggggatgcgtgacctgcccggttctcagtggccaccctgcgctaccctctcccagaa cctgagctgctctgacgcggctgtctggtgcgtttcactgatcctggtgctgcagcttccttacacttcccaagaggagaagcagtttggaaa aacaaaatcagaataagttggtcctgagttctaactttggctcttcacctttctagtccccaatttatattgttcctccgtgcgtcagttttacctgtg agataaggccagtagccagcccgtcctggcag 500 bp left homology arm

SEQ ID NO: 6 tccctttttccttctccttctggggcctgtgccatctctcgtttcttaggatggccttctccgacggatgtctcccttgcgtcccgcctcccettcttg taggcctgcatcatcaccgatactggacaaccccaaagtaccccgtctccctggcttttagccacctctccatcctcttgctttcttttgcctgga cacccgttctcctgtggattcgggtcacctctcactcctacatttgggcagctccctacccccttacctctctagtctgtgctagctcttcca gcccctgtcatggcatcttccaggggtccgagagctcagctagtcttcttcctccaacccgggcccctatgtccacttcaggacagcatgtt tgctgcctccagggatcctgtgtccccgagctgggaccaccttatattcccagggccggttaatgtggctctggttctgggtactttatctgtc ccctccaccccacagtggggc 800 bp right homology arm

SEQ ID NO: 7 gattggtgacagaaaagccccatccttaggcctcctccttcctagtctcctgatattgggtctaaccccacctcctgttaggcagattccttat ctggtgacacacccccatttcctggagccatctctctccttgccagaacctctaaggtttgcttacgatggagccagagaggatcctgggag ggagagcttggcaggggagtgggagggaaggggggggatgcgtgacctgcccggttctcagtggccaccctgcgctaccctctcccagaa cctgagctgctctgacgcggctgtctggtgcgtttcactgatcctggtgctgcagcttccttacacttcccaagaggagaagcagtttggaaa -continued

---

SEQUENCES

--- aacaaaatcagaataagttggtcctgagttctaacttttggctcttcacctttctagtccccaatttatattgttcctccgtgcgtcagttttacctgtg agataaggccagtagccagccccgtcctggcagggctgtggtgaggaggggggtgtccgtgtggaaaactcccttgtgagaatggtgc gtcctaggtgttcaccaggtcgtggccgcctctactcccttctctttctccatccttctttccttaaagagtccccagtgctatctgggacatattc ctccgcccagagcagggtcccgcttccctaaggccctgctctgggcttctgggtttgagtccttggcaagcccaggagaggcgctcaggc ttccctgtcccccttcctcgtccaccatctcatgccctggctctcctgcccttccctacaggggttcctggctctgtctcttcagactgagccc cgttccctgcatccccgttccctgcatccccttccctgcatccccagagcccaggccacctacttggcctggaccccacgagag gccaccccagccctgtctaccaggctgcctttggggtggattctcctccaactgtgggtgactgcttgg 800 bp left homology arm

SEQ ID NO: 8 tgctttctctgacctgcattctctcccctgggcctgtgccgcgcttctgtctgcagcttgtggcctgggtcacctctacggctggcccagatccttc cctgccgcctccttcaggttccgtcttcctccactccctcttccccttgctctctgctgtgttgctgcccaaggatgctctttccggagcacttcct tctcggcgctgcaccacgtgatgtcctctgagcggatcctccccgtgtctgggtcctctccgggcatctctcctccctcacccaacccatgc cgtcttcactcgctgggttcccttttccttctccttctggggcctgtgccatctctcgtttcttaggatggccttctccgacggatgtctcccttgcg tcccgcctccccttcttgtaggcctgcatcatcaccgttttctggacaaccccaaagtaccccgtctccctggctttagccacctctccatcct cttgctttctttgcctggacaccccgttctcctgtggattcgggtcacctctcactccttttcatttgggcagctccctacccccttacctctcta gtctgtgctagctcttccagcccctgtcatggcatcttccaggggtccgagagctcagctagtcttcttcctccaacccgggcccctatgtcc acttcaggacagcatgtttgctgcctccagggatcctgtgtccccgagctgggaccaccttatattcccagggccggttaatgtggctctggt tctgggtacttttatctgtcccctccaccccacagtggggc PAM gRNA

SEQ ID NO: 9 ccaatcctgtccctagtggcccc splice acceptor

SEQ ID NO: 10 atcgatcgcaggcgcaatcttcgcatttcttttttccag

BGH polyA terminator

SEQ ID NO: 11 cctcgactgtgccttctagttgccagccatctgttgtttgcccctcccccgtgccttccttgaccctggaaggtgccactcccactgtcctttcct aataaaatgaggaaattgcatcgcattgtctgagtaggtgtcattctattc mCherry

SEQ ID NO: 12 gtgagcaagggcgaggaggataacatggccatcatcaaggagttcatgcgcttcaaggtgcacatggagggctccgtgaacggccacg agttcgagatcgagggcgagggcgagggccgcccctacgagggcacccagaccgccaagctgaaggtgaccaagggtggccccctg cccttcgcctgggacatcctgtcccctcagttcatgtacggctccaaggcctacgtgaagcaccccgccgacatccccgactacttgaagct gtccttccccgagggcttcaagtgggagcgcgtgatgaacttcgaggacggcggcgtggtgaccgtgacccaggactcctccctgcagg acggcgagttcatctacaaggtgaagctgcgcggcaccaacttcccctccgacggccccgtaatgcagaagaagaccatgggctggga ggcctcctccgagcggatgtaccccgaggacggcgccctgaagggcgagatcaagcagagggctgaagctgaaggacggcggccact acgacgctgaggtcaagaccacctacaaggccaagaagcccgtgcagctgcccggcgcctacaacgtcaacatcaagttggacatcac ctcccacaacgaggactacaccatcgtggaacagtacgaacgcgccgagggccgccactccaccggcggcatggacgagctgtacaa gtaa 30 bp plasmid with incorporated mCherry transgene.

SEQ ID NO: 13 ttatctgtcccctccaccccacagtggggccactagggacagcgatcgggtacatcgatcgcaggcgcaatcttcgcatttcttttttccaggt gagcaagggcgaggaggataacatggccatcatcaaggagttcatgcgcttcaaggtgcacatggagggctccgtgaacggccacgag ttcgagatcgagggcgagggcgagggccgcccctacgagggcacccagaccgccaagctgaaggtgaccaagggtggcccccctgcc cttcgcctgggacatcctgtcccctcagttcatgtacggctccaaggcctacgtgaagcaccccgccgacatccccgactacttgaagctgt ccttcccccgagggcttcaagtgggagcgcgtgatgaacttcgaggacggcggcgtggtgaccgtgacccaggactcctccctgcaggac ggcgagttcatctacaaggtgaagctgcgcggcaccaacttcccctccgacggccccgtaatgcagaagaagaccatgggctgggagg cctcctccgagcggatgtaccccgaggacggcgccctgaagggcgagatcaagcagaggctgaagctgaaggacggcggccactac gacgctgaggtcaagaccacctacaaggccaagaagcccgtgcagctgcccggcgcctacaacgtcaacatcaagttggacatcacctc ccacaacgaggactacaccatcgtggaacagtacgaacgcgccgagggccgccactccaccggcggcatggacgagctgtacaagta acgcggccgccctcgactgtgccttctagttgccagccatctgttgtttgcccctcccccgtgccttccttgaccctggaaggtgccactccc actgtcctttcctaataaaatgaggaaattgcatcgcattgtctgagtaggtgtcattctattcgattggtgacagaaaagcccatccttagg 300 bp plasmid with incorporated mCherry transgene.

SEQ ID NO: 14 gttctcctgtggattcgggtcacctctcactcctttcatttgggcagctcccctacccccttacctctctagtctgtgctagctcttccagccccc tgtcatggcatcttccaggggtccgagagctcagctagtcttcttcctccaacccgggcccctatgtccacttcaggacagcatgtttgctgcc tccagggatcctgtgtccccgagctgggaccaccttatattcccagggccggttaatgtggctctggttctgggtacttttatctgtcccctcca ccccacagtggggccactagggacagcgatcgggtacatcgatcgcaggcgcaatcttcgcatttcttttttccaggtgagcaagggcgag gaggataacatggccatcatcaaggagttcatgcgcttcaaggtgcacatggagggctccgtgaacggccacgagttcgagatcgaggg cgagggcgagggccgcccctacgagggcacccagaccgccaagctgaaggtgaccaagggtggccccctgcccttcgcctgggacat cctgtccctcagttcatgtacggctccaaggcctacgtgaagcaccccgccgacatccccgactacttgaagctgtccttccccgagggct tcaagtgggagcgcgtgatgaacttcgaggacggcggcgtggtgaccgtgacccaggactcctccctgcaggacggcgagttcatctac aaggtgaagctgcgcggcaccaacttcccctccgacggccccgtaatgcagaagaagaccatgggctgggaggcctcctccgagcgga tgtaccccgaggacggcgccctgaagggcgagatcaagcagaggctgaagctgaaggacggcggccactacgacgctgaggtcaag accacctacaaggccaagaagcccgtgcagctgcccggcgcctacaacgtcaacatcaagttggacatcacctcccacaacgaggacta caccatcgtggaacagtacgaacgcgccgagggccgccactccaccggcggcatggacgagctgtacaagtaacgcggccgcccctcg actgtgccttctagttgccagccatctgttgtttgcccctcccccgtgccttccttgaccctggaaggtgccactcccactgtcctttcctaataa aatgaggaaattgcatcgcattgtctgagtaggtgtcattctattcgattggtgacagaaaagcccatccttaggcctcctccttcctagtctc ctgatattgggtctaacccccacctcctgttaggcagattccttatctggtgacacaccccatttcctggagccatctctctccttgccagaac ctctaaggtttgcttacgatggagccagagaggatcctgggagggagagcttggcaggggggtgggagggaagggggggatgcgtgac ctgcccggttctcagtggccaccctgcgctaccctctcccagaacctgagctgctctgacgcggctgtc 500 bp plasmid with incorporated mCherry transgene.

SEQ ID NO: 15 tccctttttccttctccttctgggggcctgtgccatctctcgtttcttaggatggccttctccgacggatgtctcccttgcgtcccgcctcccttcttg taggcctgcatcatcaccgttttttctggacaaccccaaagtaccccgtctccctggctttagccacctctccatcctcttgctttctttgcctgga caccccgttctcctgtggattcgggtcacctctcactcctacatttgggcagctcccctacccccttacctctctagtctgtgctagctcttcca gcccctgtcatggcatcttccaggggtccgagagctcagctagtcttcttcctccaacccgggcccctatgtccacttcaggacagcatgtt tgctgcctccagggatcctgtgtccccgagctgggaccaccttatattcccagggccggttaatgtggctctggttctgggtacttttatctgtc ccctccaccccacagtggggccactagggacagcgatcgggtacatcgatcgcaggcgcaatcttcgcatttcttttttccaggtgagcaa gggcgaggaggataacatggccatcatcaaggagttcatgcgcttcaaggtgcacatggagggctccgtgaacggccacgagttcgaga tcgagggcgagggcgagggccgcccctacgagggcacccagaccgccaagctgaaggtgaccaagggtggcccctgcccttcgcc tgggacatcctgtccctcagttcatgtacggctccaaggcctacgtgaagcaccccgccgacatccccgactacttgaagctgtccttccc cgagggcttcaagtgggagcgcgtgatgaacttcgaggacggcggcgtggtgaccgtgacccaggactcctccctgcaggacggcga gttcatctacaaggtgaagctgcgcggcaccaacttcccctccgacggccccgtaatgcagaagaagaccatgggctgggaggcctcct ccgagcggatgtaccccgaggacggcgccctgaagggcgagatcaagcagaggctgaagctgaaggacggcggccactacgacgct

SEQUENCES gaggtcaagaccacctacaaggccaagaagcccgtgcagctgcccggcgcctacaacgtcaacatcaagttggacatcacctcccacaa cgaggactacaccatcgtggaacagtacgaacgcgccgagggccgccactccaccggcggcatggacgagctgtacaagtaacgcgg ccgccctcgactgtgccttctagttgccagccatctgttgtttgccctcccccgtgccttccttgaccctggaaggtgccactcccactgtcct ttcctaataaaatgaggaaattgcatcgcattgtctgagtaggtgtcattctattcgattggtgacagaaaagccccatccttaggcctcctcctt cctagtctcctgatattgggtctaaccccacctcctgttaggcagattccttatctggtgacacaccccatttcctggagccatctctctcctt gccagaacctctaaggtttgcttacgatggagccagagaggatcctgggagggagagcttggcagggggtgggagggaaggggggga tgcgtgacctgcccggttctcagtggccaccctgcgctaccctctcccagaacctgagctgctctgacgcggctgtctggtgcgtttcactg atcctggtgctgcagcttccttacacttcccaagaggagaagcagtttggaaaaacaaaatcagaataagttggtcctgagttctaactttggc tcttcacctttctagtccccaatttatattgttcctccgtgcgtcagttttacctgtgagataaggccagtagccagccccgtcctggcag 800 bp plasmid with incorporated mCherry transgene.

SEQ ID NO: 16 tgctttctctgacctgcattctctcccctgggcctgtgccgctttctgtctgcagcttgtggcctgggtcacctctacggctggcccagatccttc cctgccgcctccttcaggttccgtcttcctccactccctcttcccccttgctctctgctgtgttgctgcccaaggatgctctttccggagcacttcct tctcggcgctgcaccacgtgatgtcctctgagcggatcctccccgtgtctgggtcctctccgggcatctctcctccctcacccaaccccatgc cgtcttcactcgctgggttccctttttccttctccttctggggcctgtgccatctctcgtttcttaggatggccttctccgacggatgtctcccttgcg tcccgcctccccttcttgtaggcctgcatcatcaccgttttttctggacaaccccaaagtaccccgtctccctggctttagccacctctccatcct cttgctttctttgcctggacacccccgttctcctgtggattcgggtcacctctcactcctttcatttgggcagctcccctacccccttacctctcta gtctgtgctagctcttccagcccctgtcatggcatcttccaggggtccgagagctcagctagtcttcttcctccaacccgggcccctatgtcc acttcaggacagcatgtttgctgcctccagggatcctgtgtccccgagctgggaccaccttatattcccagggccggttaatgtggctctggt tctgggtactttatctgtcccctccaccccacagtggggccactagggacagcgatcgggtacatcgatcgcaggcgcaatcttcgcatttc ttttttccaggtgagcaagggcgaggaggataacatggccatcatcaaggagttcatgcgcttcaaggtgcacatggagggctccgtgaac ggccacgagttcgagatcgagggcgagggcgagggccgcccctacgagggcacccagaccgccaagctgaaggtgaccaagggtg gcccctgcccttcgcctgggacatcctgtccctcagttcatgtacggctccaaggcctacgtgaagcaccccgccgacatccccgacta cttgaagctgtccttccccgagggcttcaagtgggagcgcgtgatgaacttcgaggacggcggcgtggtgaccgtgacccaggactcctc cctgcaggacggcgagttcatctacaaggtgaagctgcgcggcaccaacttcccctccgacggccccgtaatgcagaagaagaccatgg gctgggaggcctcctccgagcggatgtaccccgaggacggcgccctgaagggcgagatcaagcagaggctgaagctgaaggacggc ggccactacgacgctgaggtcaagaccacctacaaggccaagaagcccgtgcagctgcccggcgcctacaacgtcaacatcaagttgg acatcacctcccacaacgaggactacaccatcgtggaacagtacgaacgcgccgagggccgccactccaccggcggcatggacgagc tgtacaagtaacgcggccgccctcgactgtgccttctagttgccagccatctgttgttgcccctcccccgtgccttccttgaccctggaaggt gccactcccactgtcctttcctaataaaatgaggaaattgcatcgcattgtctgagtaggtgtcattctattcgattggtgacagaaaagcccca tccttaggcctcctccttcctagtctcctgatattgggtctaaccccacctcctgttaggcagattccttatctggtgacacaccccatttcctg gagccatctctctccttgccagaacctctaaggtttgcttacgatggagccagagaggatcctgggagggagagcttggcagggggtggg agggaagggggggatgcgtgacctgcccggttctcagtggccaccctgcgctaccctctcccagaacctgagctgctctgacgcggctgt ctggtgcgtttcactgatcctggtgctgcagcttccttacacttcccaagaggagaagcagtttggaaaaacaaaatcagaataagttggtcct gagttctaactttggctcttcacctttctagtccccaatttatattgttcctccgtgcgtcagttttacctgtgagataaggccagtagccagcccc gtcctggcagggctgtggtgaggagggggggtgtccgtgtggaaaactccctttgtgagaatggtgcgtcctaggtgttcaccaggtcgtgg ccgcctctactccctttctctttctccatccttctttccttaaagagtccccagtgctatctgggacatattcctccgcccagagcagggtcccgc ttccctaaggccctgctctgggcttctgggtttgagtccttggcaagcccaggagaggcgctcaggcttccctgtcccccttcctcgtccacc atctcatgcccctggctctcctgccccttccctacaggggttcctggctctgctcttcagactgagccccgttccctgcatccccgttcccct gcatcccccttccctgcatccccagagggccccaggccacctacttggcctggaccccacgagaggccacccagccctgtctaccag

| SEQUENCES |
| --- | gctgccttttgggtggattctcctccaactgtggggtgactgcttgg (crRNA)

SEQ ID NO: 17

GGGGCCACTAGGGACAGGAT

---

What is claimed is:

1. A method of genetically modifying a primary NK cell or an expanded NK cell by homologous directed repair comprising a) obtaining a ribonucleoprotein (RNP) complex comprising a class 2 CRISPR/Cas endonuclease (Cas9) complexed with a corresponding CRISPR/Cas guide RNA and an AAV vector comprising a plasmid comprising a transgene; wherein the transgene is flanked by a left homology arm and a right homology arm; wherein the left homology arm and the right homology arm have a length of 30-800 bps, and wherein the right homology arm comprises a nucleic acid sequence selected from SEQ ID NO: 1, SEQ ID NO: 3, SEQ ID NO: 5, or SEQ ID NO: 7, and the left homology arm comprises a nucleic acid sequence selected from SEQ ID NO: 2, SEQ ID NO: 4, SEQ ID NO: 6, or SEQ ID NO: 8, wherein the plasmid comprises any combination of left homology arm length and right homology arm length, and wherein the RNP complex is encoded on the same AA V or a different AAV; and b) introducing the transgene and the RNP complex into the primary NK cell or the expanded NK cell; wherein the transgene is introduced into the primary NK cell or the expanded NK cell via infection with the Adeno-associated virus (AA V) into the primary NK cell or the expanded NK cell; wherein the RNP complex hybridizes to a target sequence within the genomic DNA of the primary NK cell or the expanded NK cell and the primary NK cell's or the expanded NK cell's DNA repair enzymes insert the transgene into the host genome at the target sequence within the genomic DNA of the cell thereby creating a modified primary NK cell or a modified expanded NK cell.

2. The method of claim 1, wherein the primary NK cell is incubated for 4 days in the presence of IL-2 prior to infection.

3. The method of claim 2, wherein the primary NK cell is expanded for 4 days in the presence of irradiated feeder cells prior to infection.

4. The method of claim 1, further comprising expanding the modified primary NK cell or a modified expanded NK cell with irradiated mbIL-21 expressing feeder cells following infection.

5. The method of claim 1, wherein the transgene is a chimeric antigen receptor for a tumor antigen.

6. The method of claim 1, wherein the RNP complex is introduced into the primary NK cell or the expanded NK cell via electroporation.

7. The method of claim 1, wherein the RNP complex is introduced into the primary NK cell or the expanded NK cell via transfection.

8. A method of genetically modifying at least one primary NK cell or at least one expanded NK cell by homology directed repair (HDR) comprising:

(a) introducing into the cell (i) a ribonucleoprotein (RNP) complex comprising a class 2 CRISPR/Cas endonuclease complexed with a CRISPR/Cas guide RNA encoding a target sequence in the primary NK cell genome or the expanded NK cell genome, and (ii) an AAV vector comprising a plasmid comprising a transgene flanked by first and second homology arms each having a length of 30-800 bps, wherein the first homology arm comprises a nucleic acid sequence selected from SEQ ID NO: 1, SEQ ID NO: 3, SEQ ID NO: 5, or SEQ ID NO: 7, and the second homology arm comprises a nucleic acid sequence selected from SEQ ID NO: 2, SEQ ID NO: 4, SEQ ID NO: 6, or SEQ ID NO: 8, wherein the plasmid comprises any combination of left homology arm length and right homology arm length, wherein the transgene encodes a chimeric antigen receptor, and wherein the RNP complex is encoded on the same AAV or a different AAV; and (b) maintaining the primary NK cell or the expanded NK cell for a time and under conditions sufficient for (i) the RNP complex to hybridize to the target sequence and introduce a double-stranded break (DSB) in the target sequence; and (ii) the primary NK cell or the expanded NK cell to insert the transgene into the primary NK cell or the expanded NK cell genome at the target sequence and repair the break by HDR, thereby incorporating the transgene into the primary NK cell genome or the expanded NK cell genome at the site of the DSB.

9. The method of claim 7, wherein the primary NK cell or the expanded NK cell is incubated for at least about 4 days in the presence of IL-2 prior to step (a).

10. The method of claim 7, wherein the primary NK cell or the expanded NK cell is expanded for at least about 4 days in the presence of mbIL-21 after step (b).

11. The method of claim 10, wherein the mbIL-21 comprises irradiated mbIL-21 expressing feeder cells, PM21 particles, EX21 exosomes, or any combination thereof.

* * * * *